US010837965B2

(12) United States Patent
Pennington et al.

(10) Patent No.: US 10,837,965 B2
(45) Date of Patent: Nov. 17, 2020

(54) METHODS FOR DETECTING LEVELS OF PIGMENT EPITHELIUM-DERIVED FACTOR AND ANTITHROMBIN-III FOR CHARACTERISING AND/OR PROGNOSING PROSTATE CANCER

(71) Applicant: University College Dublin, National University of Ireland, Dublin, Belfield (IE)

(72) Inventors: Stephen Pennington, Whitegate (IE); Brendan Murphy, Leixlip (IE); William Watson, Lucan (IE)

(73) Assignee: UNIVERSITY COLLEGE DUBLIN, NATIONAL UNIVERSITY OF IRELAND, Dublin (IE)

( * ) Notice: Subject to any disclaimer, the term of this patent is extended or adjusted under 35 U.S.C. 154(b) by 0 days.

(21) Appl. No.: 15/106,582

(22) PCT Filed: Dec. 19, 2014

(86) PCT No.: PCT/EP2014/078914
§ 371 (c)(1),
(2) Date: Jun. 20, 2016

(87) PCT Pub. No.: WO2015/092046
PCT Pub. Date: Jun. 25, 2015

(65) Prior Publication Data
US 2017/0010269 A1 Jan. 12, 2017

(30) Foreign Application Priority Data
Dec. 20, 2013 (GB) .................................. 1322800.2

(51) Int. Cl.
*G01N 33/53* (2006.01)
*G01N 33/574* (2006.01)
*C07K 14/47* (2006.01)
*C07K 14/81* (2006.01)
*C12N 9/64* (2006.01)
*C12N 9/68* (2006.01)

(52) U.S. Cl.
CPC ....... *G01N 33/57434* (2013.01); *C07K 14/47* (2013.01); *C07K 14/473* (2013.01); *C07K 14/8121* (2013.01); *C07K 14/8128* (2013.01); *C12N 9/6435* (2013.01); *G01N 2800/52* (2013.01)

(58) Field of Classification Search
None
See application file for complete search history.

(56) References Cited

U.S. PATENT DOCUMENTS

2009/0104639 A1* 4/2009 Bowser ............. G01N 33/6896
435/23
2010/0131432 A1* 5/2010 Kennedy ............. C12Q 1/6886
705/500

2011/0082089 A1 4/2011 Borlak et al.
2014/0038203 A1* 2/2014 Arthur ............... G01N 33/6893
435/7.4
2014/0296108 A1* 10/2014 Hickok ................... G06F 19/18
506/12

FOREIGN PATENT DOCUMENTS

WO 2007022248 A2 2/2007
WO 2009074350 A2 6/2009
WO 2013044099 A1 3/2013

OTHER PUBLICATIONS

Gomella et al (2010. Ther Adv Urol. 2(4): 171-181).*
Rauh et al, 2011. Journal of Chromatography B, 883-884: 59-67.*
Fragnoud et al, 2012 (Proteome Science, 10:60; published Oct. 26, 2012; 8 pages as printed).*
Turtoi et al, 2010. Talanta. 80: 1487-1495.*
Examination Report in corresponding GB Appln. No. 1322800.2, dated Sep. 12, 2014.
International Search Report and Written Opinion in corresponding PCT Appln. No. PCT/EP2014/078914, dated Jul. 29, 2015.
Alikhan, M. A. et al., "Prognostic Significance of Plasminogen System in Advanced Prostate Cancer: A Pilot Study", Journal of Clinical Oncology, vol. 23, No. 16S (Jun. 1 Supplement), 4766-4767 (2005).
Byrne, Jennifer C. et al., "2D-DIGE as a Strategy to Identify Serum Markers for the Progression of Prostate Cancer", Journal of Proteome Research, 8, 942-957 (2009).
Evans, Caroline A. et al., "Prostate Cancer Proteomics: The Urgent Need for Clinically Validated Biomarkers", Proteomics Clin. Appl., 3, 197-212 (2009).
Fortin, Tanguy et al., "Clinical Quantitation of Prostate-specific Antigen Biomarker in the Low Nanogram/Milliliter Range by Conventional Bore Liquid Chromatography-Tandem Mass Sepctrometry (Multiple Reaction Monitoring) Coupling and Correlation with ELISA Tests", Molecular & Cellular Proteomics 8: 1006-1015 (2009).
Lin, Jian-feng et al., "Identification of Candidate Prostate Cancer Biomarkers in prostate Needle Biopsy Specimens Using Proteomic Analysis", International Journal of Cancer, 121, 2596-2605 (2007).
Rantalainen, Mattias et al., "Statistically Integrated Metabonomic-Proteomic Studies on a Human Prostate Cancer Xenograft Model in Mice", Journal of Proteome Research, 5, 2642-2655 (2006).

(Continued)

*Primary Examiner* — Zachary C Howard
(74) *Attorney, Agent, or Firm* — Quarles & Brady LLP

(57) ABSTRACT

A method is provided for characterising and/or prognosing prostate cancer in a subject comprising measuring the level of at least one protein from a panel or at least one peptide thereof in a sample from the subject. The method may be used to determine the grade and stage of the prostate cancer. Also disclosed is a method for selecting a treatment for prostate cancer, together with corresponding methods of treatment. Systems and computing devices for performing the methods are also provided.

13 Claims, 45 Drawing Sheets
Specification includes a Sequence Listing.

(56) References Cited

OTHER PUBLICATIONS

Schiffer, Eric, "Biomarkers for Prostate Cancer", World Journal of Urology, 25, 557-562 (2007).
Wang, Xiao-Song et al., "Characterization of KRAS Rearrangements in Metastatic Prostate Cancer", Cancer Discovery, 1, 35-43 (2011).
Cao, Yue, et al., "Anti-Thrombin is Expressed in the Benign Prostatic Epithelium and in Prostate Cancer and is Capable of Forming Complexes with Prostate-Specific Antigen and Human Glandular Kallikrein 2", American Journal of Pathology, vol. 161, No. 6, Dec. 1, 2002, pp. 2053-2063.
Fan, Yue, et al., "Applying Random Forests to Identify Biomarker Panels in Serum 2D-DIGE Data for the Detection and Staging of Prostate Cancer", Journal of Proteome Research, vol. 10, No. 3, Mar. 4, 2011, pp. 1361-1373.
Hong, Sung Kyu, et al., "Alteration of Antithrombin III and D-dimer Levels in Clinically Localized Prostate Cancer", Korean Journal of Urology, vol. 51, No. 1, Jan. 1, 2010, pp. 25-29.
Jayapalan, Jaime J., et al., "Identification of Potential Complementary Serum Biomarkers to differentiate Prostate Cancer from Benign Prostatic Hyperplasia Using gel- and lectin-based Proteomics Analyses", Proteomics, vol. 33, No. 12, Jul. 28, 2012 pp. 1855-1862.
Oon, Sheng F., et al., "The Identification and Internal Validation of a Preoperative Serum Biomarker Panel to Determine Extracapsular Extension in Patients with Prostate Cancer", The Prostate, vol. 72, No. 14, Mar. 13, 2012, pp. 1523-1531.
Qingyl, Zhu, et al., "Unfavorable Prognostic Value of Human PEDF Decreased in High-Grade Prostatic Intraepithelial Neoplasia: A Differential Proteomics Approach", Cancer Investigation, vol. 27, No. 7, Jan. 1, 2009, pp. 794-801.
Stewart, John M., et al., "Bradykinin Antagonists as New Drugs for Prostate Cancer", International Immunopharmacology, vol. 2, No. 13-14, Dec. 1, 2002, pp. 1781-1786.
European Search Report for EP 14843200 dated Sep. 15, 2017.
European Examination Report issued in corresponding EP Application No. 14843200.8, dated Feb. 26, 2018.
European Examination Report issued in corresponding EP Application No. 14843200.8, dated Jun. 7, 2018.
European Patent Office, Extended European Search Report for application 19185536.0, dated Jan. 22, 2020.
Grayhack, J. T., et al. "Biochemical profiles of prostatic fluid from normal and diseased prostate glands." The prostate 1.2 (1980): 227-237.
Grayhack, J. T., et al. "Detection of carcinoma of the prostate utilizing biochemical observations." Cancer 45 (1980): 1896-1901.
Karczmarski, J., et al. "Pre-analytical-related variability influencing serum peptide profiles demonstrated in a mass spectrometry-based search for colorectal and prostate cancer biomarkers." Acta Biochimica Polonica 60.3 (2013).

\* cited by examiner

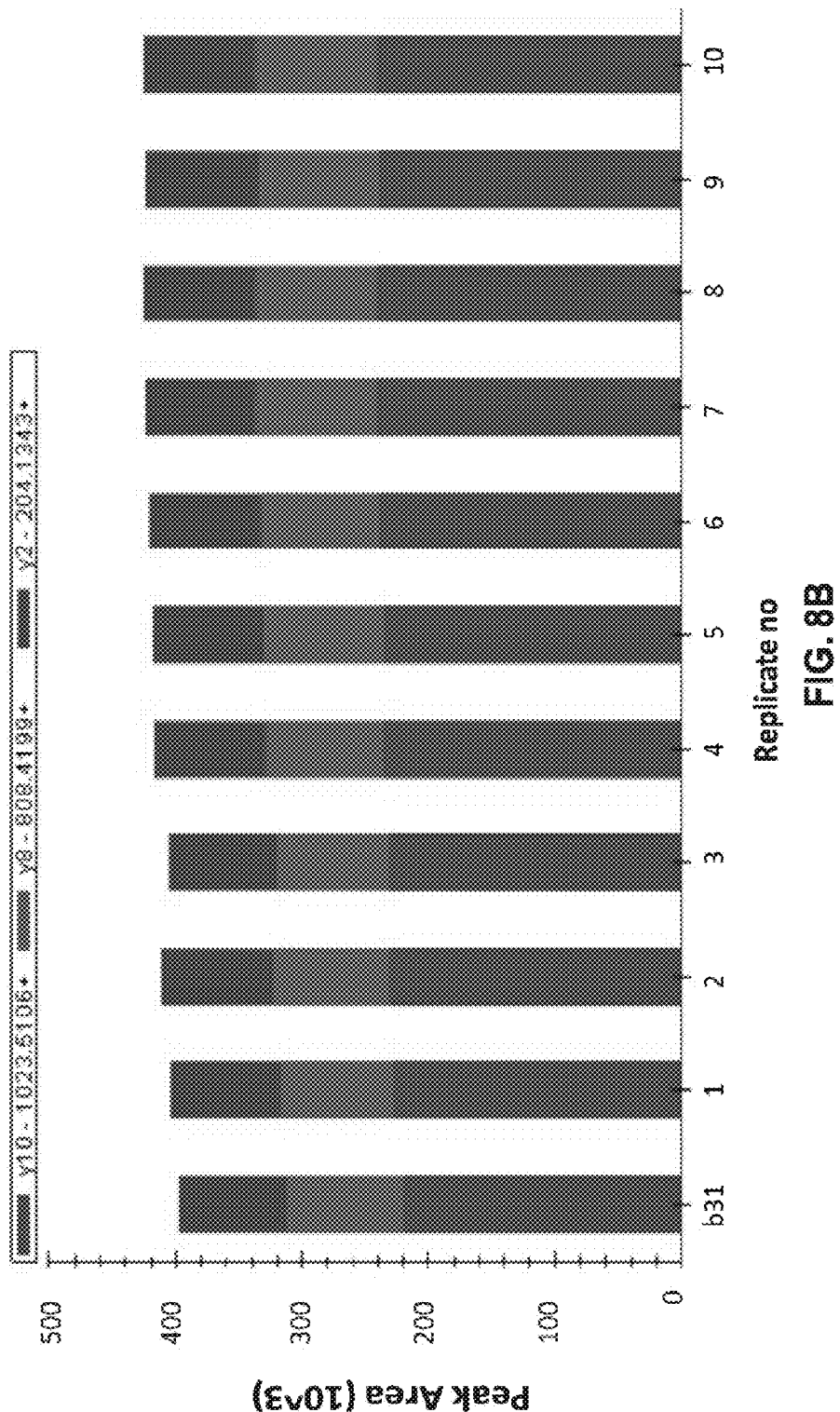

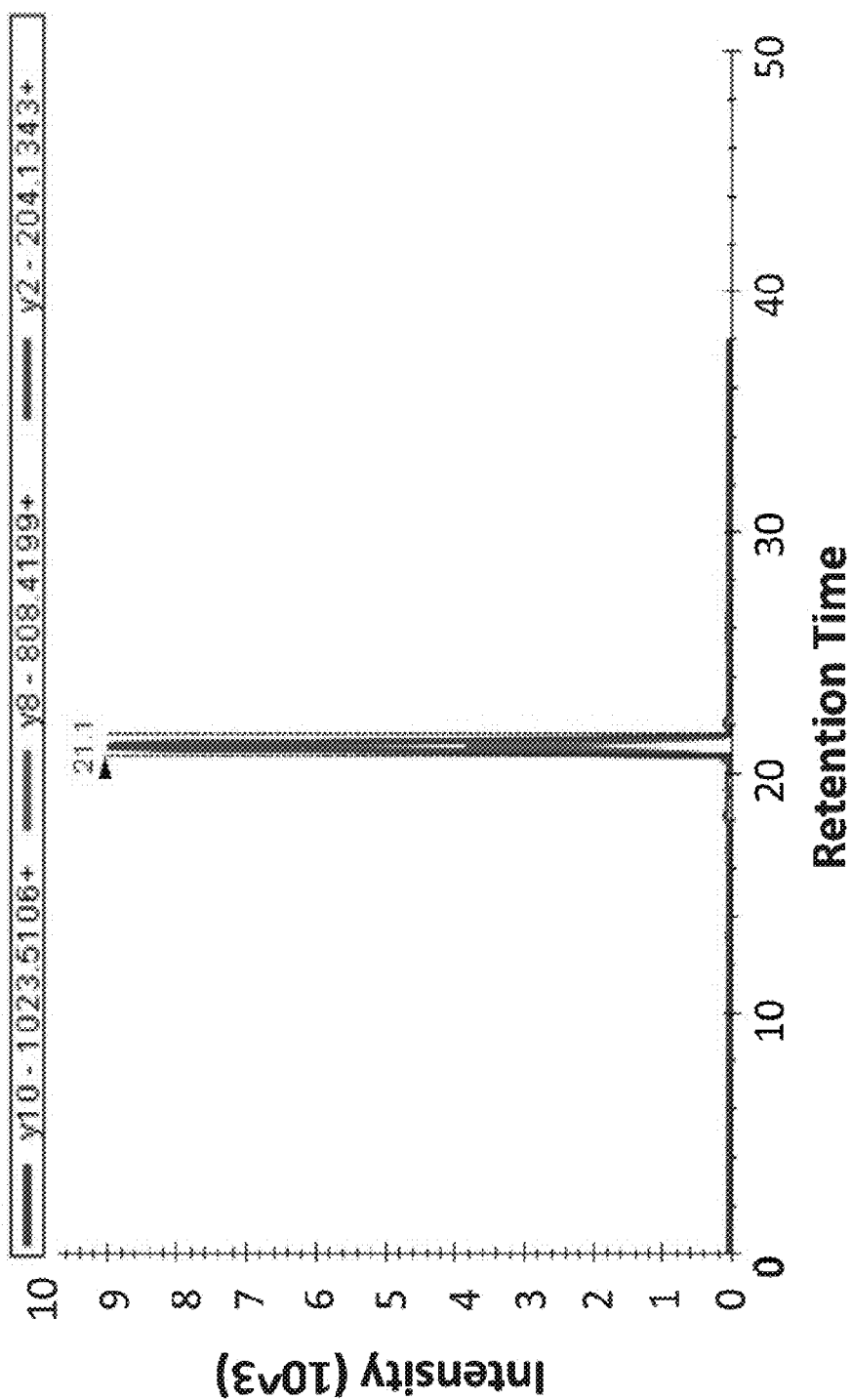

METHODS FOR DETECTING LEVELS OF PIGMENT EPITHELIUM-DERIVED FACTOR AND ANTITHROMBIN-III FOR CHARACTERISING AND/OR PROGNOSING PROSTATE CANCER

CROSS REFERENCE TO RELATED APPLICATION

The present application is the U.S. national stage of International Application PCT/EP2014/078914, filed on Dec. 19, 2014, which international application was published on Jun. 25, 2015 as International Publication No. WO 2015/092046. The International Application claims priority to British Patent Application No. 1322800.2, filed on Dec. 20, 2013, the contents of which are incorporated herein by reference in their entireties.

FIELD OF THE INVENTION

The present invention relates to prostate cancer. Provided are methods for characterising and prognosing prostate cancer which rely upon a range of biomarkers. Antibodies, kits, peptides and panels of biomarkers useful in the methods are also envisaged.

BACKGROUND OF THE INVENTION

Prostate cancer is the most common form of male cancer in the US and Europe, accounting for more than 20% of all newly diagnosed cancer cases in men. The accurate determination of the Gleason score and the stages of prostate cancer is of great significance in clinical decision making for the selection of the most appropriate patient management strategy. Due to the heterogeneity of the disease and randomness of the biopsy, often the biopsy does not provide an accurate representation about the extent and progression of the disease preoperatively. In addition, serum prostate-specific antigen (PSA), the only biomarker widely used in the diagnosis and management of patients with prostate cancer, is known to lack specificity. Attempts have been made to use neural networks to improve prostate cancer staging by combining input data including preoperative serum PSA and biopsy Gleason score (WO 98/39721). Additional biomarkers for grade and stage of disease are, however, required (Oon et al. Nature Reviews Urology 8, 2011, 131-138).

With recent advances in technology, proteomics has become a promising technique for the discovery of biomarkers (Goo and Goodlett, Journal of Proteomics 73, 2010, 1839-1850).

Fan et al., Journal of Proteome Research 10, 2011, 1361-1373 describe using two dimensional difference in gel electrophoresis (2D-DIGE) to identify proteins differentially expressed between benign prostatic hyperplasia (BPH), Gleason score 5 and 7.

Skvortsov et al., Journal of Proteome Research 2011, 10, 259-268 report on the use of 2D-DIGE in combination with laser capture microdissection and MALDI-TOF/TOF mass spectrometry to identify differences in protein expression between benign, Gleason score 6 and 8+ tumour tissues.

Glen et al., The Prostate 70, 2010, 1313-1332 describe the use of isobaric Tags for Relative and Absolute Quantitation (iTRAQ) to profile the proteomes of prostate cancer cells with varying growth and metastatic potentials.

Goo et al., The Prostate, 2009; 69:49-61 discuss the identification of secreted proteins from cultured normal prostate and bladder stromal mesenchyme cells by a glycopeptides-capture method followed by mass spectrometry.

The use of the targeted mass spectrometry based method, multiple reaction monitoring—MRM (also referred to as selected reaction monitoring—SRM), provides a relatively straightforward approach for quantitative validation of protein biomarkers due to its high sensitivity, dynamic range and the ease with which protein measurements can be multiplexed (Huttenhain et al., Current Opinion in Chemical Biology 13, 2009, 518-25).

Picotti et al., Nature Methods 7, 2010, 43-6 describe a method for the high-throughput development of MRM assays, which is illustrated by the generation of MRM assays for all *Saccharomyces cerevisiae* kinases and phosphatases.

Jenkins et al., Proteomics, 2006, 6, 1934-1947 describe quantification of cytochromes P450 in microsome preparations using MRM mass spectrometry.

DESCRIPTION OF THE INVENTION

The present invention is based upon the identification and verification of prostate cancer biomarkers. The technology used to determine these biomarkers involved coupling label-free LC-MS/MS with MRM.

A "tissue to serum" approach has become increasingly popular in the cancer biomarker discovery field. Differentially expressed proteins (most commonly glycoproteins or secreted proteins) are first identified from cell lines, animal models or clinical tissue samples and then these biomarkers are measured in the serum/plasma to evaluate if they also can be used as serum biomarkers. However these changes do not always correlate well with the expression patterns in serum. A more direct approach is to identify serum biomarkers through profiling the serum proteome. Compared with tissue samples, serum provides an easily accessible sample, which can be sampled over time for disease monitoring. However, serum also presents well known analytical challenges most notably the large dynamic range of protein concentration (>10 orders of magnitude).

The present inventors pooled serum samples from 3 groups of patients: low grade disease (Gleason score 5), high grade disease (Gleason score 7) and high grade with extracapsular extension (ECE). The samples were then depleted, tryptic digested and subjected to label-free LC-MS/MS. An MRM assay was developed for 33 proteins which were identified from the label-free LC-MS/MS experiment and a literature review. The developed MRM was tested for reproducibility on both depleted and crude serum samples. Subsequently, this MRM assay was applied to an independent 63 crude serum samples from prostate cancer patients for the verification stage of the study. The MRM results showed highly favorable prediction accuracies in classifying different Gleason scores and stages.

Thus, in a first aspect the invention provides a method for characterising and/or prognosing prostate cancer in a subject comprising:
measuring the level of at least one protein from list A or at least one peptide thereof in a sample
List A—33 Protein Panel

| Protein Names | Uniprot Accession No. | Peptide Sequence | SEQ ID No. |
|---|---|---|---|
| Plasminogen | P00747 | LSSPAVITDK | 1 |
|  |  | EAQLPVIENK | 2 |

-continued

| Protein Names | Uniprot Accession No. | Peptide Sequence | SEQ ID No. |
|---|---|---|---|
| Alpha-1-antitrypsin | P01009 | LSITGTYDLK | 3 |
| | | SVLGQLGITK | 4 |
| Alpha-1-antichymotrypsin | P01011 | EIGELYLPK | 5 |
| | | ADLSGITGAR | 6 |
| Alpha-2-macroglobulin | P01023 | NEDSLVFVQTDK | 7 |
| Antithrombin-III | P01008 | TSDQIHFFFAK | 8 |
| Apolipoprotein A-I | P02647 | DYVSQFEGSALGK | 9 |
| | | LLDNWDSVTSTFSK | 10 |
| Apolipoprotein A-II | P02652 | EPCVESLVSQYFQTVTDYGK | 11 |
| Apolipoprotein A-IV | P06727 | SELTQQLNALFQDK | 12 |
| | | IDQNVEELK | 13 |
| Apolipoprotein C-III | P02656 | DALSSVQESQVAQQAR | 14 |
| | | GWVTDGFSSLK | 15 |
| Apolipoprotein E | P02649 | WVQTLSEQVQEELLSSQVTQELR | 16 |
| | | VQAAVGTSAAPVPSDNH | 17 |
| Caveolin-1 | Q03135 | ASFTTFTVTK | 18 |
| Clusterin | P10909 | ELDESLQVAER | 19 |
| | | VTTVASHTSDSDVPSGVTEVVK | 20 |
| Complement C3 | P01024 | SSLSVPYVIVPLK | 21 |
| | | DFDFVPPVVR | 22 |
| Complement C4-A/B | P0C0L4 P0C0L5 | VGDTLNLNLR | 23 |
| | | GLEEELQFSLGSK | 24 |
| Complement component C6 | P13671 | SEYGAALAWEK | 25 |
| Complement component C9 | P02748 | TEHYEEQIEAFK | 26 |
| | | LSPIYNLVPVK | 27 |
| Ficolin-3 | O75636 | YGIDWASGR | 28 |
| Haptoglobin | P00738 | TEGDGVYTLNNEK | 29 |
| | | VTSIQDWVQK | 30 |
| Haptoglobin-related protein | P00739 | VGYVSGWGQSDNFK | 31 |
| Hemopexin | P02790 | NFPSPVDAAFR | 32 |
| | | SGAQATWTELPWPHEK | 33 |
| Insulin-like growth factor-binding protein 3 | P17936 | FLNVLSPR | 34 |
| Inter-alpha-trypsin inhibitor heavy chain H4 | Q14624 | NVVFVIDK | 35 |
| | | ILDDLSPR | 36 |
| Kininogen-1 | P01042 | TVGSDTFYSFK | 37 |
| | | IASFSQNCDIYPGK | 38 |
| Leucine rich α-2-glycoprotein | P02750 | DLLLPQPDLR | 39 |
| | | VAAGAFQGLR | 40 |
| Pigment epithelium-derived factor | P36955 | TVQAVLTVPK | 41 |
| | | DTDTGALLFIGK | 42 |
| Protein AMBP | P02760 | ETLLQDFR | 43 |
| Serotransferrin | P02787 | YLGEEYVK | 44 |
| Serum albumin | P02768 | LVNEVTEFAK | 45 |
| | | FQNALLVR | 46 |
| Serum amyloid P-component | P02743 | DNELLVYK | 47 |
| | | QGYFVEAQPK | 48 |
| Vitamin D-binding protein | P02774 | SCESNSPFPVHPGTAECCTK | 49 |
| Vitronectin | P04004 | DVWGIEGPIDAAFTR | 50 |
| | | FEDGVLDPDYPR | 51 |
| Zinc alpha-2-glycoprotein | P25311 | HVEDVPAFQALGSLNDLQFFR | 52 |

List B—Non-ECE/ECE

| Protein | Peptide | SEQ ID No. |
|---|---|---|
| Zinc alpha-2-glycoprotein | HVEDVPAFQALGSLNDLQFFR | 52 |
| Kininogen-1 | IASFSQNCDIYPGK | 38 |
| | TVGSDTFYSFK | 37 |

-continued

| Protein | Peptide | SEQ ID No. |
|---|---|---|
| Hemopexin | SGAQATWTELPWPHEK | 33 |
| Serum albumin | FQNALLVR | 46 |
| | LVNEVTEFAK | 45 |
| Serotransferrin | YLGEEYVK | 44 |
| Complement C3 | SSLSVPYVIVPLK | 21 |
| Inter-alpha-trypsin inhibitor heavy chain H4 | ILDDLSPR | 36 |
| | NVVFVIDK | 35 |
| Antithrombin-III | TSDQIHFFFAK | 8 |
| Apolipoprotein A-I | LLDNWDSVTSTFSK | 10 |
| Complement C4-A/B | GLEEELQFSLGSK | 24 |
| Pigment epithelium-derived factor | TVQAVLTVPK | 41 |
| Haptoglobin-related protein | VGYVSGWGQSDNFK | 31 |
| Plasminogen | LSSPAVITDK | 1 |

List C—Gleason Score 6/7

| Protein | Peptide | SEQ ID No. |
|---|---|---|
| Kininogen-1 | IASFSQNCDIYPGK | 38 |
| | TVGSDTFYSFK | 37 |
| Vitamin D-binding protein | SCESNSPFPVHPGTAECCTK | 49 |
| Antithrombin-III | TSDQIHFFFAK | 8 |
| Complement C4-A/B | GLEEELQFSLGSK | 24 |
| Protein AMBP | ETLLQDFR | 43 |
| Inter-alpha-trypsin inhibitor heavy chain H4 | ILDDLSPR | 36 |
| Vitronectin | FEDGVLDPDYPR | 51 |
| | DVWGIEGPIDAAFTR | 50 |
| Haptoglobin | TEGDGVYTLNNEK | 51 | from the subject wherein the level of the protein or peptide is used to provide a characterisation of and/or a prognosis for the prostate cancer.

In a further aspect the invention provides a method for characterising and/or prognosing prostate cancer in a subject comprising:
measuring the level of at least one protein from list A or at least one peptide thereof in a sample from the subject in order to identify the presence or absence of cells characteristic of a particular characterisation of and/or a prognosis for the prostate cancer wherein the determined presence or absence of the cells is used to provide a characterisation of and/or a prognosis for the prostate cancer.

In yet a further aspect the invention provides a computing device for characterising and/or prognosing prostate cancer in a subject comprising:
a computer program arranged to characterise and/or provide a prognosis for prostate cancer based on the level of at least one protein from list A or at least one peptide thereof in a sample from the subject and
a display for providing an output of the characterisation and/or prognosis for the prostate cancer.

By characterisation is meant classification and evaluation of the prostate cancer. Prognosis refers to predicting the likely outcome of the prostate cancer for the subject.

In certain embodiments the characterisation of and/or prognosis for the prostate cancer comprises, consists essentially of or consists of determining the grade and/or stage of the prostate cancer.

Grade refers to a score in the Gleason system. Stage refers to stage I, II, III or IV prostate cancer, as defined by the National Cancer Institute at the National Institutes of Health. A stage I prostate cancer is only in the prostate. If the Gleason score and PSA level are known, the Gleason score is 6 or less, and the PSA level is under 10. A stage II prostate cancer is more advanced or a higher grade than Stage I, but the tumour does not extend beyond the prostate. A stage III prostate cancer extends beyond the prostate. The tumour may have invaded a seminal vesicle, but cancer cells have not spread to lymph nodes. A stage IV prostate cancer may have invaded the bladder, rectum, or nearby structures (beyond the seminal vesicles). It may have spread to lymph nodes, bones, or other parts of the body.

An important characterisation is whether or not the cancer is still confined to the prostate. This is directly relevant to prognosis for the subject. Patients with organ confined prostate cancer can be cured through radical prostatectomy and radiation. Hormone therapy is often administered to patients with locally advanced (defined as extracapsular extension but no evidence of nodal or distant metastatic spread) and metastatic prostate cancer. It is not uncommon for patients diagnosed with low grade and organ confined prostate cancer to be subsequently revealed to have high grade and extra-capsular extension after their prostate gland is removed by surgery. Hence there is a need for better biomarkers for grade and stage of disease.

Thus, in certain embodiments the characterisation of and/or prognosis for the prostate cancer comprises, consists essentially of or consists of determining the presence or absence of extra-capsular extension or metastases.

Extracapsular extension refers to extension of the prostate cancer cells into and possibly through the prostate capsule (the outer lining of the prostate gland). The cancer cells may extend through parts of one or both lobes of the gland.

Metastasis, or metastatic disease, is the spread of a cancer from one organ or part to another non-adjacent organ or part. The new occurrences of disease thus generated are referred to as metastases.

The Gleason system is used to grade prostate tumours with a score from 2 to 10, where a Gleason score of 10 indicates the most abnormalities. Cancers with a higher Gleason score are more aggressive and have a worse prognosis. The system is based on how the prostate cancer tissue appears under a microscope and indicates how likely it is that a tumour will spread. A low Gleason score means the cancer tissue is similar to normal prostate tissue and the tumour is less likely to spread; a high Gleason score means the cancer tissue is very different from normal and the tumour is more likely to spread. Gleason scores are calculated by adding the score of the most common grade (primary grade pattern) and the second most common grade (secondary grade pattern) of the cancer cells. Where more than two grades are observed the primary grade is added to the worst observable grade to arrive at the Gleason score. Grades are assigned using the 2005 (amended in 2009) International Society of Urological Pathology (ISUP) Consensus Conference on Gleason Grading of Prostatic Carcinoma.

In certain embodiments the characterisation of and/or prognosis for the prostate cancer comprises, consists essentially of or consists of determining whether the prostate cancer is Gleason score 6 or 7.

For Gleason Score 7, a Gleason 4+3 is a more aggressive cancer than a Gleason 3+4.

In certain embodiments the characterisation of and/or prognosis for the prostate cancer comprises, consists essentially of or consists of determining whether the prostate cancer is Gleason score 3+4 or 4+3.

Characterisation of and/or prognosis for the prostate cancer may also comprise, consist essentially of or consist of predicting biochemical recurrence and/or determining whether the prostate cancer is aggressive and/or determining whether the prostate cancer has spread to the lymph nodes.

By biochemical recurrence is meant a rise in the level of PSA in a subject after treatment for prostate cancer. Biochemical recurrence may indicate that the prostate cancer has not been treated effectively or has recurred.

Aggressive refers to a prostate cancer that is fast growing, more likely to spread, more likely to recur and/or shows resistance to treatment.

List A lists the proteins identified by the inventors where the level of the protein can be used to provide a characterisation and/or a prognosis for prostate cancer. The level of at least one peptide from at least one protein from list A may also be used to provide a characterisation and/or a prognosis for prostate cancer. In certain embodiments the peptide may be from 8 to 25 amino acids in length. More preferably, the at least one peptide comprises, consists essentially of or consists of the amino acid sequence of any of SEQ ID Nos 1 to 52.

One peptide may correspond to more than one protein or to a single protein.

In certain embodiments the level of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 proteins from list A or at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 or 52 peptides of SEQ ID Nos 1 to 52 are measured.

List B is a sub-list of proteins from list A. In certain embodiments a method is provided for characterising and/or prognosing prostate cancer comprising measuring the level of at least 1, 2, 3, 4, 5, 6, 7, 8, 9, 10, 11, 12, 13 or 14 proteins from list B or at least one peptide thereof in a sample from the subject wherein the level of the protein or peptide is used to provide a characterisation of and/or a prognosis for the prostate cancer. More preferably, the level of at least 1, 2, 3, 4, 5, 6, 7, 8, 9, 10, 11, 12, 13, 14, 15 or 16 peptides of list B is measured. The proteins in list B are differentially expressed between non-ECE and ECE samples. In specific embodiments the characterisation of and/or prognosis for the prostate cancer comprises, consists essentially of or consists of determining the presence or absence of ECE.

List C is a sub-list of proteins from list A. In certain embodiments a method is provided for characterising and/or prognosing prostate cancer comprising measuring the level of at least 1, 2, 3, 4, 5, 6, 7, 8 or 9 proteins from list C or at least one peptide thereof in a sample from the subject wherein the level of the protein or peptide is used to provide a characterisation of and/or a prognosis for the prostate cancer. More preferably, the level of at least 1, 2, 3, 4, 5, 6, 7, 8, 9, or 10 peptides of list C is measured. The proteins in list C are differentially expressed between Gleason score 6 and 7 samples. In specific embodiments the characterisation of and/or prognosis for the prostate cancer comprises, consists essentially of or consists of determining whether the prostate cancer is Gleason score 6 or 7.

In specific embodiments the method comprises measuring the level of each protein from list A or at least one peptide from each protein. Preferably, the method comprises measuring the level of each peptide of SEQ ID Nos 1 to 52.

The level of the at least one protein or peptide in the sample from the subject may be analysed using a statistical model. In specific embodiments where the level of at least 2 proteins or peptides are measured the proteins or peptides may be weighted. An overall score may be calculated and used to provide a characterisation of and/or prognosis for the prostate cancer.

In further embodiments the method comprises comparing the level of the at least one protein or peptide to at least one reference value or to one or more control samples. The level of the at least one protein or peptide may be compared to the level of the same protein or peptide from one or more control samples. In certain embodiments the control samples are from one or more subjects with and/or without prostate cancer. In certain embodiments the control samples are from one or more subjects with and/or without extra-capsular extension of prostate cancer. In further embodiments the one or more control samples are from one or more subjects with Gleason score 6 and/or Gleason score 7 prostate cancer. In further embodiments the one or more control samples are from one or more subjects with Gleason score 3+4 and/or Gleason score 4+3 prostate cancer. The level of the at least one protein or peptide in the sample from the subject and the level of the same protein or peptide from the one or more characterized control samples may be analysed using a statistical model. The statistical model may be partial least square discriminant analysis or any other suitable statistical model available to one skilled in the art.

The reference value may be a threshold level of at least one protein or peptide set by determining the level or levels in a range of samples from subjects with and without the particular condition to be detected (as detailed above). In certain embodiments the samples are from one or more subjects with and/or without prostate cancer. In certain embodiments the samples are from one or more subjects with and/or without extra-capsular extension of prostate cancer. In further embodiments the one or more samples are from one or more subjects with Gleason score 6 and/or Gleason score 7 prostate cancer. In further embodiments the one or more samples are from one or more subjects with Gleason score 3+4 and/or Gleason score 4+3 prostate cancer. Suitable methods for setting a threshold are well known to those skilled in the art. The threshold may be mathematically derived from a training set of patient data. The score threshold thus separates the test samples according to presence or absence of the particular condition. The interpretation of this quantity, i.e. the cut-off threshold may be derived in a development or training phase from a set of patients with known outcome. The threshold may therefore be fixed prior to performance of the claimed methods from training data by methods known to those skilled in the art.

In Tables 3 and 4 a fold change of above 1 indicates an increase in the level of the protein or peptide. A fold change below 1 indicates a decrease in the level of the protein or peptide. Thus, in certain embodiments, if the protein is Zinc alpha-2-glycoprotein or Apolipoprotein A-I or the peptide is SEQ ID No. 52 or 10 the level of the protein or peptide is increased if extra-capsular extension of prostate cancer is present relative to if extra-capsular extension of prostate cancer is absent or if the protein is Kininogen-1, Hemopexin, Serum albumin, Serotransferrin, Complement C3, Inter-alpha-trypsin inhibitor heavy chain H4, Antithrombin-III, Complement C4-A/B, Pigment epithelium-derived factor, Haptoglobin-related protein or Plasminogen or the peptide is SEQ ID No. 38, 37, 33, 46, 45, 44, 21, 36, 35, 8, 24, 41, 31 or 1 the level of the protein or peptide is decreased if extra-capsular extension of prostate cancer is present relative to if extra-capsular extension of prostate cancer is absent.

In specific embodiments, if the protein is Zinc alpha-2-glycoprotein or the peptide is SEQ ID No. 52 the level of the protein or peptide is increased by a factor of at least 1.34, more particularly 1.34 to 1.54, more particularly 1.44, if extra-capsular extension of prostate cancer is present relative to if extra-capsular extension of prostate cancer is absent.

In specific embodiments, if the protein is Apolipoprotein A-I or the peptide is SEQ ID No. 10 the level of the protein or peptide is increased by a factor of at least 1.08, more particularly 1.08 to 1.28, more particularly 1.18, if extra-capsular extension of prostate cancer is present relative to if extra-capsular extension of prostate cancer is absent.

In specific embodiments if the protein is Kininogen-1 or the peptide is SEQ ID No. 38 or SEQ ID No. 37 the level of the protein or peptide is decreased by a factor of at least 0.59, more particularly 0.59 to 0.89, more particularly 0.69 to 0.79, if extra-capsular extension of prostate cancer is present relative to if extra-capsular extension of prostate cancer is absent.

In specific embodiments if the protein is Hemopexin or the peptide is SEQ ID No. 33 the level of the protein or peptide is decreased by a factor of at least 0.74, more particularly 0.74 to 0.94, more particularly 0.84, if extra-capsular extension of prostate cancer is present relative to if extra-capsular extension of prostate cancer is absent.

In specific embodiments if the protein is Serum albumin or the peptide is SEQ ID No. 46 or SEQ ID No. 45 the level of the protein or peptide is decreased by a factor of at least 0.68, more particularly 0.68 to 0.94, more particularly 0.78 to 0.84, if extra-capsular extension of prostate cancer is present relative to if extra-capsular extension of prostate cancer is absent.

In specific embodiments if the protein is Serotransferrin or the peptide is SEQ ID No. 44 the level of the protein or peptide is decreased by a factor of at least 0.70, more particularly 0.70 to 0.90, more particularly 0.80, if extra-capsular extension of prostate cancer is present relative to if extra-capsular extension of prostate cancer is absent.

In specific embodiments if the protein is Complement C3 or the peptide is SEQ ID No. 21 the level of the protein or peptide is decreased by a factor of at least 0.70, more particularly 0.70 to 0.90, more particularly 0.80, if extra-capsular extension of prostate cancer is present relative to if extra-capsular extension of prostate cancer is absent.

In specific embodiments if the protein is Inter-alpha-trypsin inhibitor heavy chain H4 or the peptide is SEQ ID No. 36 or SEQ ID No. 35 the level of the protein or peptide is decreased by a factor of at least 0.69, more particularly 0.69 to 0.93, more particularly 0.79 to 0.83, if extra-capsular extension of prostate cancer is present relative to if extra-capsular extension of prostate cancer is absent.

In specific embodiments if the protein is Antithrombin-III or the peptide is SEQ ID No. 8 the level of the protein or peptide is decreased by a factor of at least 0.73, more particularly 0.73 to 0.93, more particularly 0.83, if extra-capsular extension of prostate cancer is present relative to if extra-capsular extension of prostate cancer is absent.

In specific embodiments if the protein is Complement C4-NB or the peptide is SEQ ID No. 24 the level of the protein or peptide is decreased by a factor of at least 0.72, more particularly 0.72 to 0.92, more particularly 0.82, if extra-capsular extension of prostate cancer is present relative to if extra-capsular extension of prostate cancer is absent.

In specific embodiments if the protein is Pigment epithelium-derived factor or the peptide is SEQ ID No. 41 the level of the protein or peptide is decreased by a factor of at least 0.69, more particularly 0.69 to 0.89, more particularly 0.79, if extra-capsular extension of prostate cancer is present relative to if extra-capsular extension of prostate cancer is absent.

In specific embodiments if the protein is Haptoglobin-related protein or the peptide is SEQ ID No. 31 the level of the protein or peptide is decreased by a factor of at least 0.66, more particularly 0.66 to 0.86, more particularly 0.76, if extra-capsular extension of prostate cancer is present relative to if extra-capsular extension of prostate cancer is absent.

In specific embodiments if the protein is Plasminogen or the peptide is SEQ ID No. 1 the level of the protein or peptide is decreased by a factor of at least 0.71, more particularly 0.71 to 0.91, more particularly 0.81, if extra-capsular extension of prostate cancer is present relative to if extra-capsular extension of prostate cancer is absent.

In further embodiments if the protein is Haptoglobin or the peptide is SEQ ID No. 51 the level of the protein or peptide is increased if the prostate cancer is Gleason score 7 relative to Gleason score 6 or if the protein is Kininogen-1, Vitamin D-binding protein, Antithrombin-III, Complement C4-NB, Protein AMBP, Inter-alpha-trypsin inhibitor heavy chain H4 or Vitronectin or the peptide is SEQ ID NO 38, 37, 49, 8, 24, 43, 36, 51 or 50 the level of the protein or peptide is decreased if the prostate cancer is Gleason score 7 relative to Gleason score 6.

In specific embodiments if the protein is Haptoglobin or the peptide is SEQ ID No. 51 the level of the protein or peptide is increased by a factor of at least 1.39, more particularly 1.39 to 1.59, more particularly 1.49, if the prostate cancer is Gleason score 7 relative to Gleason score 6.

In specific embodiments if the protein is Kininogen-1 or the peptide is SEQ ID No. 38 or SEQ ID No. 37 the level of the protein or peptide is decreased by a factor of at least 0.57, more particularly 0.57 to 0.86, more particularly 0.67 to 0.76, if the prostate cancer is Gleason score 7 relative to Gleason score 6.

In specific embodiments if the protein is Vitamin D-binding protein or the peptide is SEQ ID No. 49 the level of the protein or peptide is decreased by a factor of at least 0.63, more particularly 0.63 to 0.83, more particularly 0.73, if the prostate cancer is Gleason score 7 relative to Gleason score 6.

In specific embodiments if the protein is Antithrombin-III or the peptide is SEQ ID No. 8 the level of the protein or peptide is decreased by a factor of at least 0.68, more particularly 0.68 to 0.88, more particularly 0.78, if the prostate cancer is Gleason score 7 relative to Gleason score 6.

In specific embodiments if the protein is Complement C4-NB or the peptide is SEQ ID No. 24 the level of the protein or peptide is decreased by a factor of at least 0.61, more particularly 0.61 to 0.81, more particularly 0.71, if the prostate cancer is Gleason score 7 relative to Gleason score 6.

In specific embodiments if the protein is Protein AMBP or the peptide is SEQ ID No. 43 the level of the protein or peptide is decreased by a factor of at least 0.70, more particularly 0.70 to 0.90, more particularly 0.80, if the prostate cancer is Gleason score 7 relative to Gleason score 6.

In specific embodiments if the protein is Inter-alpha-trypsin inhibitor heavy chain H4 or the peptide is SEQ ID No. 36 the level of the protein or peptide is decreased by a factor of at least 0.72, more particularly 0.72 to 0.92, more particularly 0.82, if the prostate cancer is Gleason score 7 relative to Gleason score 6.

In specific embodiments if the protein is Vitronectin or the peptide is SEQ ID No. 51 or SEQ ID No. 50 the level of the protein or peptide is decreased by a factor of at least 0.66, more particularly 0.66 to 0.88, more particularly 0.76 to 0.78, if the prostate cancer is Gleason score 7 relative to Gleason score 6.

In a further aspect, the present invention relates to a method for determining the presence or absence of extra-capsular extension of prostate cancer in a subject comprising:
measuring the level of at least one protein from list A or a peptide thereof in a sample from the subject wherein the level of the protein or peptide is used to determine the presence or absence of extra-capsular extension of prostate cancer.

In certain embodiments the at least one peptide comprises, consists essentially of or consists of the amino acid sequence of any of SEQ ID Nos 1 to 52.

In yet a further aspect, the present invention relates to a method for determining whether a prostate cancer of a subject is Gleason score 6 or Gleason score 7 comprising:
measuring the level of at least one protein from list A or a peptide thereof in a sample from the subject wherein the level of the protein or peptide is used to determine whether the prostate cancer is Gleason score 6 or 7.

In certain embodiments the at least one peptide comprises, consists essentially of or consists of the amino acid sequence of any of SEQ ID Nos 1 to 52.

The present invention further relates to a method for selecting a treatment for prostate cancer in a subject comprising:
(a) measuring the level of at least one protein from list A or at least one peptide thereof in a sample from the subject wherein the level of the protein or peptide is used to provide a characterisation of and/or a prognosis for the prostate cancer and
(b) selecting a treatment appropriate to the characterisation of and/or prognosis for the prostate cancer.

In certain embodiments the at least one peptide comprises, consists essentially of or consists of the amino acid sequence of any of SEQ ID Nos 1 to 52. In further embodiments the characterisation of or prognosis for the prostate cancer comprises, consists essentially of or consists of determining the presence or absence of extra-capsular extension. In yet further embodiments the characterisation of or prognosis for the prostate cancer comprises, consists essentially of or consists of determining whether the prostate cancer is Gleason score 6 or 7 or determining whether the prostate cancer is Gleason score 3+4 or 4+3.

In certain embodiments if extra-capsular extension is absent the patient is treated with radical prostatectomy and radiation. If extra-capsular extension is present the patient may be treated with hormone therapy and/or radiation. Therefore, the methods of the invention may facilitate patient management and improve treatment. Costs may be lowered for patient care by ensuring therapies are not pursued in circumstances where they are unlikely to be unsuccessful.

The present invention further relates to a method of treating prostate cancer comprising treatment of a subject with radical prostatectomy and radiation or hormone therapy wherein the subject is selected for treatment on the basis of a method as described herein.

In a further aspect, the present invention relates to a hormone therapeutic agent for use in treating prostate cancer in a subject wherein the subject is selected for treatment on the basis of a method as described herein.

In yet a further aspect, the present invention relates to a method of treating prostate cancer comprising treatment of a subject with hormone therapy wherein the subject has an increased level of Zinc alpha-2-glycoprotein or Apolipoprotein A-I or the peptides SEQ ID No. 52 or 10 or a decreased level of Kininogen-1, Hemopexin, Serum albumin, Serotransferrin, Complement C3, Inter-alpha-trypsin inhibitor heavy chain H4, Antithrombin-III, Complement C4-A/B, Pigment epithelium-derived factor, Haptoglobin-related protein or Plasminogen or the peptides SEQ ID No. 38, 37, 33, 46, 45, 44, 21, 36, 35, 8, 24, 41, 31 or 1.

The invention also relates to a hormone therapeutic agent for use in treating prostate cancer in a subject wherein the subject has an increased level of Zinc alpha-2-glycoprotein or Apolipoprotein A-I or the peptides SEQ ID No. 52 or 10 or a decreased level of Kininogen-1, Hemopexin, Serum albumin, Serotransferrin, Complement C3, Inter-alpha-trypsin inhibitor heavy chain H4, Antithrombin-III, Complement C4-A/B, Pigment epithelium-derived factor, Haptoglobin-related protein or Plasminogen or the peptides SEQ ID No. 38, 37, 33, 46, 45, 44, 21, 36, 35, 8, 24, 41, 31 or 1.

By hormone therapy is meant a form of treatment which reduces the level and/or activity of selected hormones, in particular testosterone. A hormone therapeutic agent is an agent for carrying out hormone therapy. The hormones may promote tumour growth and/or metastasis. The hormone therapy may comprise a luteinizing hormone blocker, such as goserelin (also called Zoladex), buserelin, leuprorelin (also called Prostap), histrelin (Vantas) and triptorelin (also called Decapeptyl). The hormone therapy may comprise a gonadotrophin release hormone (GnRH) blocker such as degarelix (Firmagon) or an anti-androgen such as flutamide (also called Drogenil) and bicalutamide (also called Casodex). The hormone therapy may comprise a drug that blocks the formation of testosterone. In specific embodiments the hormone therapy may be bicalutamide and/or abiraterone. Hormone therapy may be given before and/or during radiation treatment. Hormone therapy may be intermittent (for several i.e. 1, 2 or 3 months at a time with intervals in between) or continuous.

The invention also relates to an antibody that binds specifically to a peptide that comprises, consists essentially of or consists of the amino acid sequence of any of SEQ ID Nos 1 to 52.

The antibody may be of monoclonal or polyclonal origin. Fragments and derivative antibodies may also be utilised, to include without limitation Fab fragments, ScFv, single domain antibodies, nanoantibodies, heavy chain antibodies, aptamers etc. which retain peptide-specific binding function and these are included in the definition of "antibody".

Such antibodies are useful in the methods of the invention. They may be used to measure the level of a particular protein or peptide.

Methods for generating specific antibodies are known to those skilled in the art. Antibodies may be of human or non-human origin (e.g. rodent, such as rat or mouse) and be humanized etc. according to known techniques (Jones et al., Nature (1986) May 29-June 4; 321(6069):522-5; Roguska et al., Protein Engineering, 1996, 9(10):895-904; and Studnicka et al., Humanizing Mouse Antibody Frameworks While Preserving 3-D Structure. Protein Engineering, 1994, Vol. 7, pg 805).

According to a further aspect of the invention there is provided a kit for characterising and/or prognosing prostate cancer in a subject comprising one or more antibodies that binds specifically to a peptide that comprises, consists essentially of or consists of the amino acid sequence of any of SEQ ID Nos 1 to 52.

The invention also relates to a peptide of 25 amino acids or fewer for use as a biomarker, wherein the peptide comprises, consists essentially of or consists of the amino acid sequence of any of SEQ ID Nos 1 to 52. In certain embodiments the peptide is more than 5, 6, 7, or 8 amino acids in length. The level of the peptide in a sample may be used to provide a characterisation of and/or a prognosis for prostate cancer.

In specific embodiments the level of the peptide in a sample is used to determine the presence or absence of extra-capsular extension of prostate cancer and/or to determine whether a prostate cancer is Gleason score 6 or 7 and/or to determine whether a prostate cancer is Gleason score 3+4 or 4+3.

The present invention further relates to a panel of at least two prostate cancer biomarkers comprising at least one protein from list A or a peptide thereof. In certain embodiments the at least one peptide comprises, consists essentially of or consists of the amino acid sequence of any of SEQ ID Nos 1 to 52.

In a further aspect, the present invention relates to use of at least one protein from list A or a peptide thereof for characterising and/or prognosing a prostate cancer in a subject, wherein the level of the protein or peptide in a sample from the subject is used to characterise and/or provide a prognosis for the prostate cancer.

The invention also relates to use of at least one protein from list A or list B or a peptide thereof for determining the presence or absence of extra-capsular extension of prostate cancer in a subject, wherein the level of the protein or peptide is used to determine the presence or absence of extra-capsular extension of prostate cancer.

In yet a further aspect, the present invention relates to use of at least one protein from list A or list C or a peptide thereof for determining whether a prostate cancer of a subject is Gleason score 6 or Gleason score 7, wherein the level of the protein or peptide is used to determine whether the prostate cancer is Gleason score 6 or 7.

In certain embodiments the at least one protein or peptide is chemically modified. In specific embodiments the chemical modification is phosphorylation and/or glycosylation.

According to all aspects of the invention patient samples may be of any suitable form. The sample may comprise, consist essentially of or consist of a biological fluid or a fluid or lysate generated from a biological material. In certain embodiments the biological fluid comprises, consists essentially of or consists of a blood sample. In specific embodiments the blood sample is a plasma sample. In further embodiments the blood sample is a serum sample. In further embodiments the biological fluid comprises, consists essentially of or consists of seminal fluid. In further embodiments the biological fluid comprises, consists essentially of or consists of urine, optionally wherein the urine is obtained before or after a prostatic massage. In certain embodiments the biological material comprises, consists essentially of or consists of prostate tissue.

The level of protein or peptide may be measured by any suitable method. In certain embodiments the level of the at least one protein or peptide is measured by mass spectrometry, immunoassay and/or radioassay. Measurement by immunoassay may comprise, consist essentially of or consist of immunoblotting or enzyme-linked immunosorbent assay (ELISA).

In certain embodiments measurement by mass spectrometry comprises, consists essentially of or consists of multiple reaction monitoring—MRM. MRM is a method used in tandem mass spectrometry in which an ion of a particular mass is selected in the first stage of a tandem mass spectrometer and an ion product of a fragmentation reaction of the precursor ion is selected in the second mass spectrometer stage for detection. For proteins, following ionization, a peptide precursor is first isolated to obtain a substantial ion population of mostly the intended species. This population is then fragmented to yield product ions whose signal abundances are indicative of the abundance of the peptide in the sample.

In specific embodiments only proteotypic peptides are used for MRM. By proteotypic peptide is meant peptides which are indicative of the presence of a particular protein. They may have no missed cleavage, be 8 to 25 amino acids long, be outside the N-terminal 25 amino acids of the protein, with no potential ragged ends and/or peptides that are unique mapping tryptic peptides.

The methods of the invention may be performed in vitro in certain embodiments.

In a further aspect, the present invention relates to a system or device for performing any of the methods described above. The system or device may be specifically adapted or configured to perform the methods of the invention, for example to calculate the level of at least one protein in the sample and determine the characterisation or prognosis of the prostate cancer. Thus, the system or device may contain suitable software to make the relevant calculations and determinations. The system or device may comprise an apparatus for measuring the level of at least one protein, together with a processor and a storage medium comprising a computer application that, when executed by the processor, is configured to cause the system or device to perform the steps of the claimed method using the apparatus. Thus, the methods of the invention may be automated methods in some embodiments. The system or device may perform MRM in some embodiments.

The methods of the invention may further comprise measuring the level of at least one additional protein from list D or at least one peptide thereof in a sample from the subject.

The methods of the invention may alternatively comprise measuring the level of at least one protein from list D or at least one peptide thereof in a sample from the subject. The embodiments described above apply mutatis mutandis to this aspect.

List D—Additional Proteins

| Protein Name | Uniprot Accession No. | Peptide Sequence | SEQ ID No. |
|---|---|---|---|
| Annexin A3 | P12429 | GAGTNEDALIEILTTR | 53 |
|  |  | SDTSGDYEITLLK | 54 |
| Anoctamin-7 | Q6IWH7 | LLDLLVPDIPESVEIK | 55 |
|  |  | QALAENEVLFGTNGTK | 56 |
| Apolipoprotein D | P05090 | NPNLPPETVDSLK | 57 |
|  |  | ADGTVNQIEGEATPVNLTEPAK | 58 |
| Beta-Ala-His dipeptidase | Q96KN2 | EWVAIESDSVQPVPR | 59 |
|  |  | GDGWLTDPYVLTEVDGK | 60 |
| CD5 antigen-like | O43866 | ELGCGAASGTPSGILYEPPAEK | 61 |
|  |  | EATLQDCPSGPWGK | 62 |
| Chromogranin-A | P10645 | EDSLEAGLPLQVR | 63 |
| Coagulation factor XII | P00748 | TTLSGAPCQPWASEATYR | 64 |
| Coagulation factor XIII B chain | P05160 | QGYDLSPLTPLSELSVQCNR | 65 |
|  |  | QEEQTTCTTEGWSPEPR | 66 |
| Complement C1q subcomponent subunit B | P02746 | QGYDLSPLTPLSELSVQCNR | 67 |
| Complement C1r subcomponent | P00736 | GFLAYYQAVDLDECASR | 68 |
| Complement factor H | P08603 | LGYVTADGETSGSITCGK | 69 |
|  |  | EQVQSCGPPPELLNGNVK | 70 |
| Complement factor H-related protein 1 | Q03591 | STDTSCVNPPTVQNAHILSR | 71 |
| Complement factor H-related protein 2 | P36980 | ITCAEEGWSPTPK | 72 |
|  |  | TGDIVEFVCK | 73 |
| Endoglin | P17813 | LPDTPQGLLGEAR | 74 |
|  |  | GNCVSLLSPSPEGDPR | 75 |
| Galectin-3-binding protein | Q08380 | SDLAVPSELALLK | 76 |
|  |  | AAIPSALDTNSSK | 77 |
| Glutathione peroxidase 3 | P22352 | QEPGENSEILPTLK | 78 |
|  |  | NSCPPTSELLGTSDR | 79 |
| Histatin 3 | P15516 | Not determined |  |
| Ig kappa chain C region | P01834 | VDNALQSGNSQESVTEQDSK | 80 |
|  |  | DSTYSLSSTLTLSK | 81 |
| Ig mu chain C region | P01871 | NVPLPVIAELPPK | 82 |
| Insulin-like growth factor 1 receptor | P08069 | VAGLESLGDLFPNLTVIR | 83 |
|  |  | AENGPGPGVLVLR | 84 |
| Insulin-like growth factor IA | P01343 | Not determined |  |
| Insulin-like growth factor-binding protein 7 | Q16270 | GTCEQGPSIVTPPK | 85 |
|  |  | GEGEPCGGGAGR | 86 |
| Interleukin-6 | P05231 | NLDAITTPDPTTNASLLTK | 87 |
|  |  | EALAENNLNLPK | 88 |
| Kallikrein-11 | Q9UBX7 | ILQLILLALATGLVGGETR | 89 |
|  |  | TATESFPHPGFNNSLPNK | 90 |
| Monocyte differentiation antigen CD14 | P08571 | AFPALTSLDLSDNPGLGER | 91 |
|  |  | STLSVGVSGTLVLLQGAR | 92 |
| Prostate and breast cancer overexpressed gene 1 protein | Q9GZY1 | LPGILAPETVLLPFCYK | 93 |

-continued

| Protein Name | Uniprot Accession No. | Peptide Sequence | SEQ ID No. |
| --- | --- | --- | --- |
| Prostate-specific antigen | P07288 | LSEPAELTDAVK | 94 |
|  |  | HSQPWQVLVASR | 95 |
| Prostatic acid phosphatase | P15309 | SPIDTFPTDPIK | 96 |
|  |  | LSGLHGQDLFGIWSK | 97 |
| Proteasome subunit beta type-6 | P28072 | LAAIAESGVER | 98 |
|  |  | FAVATLPPA | 99 |
| Transforming growth factor beta-1 | P01137 | EAVPEPVLLSR | 100 |
|  |  | VAGESAEPEPEPEADYYAK | 101 |
| Vascular endothelial growth factor A | P15692 | SWSVYVGAR | 102 |
| Vascular endothelial growth factor D | O43915 | ETCVEVASELGK | 103 |
|  |  | QLFEISVPLTSVPELVPVK | 104 |

List D lists proteins identified by the inventors where the level of the protein can be used to provide a characterisation and/or a prognosis for prostate cancer. The level of at least one peptide from at least one protein from list D may also be used to provide a characterisation and/or a prognosis for prostate cancer. In certain embodiments the peptide may be from 8 to 25 amino acids in length. More preferably, the at least one peptide comprises, consists essentially of or consists of the amino acid sequence of any of SEQ ID Nos 53 to 104.

One peptide may correspond to more than one protein or to a single protein.

In certain embodiments the level of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32 proteins from list D or at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 peptides of SEQ ID Nos 53 to 104 are measured.

EXAMPLES

Figure 1:
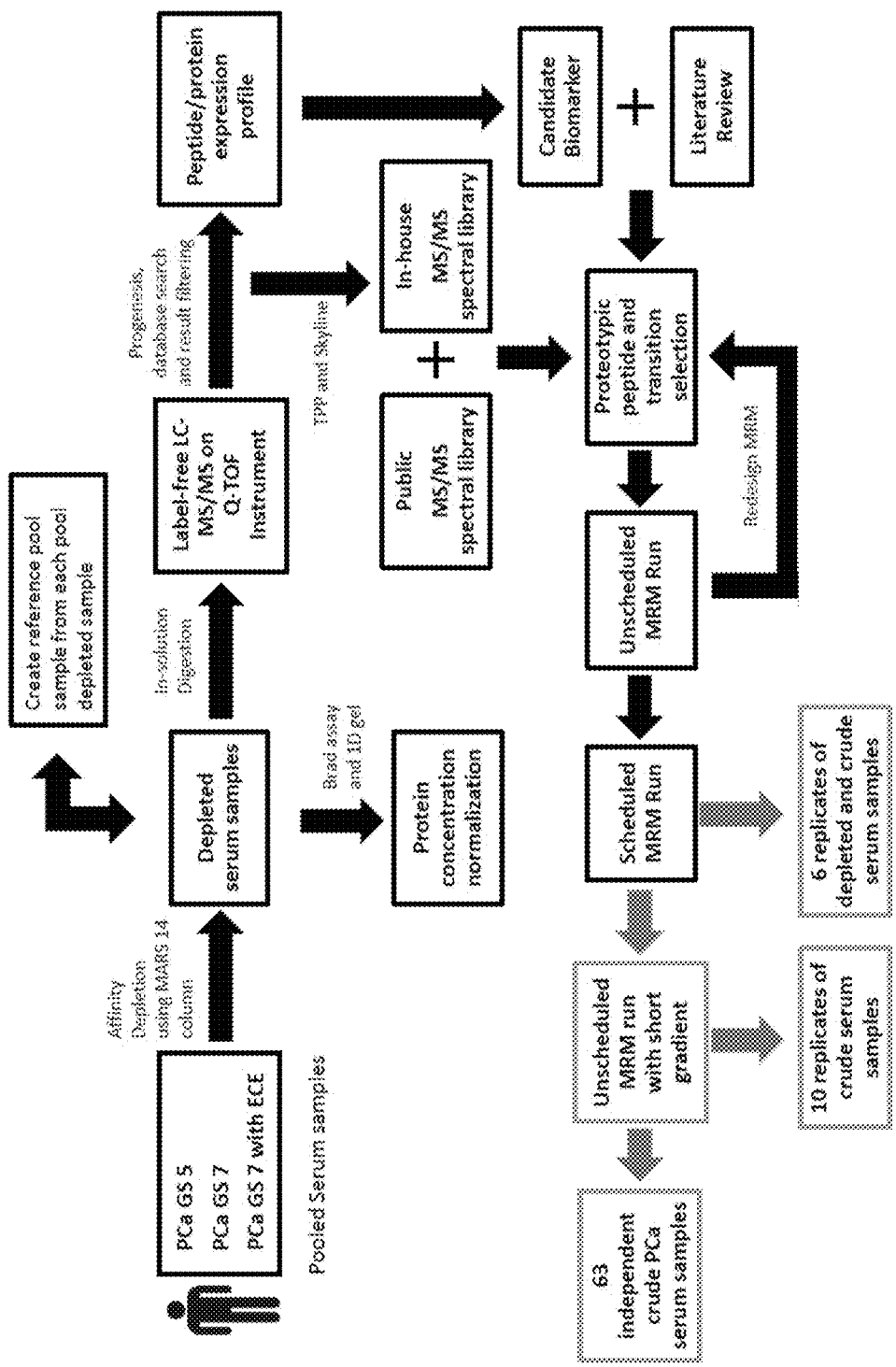
FIG. 1. Diagram of the label-free and MRM workflow

The present invention will be further understood by reference to the following experimental examples.

Label-Free LC-MS and MRM Development for Discovery and Verification of Biomarkers for Prostate Cancer Abbreviations:

AA, amino acid; AUC, area under the curve; CV, coefficient of variation; ECE, extra-capsular extension; IAA, iodoacetamide; MRM, multiple reaction monitoring; OC, organ confined; PCa, prostate cancer; PCA, principal component analysis; PLS-DA, partial least square discriminant analysis; PSA, prostate specific antigen; PTP, proteotypic peptide; ROC, Receiver operating characteristic; RT, retention time; TFE, trifluoroethanol; TPP, Trans-Proteomic Pipeline; VTDB, vitamin D-binding protein.

SUMMARY

Prostate cancer (PCa) is the most common cancer diagnosed and the second most common cause of cancer-related deaths in men in western countries. Currently, serum prostate-specific antigen (PSA) is the only biomarker widely used in the diagnosis and management of patients with PCa. However, it lacks specificity. Thus, additional biomarkers are urgently needed for clinical management of PCa. High-throughput LC-MS is increasingly amenable to profile biological samples for potential protein markers for disease and it has the potential to reveal protein biomarkers that may have clinical utility. In this current study, label-free LC-MS/MS was applied to the pooled serum samples from PCa patients with different Gleason score and stages after affinity depletion. 51 and 24 peptides were found to be significantly differentially expressed (p<0.05) with at least 2 fold changes between patients with Gleason score 5 and 7, and patients with organ confined and extra capsular extension, respectively. A multiple reaction monitoring assay (MRM) was developed to verify the changes of 32 proteins identified from the label-free LC-MS/MS experiment and literature review. High reducibility of this MRM assay was observed on 6 replicates each of affinity depleted (CV=6.51%) and crude (CV=7%) serum samples. The initial verification of the 32 proteins on 63 independent PCa serum samples has demonstrated the robustness of MRM as a quantitative method for measuring peptides/proteins in large number of crude serum samples. The 32 protein signature measured by MRM has shown highly favorable predictive performance for PCa grading (AUC=0.789) and staging (AUC=0.824). With careful validation on large patient cohort, this signature has the potential to improve diagnosis and help to identify the most beneficial treatment plan for PCa patients.

Introduction

PCa remains the most common form of male cancer in the US and Europe, accounting for more than 20% of all newly diagnosed cancer cases in men (1, 2). The morality rate was reported to be approximately 9% of all cancer caused death (1, 2). With early diagnosis, most of men affected by PCa can be treated effectively through surgery or radiation therapy to prevent the tumour from further growth and metastasis (3). The accurate determination of the Gleason score and the stages of PCa is of great significance in the clinical decision making for the selection of the most appropriate patient management strategy. However, due to the heterogeneity of the disease and randomness of the biopsy, most often the biopsy does not provide accurate representation about the extent and progression of the disease preoperatively. In addition, the stages of the disease (whether it is organ confined or locally advanced disease) is often unclear before treatment, which information is essential for selection of the most appropriate treatment options. Patients with organ confined PCa can be cured through radical prostatectomy and radiation, or hormone therapy will be given to treat patients with locally advanced and metastatic PCa. It is not uncommon for patients diagnosed with low grade and organ confined (OC) PCa to be subsequently up graded and up staged revealed to have high grade and extra-capsular extension (ECE) after their prostate gland was removed by surgery. It is clear that we need better biomarkers for grade and stage of disease.

With recent advances in technology, proteomics holds great promise for the delivery of biomarkers through high throughput proteomics profiling analysis of biological samples. A "tissue to serum" approach has become increasingly popular in the cancer biomarker discovery field (4-7). Differentially expressed proteins (most commonly glycoproteins or secreted proteins) are first identified from cell lines, animal models or clinical tissue samples and then these biomarkers are measured in the serum/plasma to evaluate if they also can be used as serum biomarkers. However these changes do not always correlate well with the expression patterns in serum. A more direct approach is to identify serum biomarkers through profiling the serum proteome. Compared with tissue samples, serum provides an easily accessible sample, which can be sampled over time for disease monitoring. However, serum also presents well known analytical challenges most notably the large dynamic range of protein concentration (>10 orders of magnitude) (8), which means fractionation methods are required to remove the most abundant proteins. Notwithstanding these limitations it is apparent that biomarkers discovered in serum have greater potential for 'transfer' to clinical assays.

A number of studies have reported serum biomarker discovery for PCa using different proteomics profiling methods and these studies have predominately used SELDI-TOF and 2D gel electrophoresis (9-14). Advances in these proteomics techniques particularly LC-MS/MS has promised a better proteome coverage and higher sensitivity in detecting novel biomarkers for PCa diagnosis and prognosis. A label-free LC-MS/MS approach has been increasingly popular for proteomics studies dealing with clinical samples (15-19). Furthermore, the use of the targeted MS based method, MRM provides a relatively straightforward approach for quantitative validation of protein biomarkers thanks to its high sensitivity (attomolar level), dynamic range ($10^5$) and the ease with which protein measurements can be multiplexed.

Here, we took the approach of coupling label-free LC-MS/MS with MRM for the identification and verification of serum proteins biomarkers which can predict Gleason score and stages of PCa. As outlined in FIG. 1, the pooled serum samples from 3 groups of patients: low grade disease (Gleason score 5), high grade disease (Gleason score 7) and high grade with ECE were depleted, tryptic digested and subjected to label-free LC-MS/MS. An MRM assay was developed for 32 proteins which were identified from label-free LC-MS/MS experiment and literature review. The developed MRM was tested for reproducibility on both depleted and crude serum samples. Subsequently, this MRM assay was applied to an independent 63 crude serum samples from PCa patients for the verification stage of the study. The MRM result showed that this 32 protein signature can provide highly favorable prediction accuracies in classifying different Gleason scores and stages.

Materials and Method
Reagents and Chemicals

All reagents were American Chemical Society (ACS) grade or higher. All solvents used, including water, were LC-MS grade.

Serum Sample Collection

Blood samples from patients with PCa were collected between 2005 to 2008 as part of the Prostate Cancer Research Consortium BioResource following standard operating procedures with informed consent from patients with PCa before undergoing radical prostatectomy. Ethical approval was granted by the relevant hospital sites within the consortium. Anticoagulant free tubes were used to collect blood samples which were then transported to the laboratory for processing within 30 min. Blood samples were allowed to clot for 30 min and then centrifuged at 3,000 rpm at 20° C. for 15 min. The supernatants were collected, aliquoted and stored at −80° C. until the time of analysis. Each serum sample underwent no more than 3 freeze/thaw cycles prior to analysis. The clinical information summary of the patient cohorts used in the label-free LC-MS/MS (n=30) and MRM (n=63) are listed in Table 1. The detailed clinical information can be found in the Supplementary Table 1 and 2.

Generation of Pooled Samples

Ten patient samples were collected for each of the three groups: PCa patients with post operation Gleason score 5, Gleason score 7 and Gleason score 7 with ECE. 12 μL from each control/patients was used to generate a pool of 120 μL for each group.

TABLE 1

Clinical information summary of patient cohort used in the label-free LC-MS/MS and MRM experiment.

| | Patient | No. | Age (years) | PSA (ng/ml) | ECE | SVI | LNI |
|---|---|---|---|---|---|---|---|
| Label-free LC-MS/MS | GS 5 | 10 | 61 (4.81) | 9.42 (5.26) | 0 | 0 | 0 |
| | GS 7 | 10 | 62.7 (5.48) | 7.9 (2.96) | 0 | 0 | 0 |
| | GS 7 with ECE | 10 | 60.7 (6.91) | 7.86 (2.76) | 10 | 0 | 1 |

| | Patient | No. | Age (years) | PSA (ng/ml) | GS 3 + 3 | GS 3 + 4 | GS 4 + 3 |
|---|---|---|---|---|---|---|---|
| MRM | GS 6 | 21 | 59.4 (5.49) | 7.69 (2.80) | 21 | 0 | 0 |
| | GS 7 | 22 | 60.6 (6.78) | 7.9 (4.61) | 0 | 11 | 11 |
| | GS 7 with ECE | 20 | 63.65 (6.12) | 8.95 (4.91) | 0 | 9 | 11 |

GS: Gleason score, SVI: seminal vesicle invasion, LNI: lymph node involvement.

Affinity Depletion of Serum Samples

A MARS Hu-14 column (Agilent Technologies, catalog number: 5188-6557) was used with a Vision HPLC system (Applied Biosciences) to deplete the fourteen most abundant serum proteins (albumin, transferrin, haptoglobin, IgG, IgA, α1-antitrypsin, fibrinogen, α2-macroglobulin, α1-acid glycoprotein, complement C3, IgM, apolipoprotein AI, apolipoprotein AII, and transthyretin) following the manufacturer's instructions. 20 μL of pooled serum from each sample group was diluted 1 in 5 with commercially available Agilent Buffer A (Agilent Technologies) and underwent high speed centrifugation at 15000 g for 5 min to remove particulate matter and lipids. A total of 80 μL of the diluted sample was then injected onto a MARS Hu-14 column and the low abundant protein fractions were eluted from the column with Agilent Buffer B (Agilent Technologies). The column was washed extensively in between individual sample depletion. The depletion of all the samples was carried out in a random order. Depletions were repeated six times for each pooled sample in order to obtain a sufficient amount of protein: the fractions containing the low abundant proteins were concentrated and desalted by centrifugation using spin columns (Agilent Spin Concentrators for Proteins, Agilent Technologies). The concentrated low abundant proteins was collected from the filters and immediately stored at −80° C. Protein concentration was determined using Bradford assay. A reference pool sample was prepared by pooling equal amount of protein together from the three pooled depleted protein samples.

Bradford Protein Assay

The protein concentration of the serum samples was determined using the method described by Bradford (20). Bovine serum albumin standards were prepared at concentrations of 0, 0.05, 0.1, 0.2, 0.4, 0.6, 0.8, and 1 µg/µl through serial dilution from the 2 µg/µl stock solution (Sigma-Aldrich). The depleted serum samples were used directly and crude serum samples were diluted at 1:120 with $ddH_2O$. 25 µl of the sample or standard were added to 1.25 ml of Bradford reagent, and then vortexed and transferred to a cuvette. The absorbance at 595 nm was measured after 5 minutes. A standard curve was constructed using the absorbance from the known concentration of BSA standards and the protein concentration of each sample was calculated based on the absorbance reading from the standard curved and adjusted for the sample dilution factor.

1D SDS PAGE

The depletion efficiencies and the Bradford quantification were examined by running SDS PAGE gel. An aliquot containing 4 µg of proteins of interest for each samples was re-suspended in SDS sample buffer (Novex) and run on 1D SDS PAGE (12% Tris-HCl). Proteins were visualized using a modified colloidal Coomassie blue stain (21).

Trypsin In-Solution Digestion

Serum proteins in-solution digestion was carried out using sequencing grade modified porcine trypsin (Promega). Samples were subjected to reduction (10 mM DTT, 50 mM $NH_4HCO_3$ and 50% trifluoroethanol (TFE), 30 min, and room temperature) and alkylation (20 mM iodoacetamide (IAA), 30 min, room temperature, dark) to eliminate disulphide bridging at cysteine residues and prevent it from reforming. DTT was added in to a final concentration of 10 mM to quench excess IAA. Buffer exchange was carried out using spin concentrators (Agilent) and washed three times with 3 mL of 5% (v/v) TFE, 50 mM $NH_4HCO_3$. Sample was recovered from the spin concentrator and the concentrator was washed twice with 50 µl of 5% TFE in 50 mM $NH_4HCO_3$. 20 µg trypsin was resuspended in 20 µL of 50 mM $NH_4HCO_3$ and appropriate amount of trypsin was added to the samples and incubated at 37° C. for 18 hours at 500 rpm in a thermomixer (trypsin to substrate ratio=1: 100). The digested samples were put on SpeedVac to dryness and resuspended in buffer A (3% ACN, 0.1% formic acid) and stored in aliquots of 100 µL at a concentration of 1 µg/µL at −80° C.

Label-Free LC-MS/MS Experiment and Data Analysis

Samples were reconstituted with buffer A (3% acetonitrile, 0.1% formic acid) to generate a final concentration of 1 µg/µl. 4 µl samples were separated using a 90 min gradient on a 150 mm×75 um C18 nano-LC chip (Agilent) coupled to an Agilent 6520 Q-TOF mass spectrometer. Gradient elution was conducted using buffer A and buffer B (90% acetonitrile, 0.1% formic acid), using a flow rate of 300 nL/min with the following program: 0-40% B 0-90 min, 40-90% B 90-100 min, hold 90% B 100-115 min, 90-0% B 118 min, followed by column reconditioning for 15 min. Each pooled sample was run in triplicate and the order of the protein samples was randomized. A standard peptide mixture was run before and after the experimental samples to ensure instrument performance was satisfactory. Technical variance was determined by running reference pool replicates before, in-between and after sample runs, which resulted in 10 replicates being analysed in total. The samples were run in the "auto MS/MS" mode with 2 MS/MS spectra acquired for each MS scan. At the end of experiment three identification runs were performed using reference pool sample in the "auto MS/MS" mode with 10 MS/MS spectra acquired for each MS scan to aid in protein identification.

Data collected from the Agilent Q-TOF mass spectrometer was converted into mzXML using ProteoWizard (22). The mzXML files were imported to a commercial software Progenesis LC-MS version 2.5 (Nonlinear Dynamics). The mass and charge ratio was plotted against retention time (RT) and a reference pool sample was selected as the reference run such that the rest of samples could be aligned to it. Manual alignment was undertaken for each sample as a 'seeding' guide for automatic alignment by assigning 15 to 20 alignment vectors to each sample as suggested by user manual (Nonlinear Dynamics). Feature detection and automatic alignment were then performed automatically by Progenesis LC-MS. Filters were applied to select only ion features with m/z values from 299.000 to 2702.952, RT (min) from 13 to 102, charge state from 2 to 8 and features with at least three isotopes. Finally, the identified features and the corresponding MS/MS spectra of these features (including sample and the identification runs were exported from Progenesis for database search. The MS/MS spectra were searched using Mascot (v 2.2.0, Matrix Sciences) against UniprotKB/Swiss-Prot database (v 57.1). The search parameters were: enzyme: semiTrypsin, allow up to 1 missed cleavage, taxonomy: Homo sapiens, fixed modifications: carbamidomethylated cysteine, variable modification: oxidized methionine, and mass tolerances of precursor ions: 20 ppm, product ions: 0.1 Da.

The search results were imported into Progenesis LC-MS and peptide sequences/identifications were mapped across different samples and three identification runs. The normalized feature abundances were exported and subsequent analysis was carried out using R. None unique mapping peptides (peptide mapping to more than one protein) were removed from the search results. To assess the reproducibility of the identified peptide features, the coefficient of variation (CV) of each feature from the reference pool samples was calculated and plotted against the normalized feature abundances.

MRM Development, Experiment and Data Analysis

The search results were filtered using PeptideProphet within Trans-Proteomic Pipeline (TPP) and a minimum probability threshold of 0.9 was given to achieve error rate of 2.2% and sensitivity of 0.642 (23, 24). MS/MS spectral library of the PCa serum label-free LC-MS/MS data was built using Skyline (25). A previous in-house human plasma MS/MS library and a few public MS/MS libraries including PeptideAtlas, NIST and GPM were also used in the MRM method development.

The MRM method design and result analysis was carried out using Skyline (25). Only proteotypic peptides (PTP) were included in the MRM design. PTP in this study was defined as no missed cleavage, 8 to 25 amino acids (AA) long, outside the N-terminal 25 AA, no potential ragged ends, unique mapping tryptic peptide. Peptides with methionine were also excluded in case oxidation could affect peptide quantification. Cysteine was set to have carbamidomethylation modification. The charge states of precursor ions were set to 2 and 3. The product ions were limited to singly charge and only y ions were selected. In order to minimize the potential interference, y ions with m/z close to precursor ion were excluded. Up to 5 peptides with highest MS/MS signal were selected for each protein and up to 8 transitions representing the highest y ion peaks in the MS/MS spectral were selected.

The MRM experiment was performed using an Agilent 6460 QqQ coupled with a 150 mm×75 um C18 nano-LC chip. Peptide samples were reconstituted with buffer A to generate a final concentration of 1 μg/μL and 3 μL was loaded for each sample. A flow rate of 300 nL/min was used. The gradient elution method for the initial MRM development is as follow: 0-40% B 0-90 min, 40-90% B 90-100 min, hold 90% B 100-115 min, 90-0% B 118 min, followed by column reconditioning for 20 min. The resolution at quadrupole 1 (Q1) and quadrupole 3 (Q3) was unit. The collision energy for each transition was calculated using a formula (precursor m/z×0.036-4.8). In the MRM runs, the duty cycle for unscheduled method was maintained around 3 s, the dwell time was set to 20 m seconds and the fragmentor voltage was set to 135V in the positive ion MRM mode. 10 min window was set for each peptide in the scheduled MRM experiment. In the running of 63 individual crude serum samples, a short gradient elution method was used: 0-35% B 0-30 min, 35-95% B 30-35 min, hold 95% B 35-36 min, 95-0% B 38 min, followed by column reconditioning for 15 min. Blank was run in-between each sample and the order of sample running was randomized. A standard peptide mixture was run at the beginning and after every 10 samples during the experiment to ensure the instrument performance.

Statistical Analysis

Student t-test was used to identify differentially expressed peptides in the label-free LC-MS/MS and MRM data. Q-value was calculated as an indication of FDR. PCA plot was generated for the unique mapping peptides expression data from the label-free LC-MS/MS experiment. The prediction performance of the 32 proteins measured by MRM was assessed using partial least square discriminant analysis (PLS-DA) with 200 times bootstrapping. The 4 peptide panel was tested using Random Forests method with 10 fold cross validation. Receiver operating characteristic (ROC) curves were generated and areas under the curve (AUC) values were calculated. A permutation method was used to test whether the AUC values generated are due to random chance. All the statistical analysis was performed in R.

Results

Affinity Depletion

Figure 12:
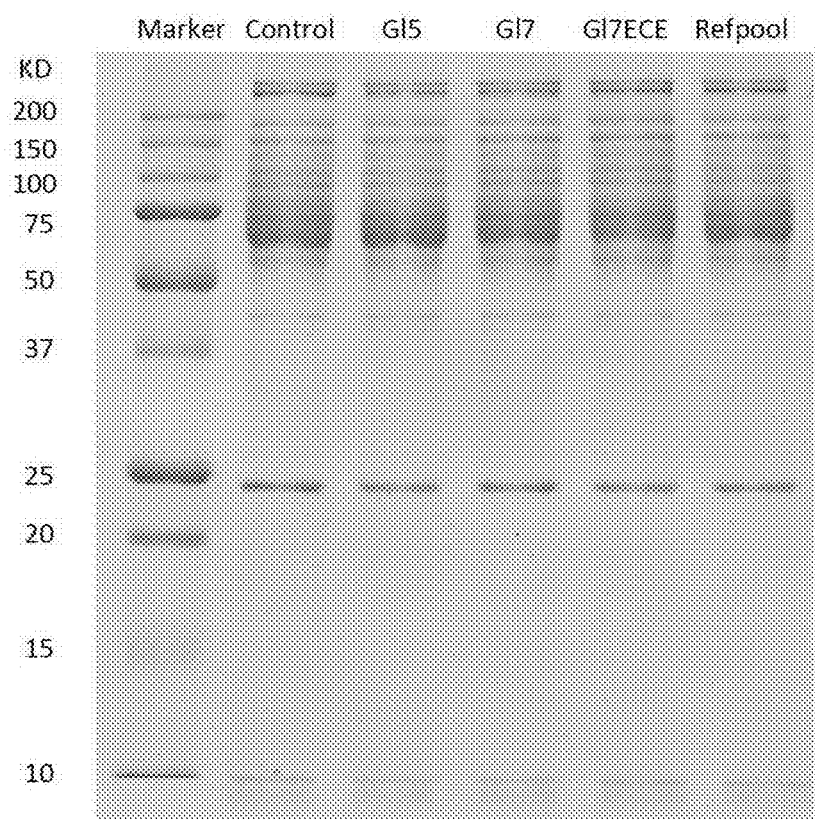

The depletion efficiencies were assessed by running depleted serum samples on 1D SDS PAGE and staining with Coomassie blue (FIG. 12). The depletion efficiencies were consistent across 3 PCa groups and one non-PCa control sample. The staining result from the 1D gel was also used to adjust protein loading for the label-free LC-MS/MS experiment.

LC-MS/MS Data Analysis

Figure 2:
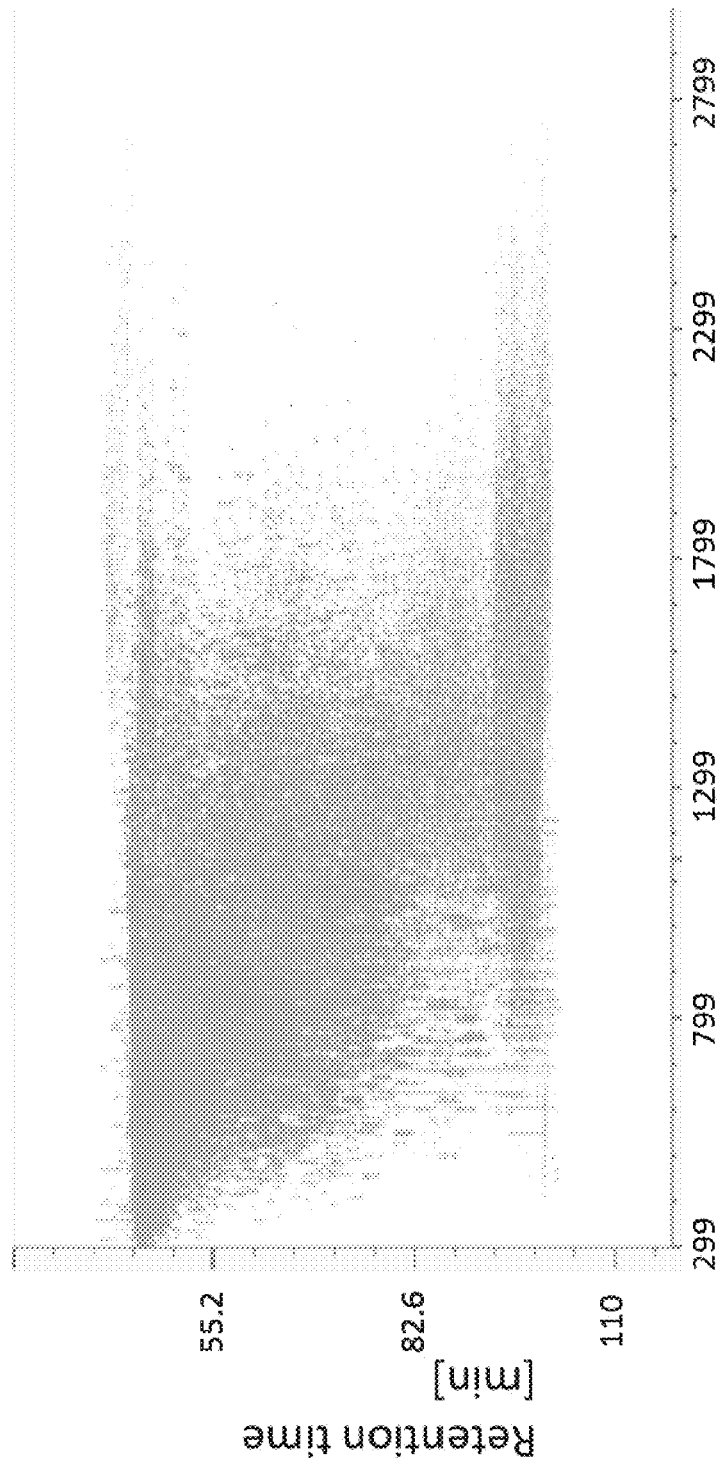
FIG. 2. Plot of m/z versus RT. Filters were applied to select only ion features with m/z values from 299.000 to 2702.952, RT (min) from 13 to 102, charge state from 2 to 8 and features with at least three isotopes.

Spectral alignment was performed in Progenesis LC-MS and the quality of the alignment was assessed manually for each sample run to ensure high quality. After alignment and filtering using Progenesis LC-MS, 91086 features (containing isotopes) were identified as potential peptides. A plot of m/z versus RT can be found in FIG. 2. The extracted ion chromatograph was normalized using total ion count across different samples. Protein/peptides were identified using Mascot search. FDR was calculated as the percentage ratio of number of protein matches from a decoy database ("reverse") and the total number of "forward" protein matches (26). A Mascot search score of 34 was determined to achieve FDR of 3.08% (468/15039). The search results were imported back to Progenesis LC-MS and protein/peptide identification were mapped across different runs. The normalized abundance of the identified peptide features was exported. The aim of the label-free LC-MS/MS experiment was to look for differentially expressed peptides and collect MS/MS data for subsequent validation using MRM. Therefore the identified peptides were then further filtered by excluding peptides with score less than 34 to remove low score peptides within the identified proteins, which resulted in 1391 peptides from 95 proteins. By filtering out none unique mapping peptides, relative quantitative expression data were obtained for 765 peptides from 81 proteins.

Figure 3:
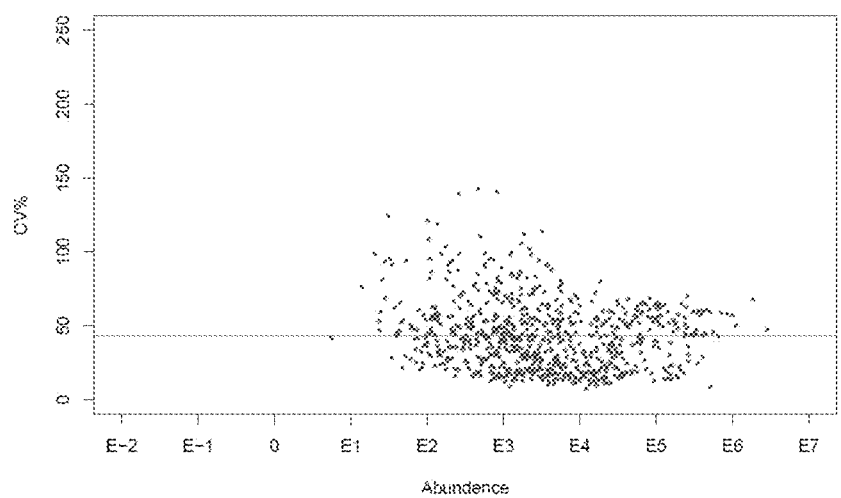
FIG. 3. Plot of unique mapping peptide feature abundance versus CV % in the 10 reference pool samples. The mean CV % was calculated as 43.4%, indicated by the horizontal red line.

In order to measure experiment variations between different sample runs (HPLC variation, sample preprocessing, etc.), 10 reference pool samples were include before, in-between and after the pool patient sample runs. The CV % of the unique mapping peptides from the 10 reference pool samples was plotted against logarithm scaled peptide abundance (FIG. 3). The average level of CV % was 43.4% and lower level of CV % was found to be associated with peptides with higher abundance.

Figure 4:
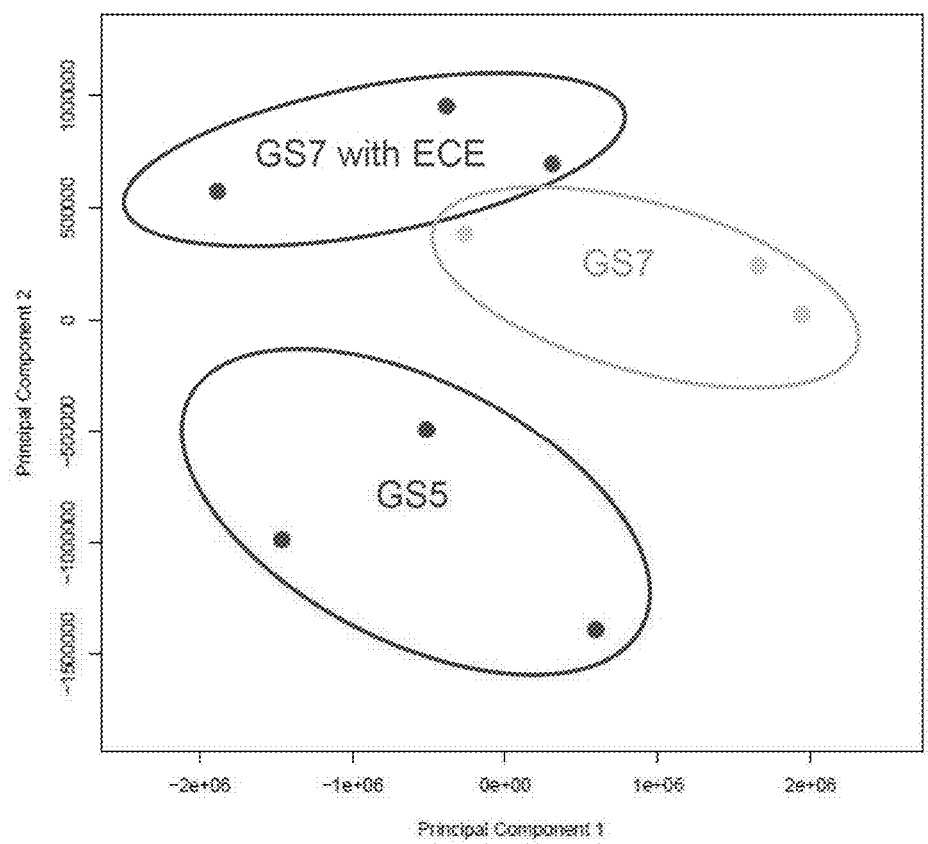
FIG. 4. PCA plot of unique mapping peptides identified from the label-free LC-MS/MS experiment. Blue: Gleason score 5 samples, yellow: Gleason score 7 samples, red: Gleason score 7 with ECE samples.

Principal component analysis (PCA) was applied to the normalized relative abundance data of unique mapping peptides. The first two principal components were plotted in FIG. 4. In the PCA plot, Gleason score 5 were separated from all the Gleason score 7 patients while Gleason score 7 and Gleason score 7 with ECE were close to each other. The technical variation of the LC-MS/MS run was mostly captured by the first principal component and biological variation was more apparent at the second component.

Figure 5A:
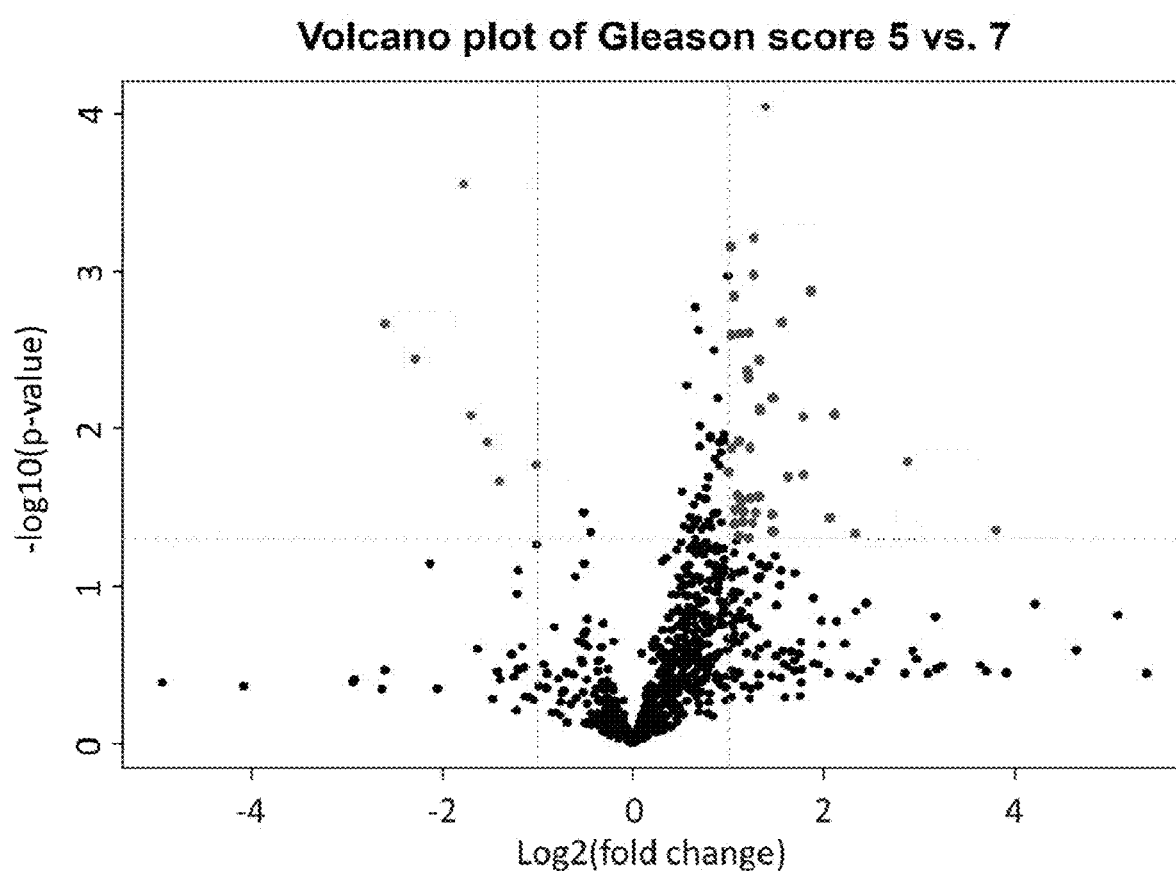
FIG. 5A-B. Volcano plot of unique mapping peptides. A: Gleason score 5 and 7, B: non-ECE and ECE. Red: >2 fold change and p-value<0.05.
Figure 5B:
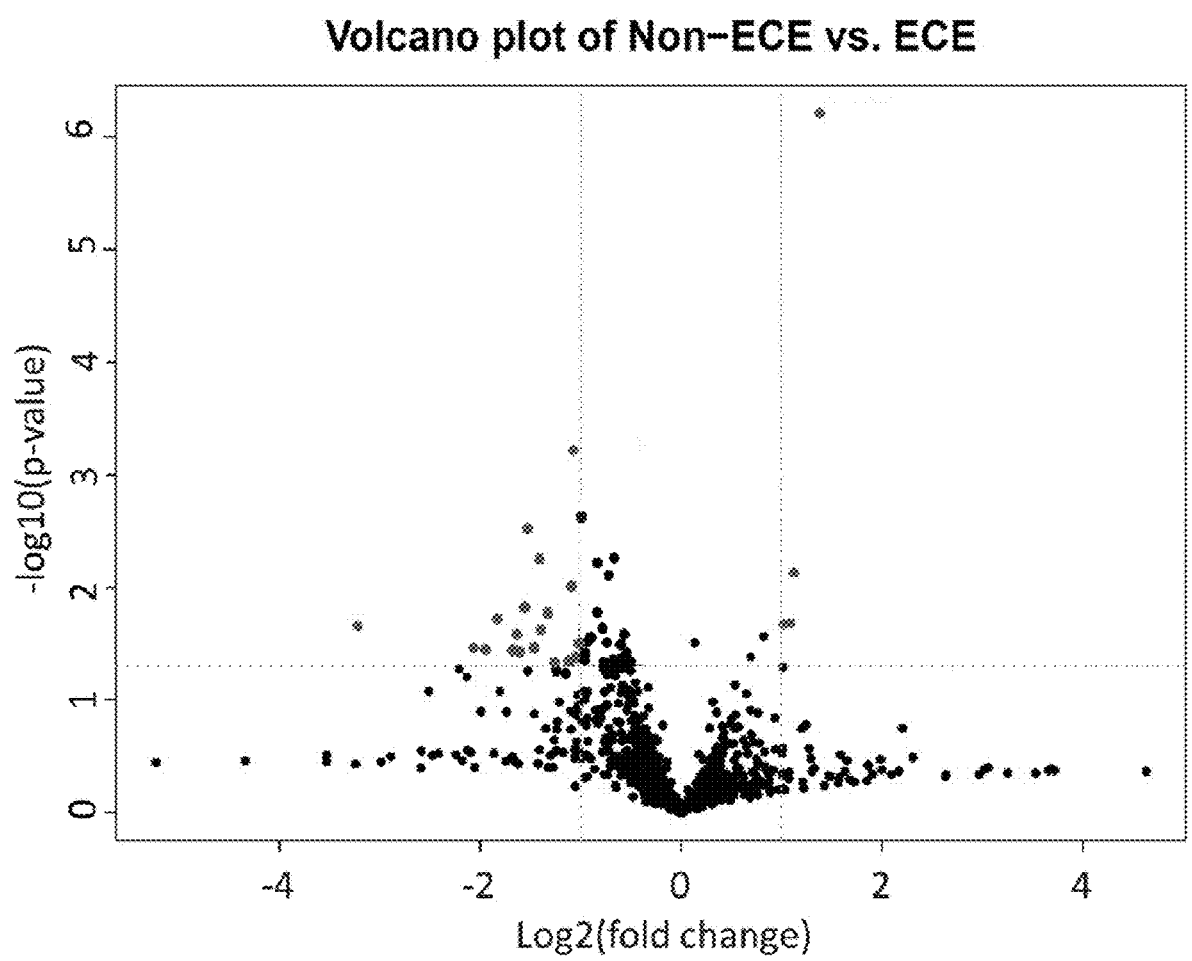

Volcano plot was used to study the differentially expression between different groups. In FIG. 5, the fold change ($\log_2$) were plotted against p-values ($-\log_{10}$) calculated from t-test for all the unique mapping peptides. Peptides with at least 2 fold change and p-value less than 0.05 (t-test) were labeled in red and their corresponding protein names were given on the plot. 51 and 24 peptides were found to pass the thresholds between Gleason score 5 and 7, and between non-ECE and ECE, respectively. The lists of these peptides together with fold change, p-values can be found in the Supplementary Table 3 and 4.

Discrepancies in the changing direction were found between peptides from the same protein. 10 peptides from Apolipoprotein B-100 were identified to be differentially expressed between Gleason score 5 and 7. 9 peptides were found to be up regulated in the Gleason score 7 samples however one peptide (IADFELPTIIVPEQTIEIPSIK) was showing down regulation. Such discrepancies were also found in other proteins. It may be due to the experimental variations, or false positive hit from the database search, or as a result of different PTMs or protein isoforms.

A list of 64 proteins was selected from the protein/peptides biomarkers identified from label-free LC-MS/MS and published literature results for subsequent biomarker verification using MRM. The list are shown in Supplementary Table 5, the reference concentration of the proteins were based on the review published by Hortin et al. (27). Due to the relative small sample size and large variations observed in the label-free LC-MS/MS experiment, only a small number of identified peptides from the label-free LC-MS/MS results were included in this MRM validation list.

MRM Results

Figure 6:
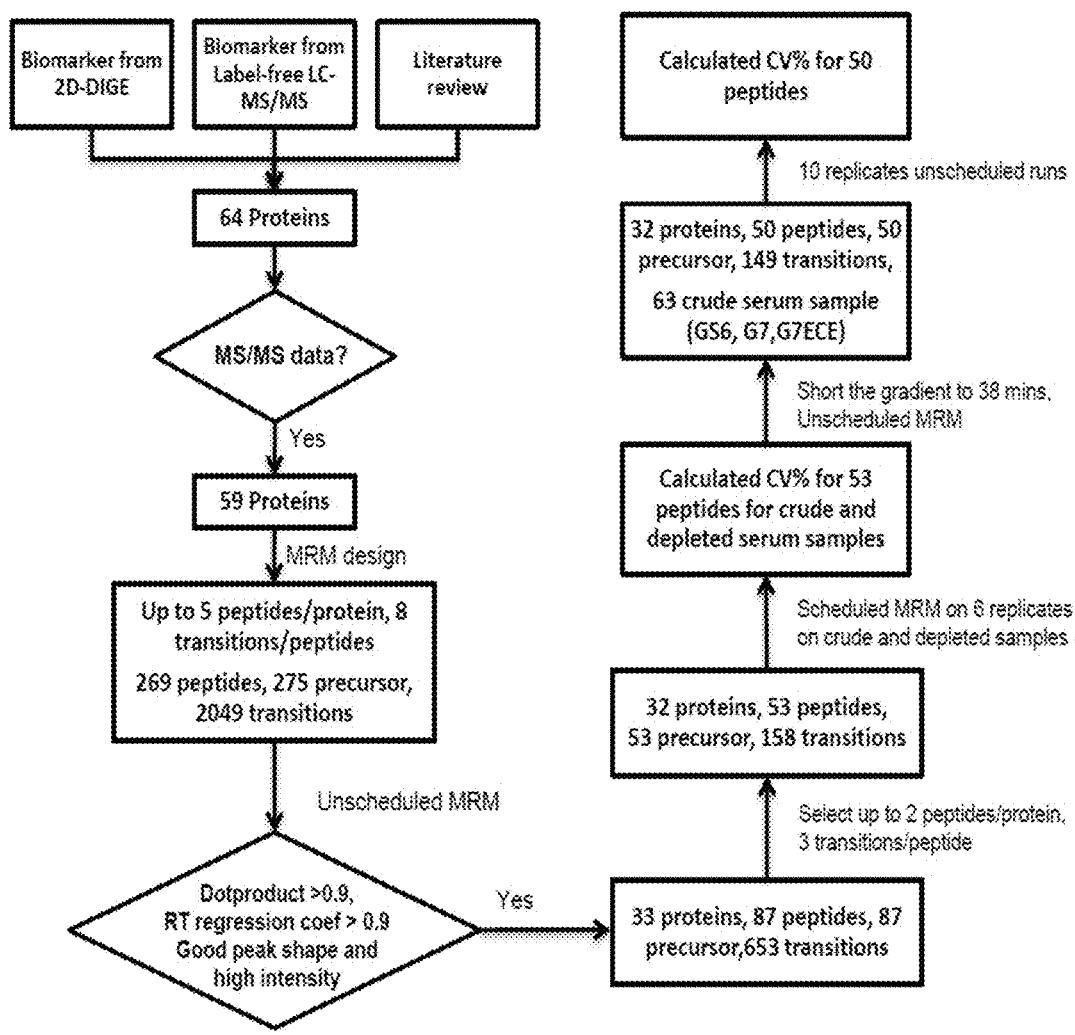
FIG. 6. MRM development process

The initial MRM experiment was designed using Skyline to target the specific peptides of 64 proteins. The process of MRM development was illustrated in FIG. 6. The in-house and public LC-MS/MS data were used for the peptide and transition selection. Among 64 proteins, MS/MS data is available for 59 proteins. Based on the MS/MS spectral libraries, 269 peptides with 275 precursor ions and 2049 transitions from 59 proteins were included in the initial MRM method.

Unscheduled MRM experiments were carried out on depleted reference pool samples. MRM data was imported into Skyline and Savitzky-Golay smoothing was applied to the data. The MRM transition results were verified using peak coelution, peak intensities, dot product (>0.90), and regression coefficient (>0.90) of RT versus hydrophobicity score in Skyline (28), which results in 33 proteins with 87 peptides, 87 precursor ions and 653 transitions.

Figure 13A:
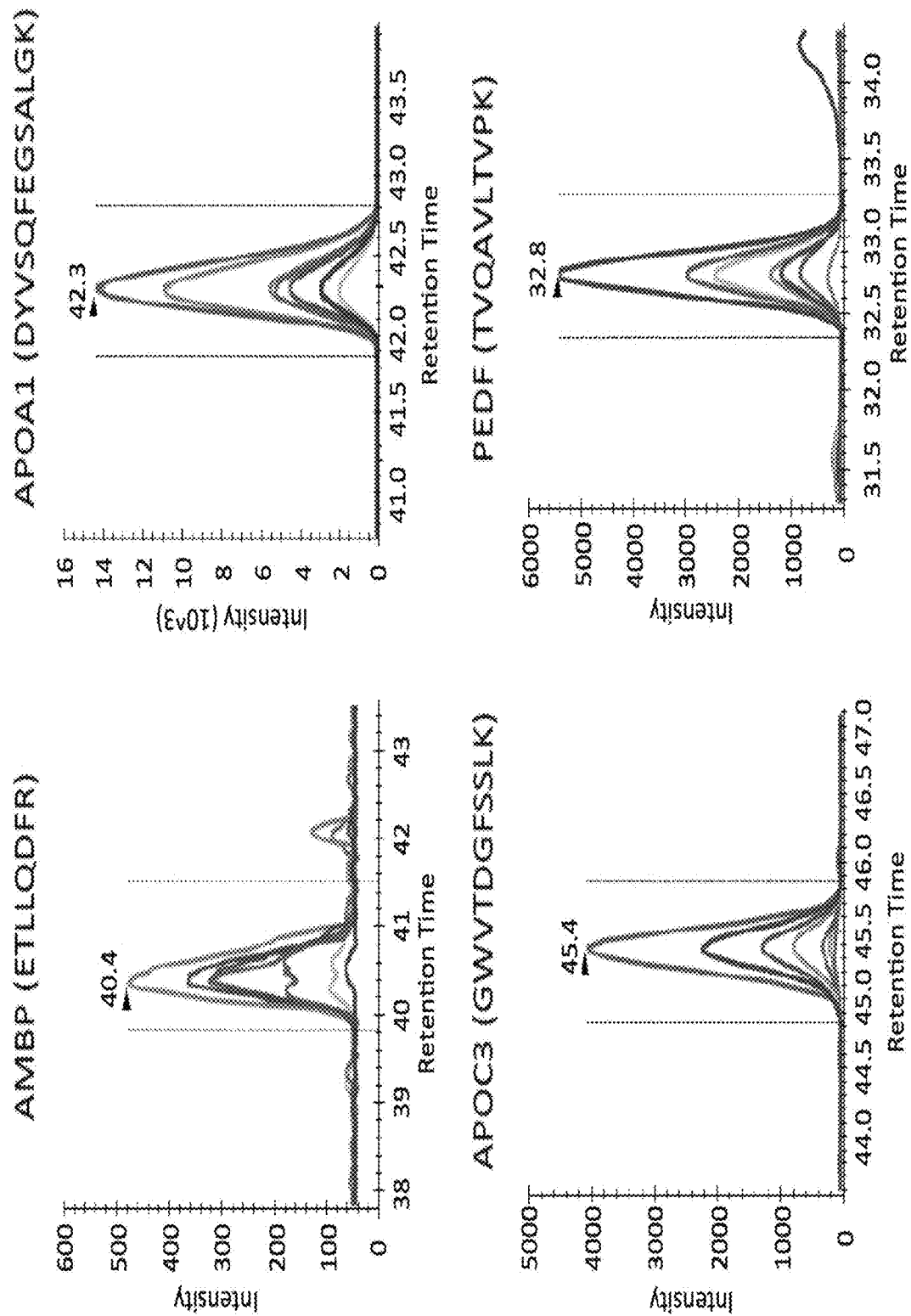
Figure 13B:
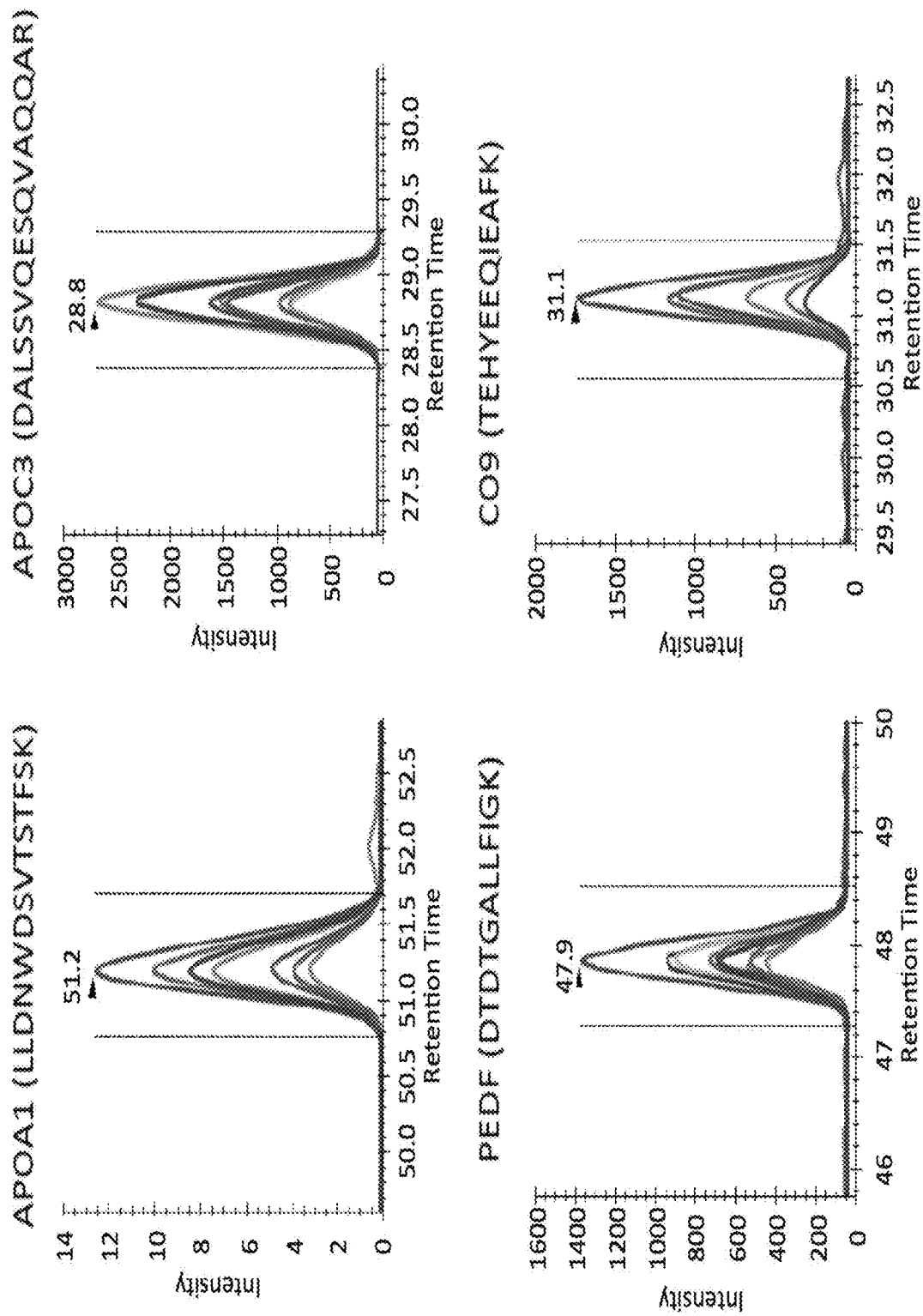
Figure 13C:
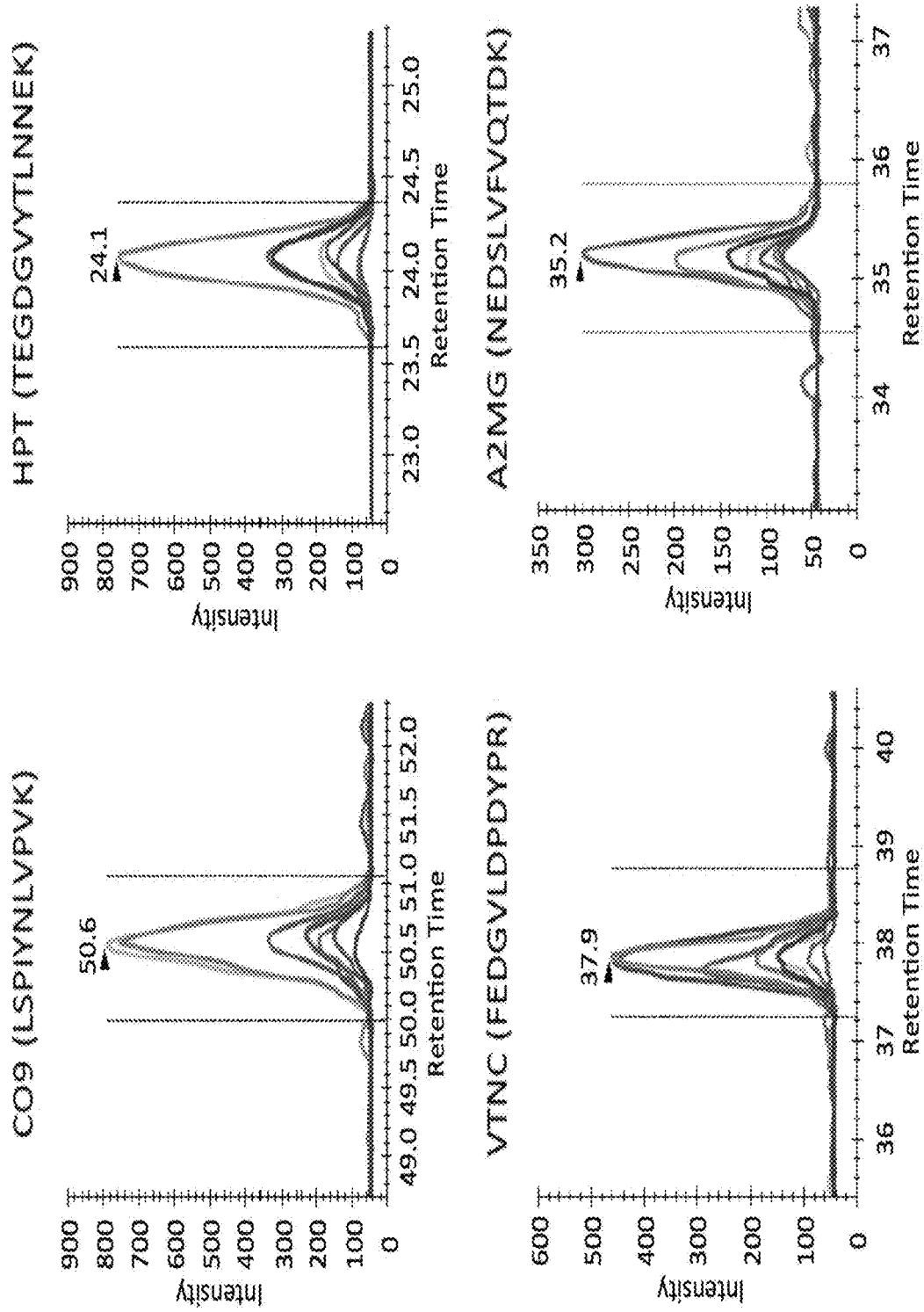
Figure 13D:
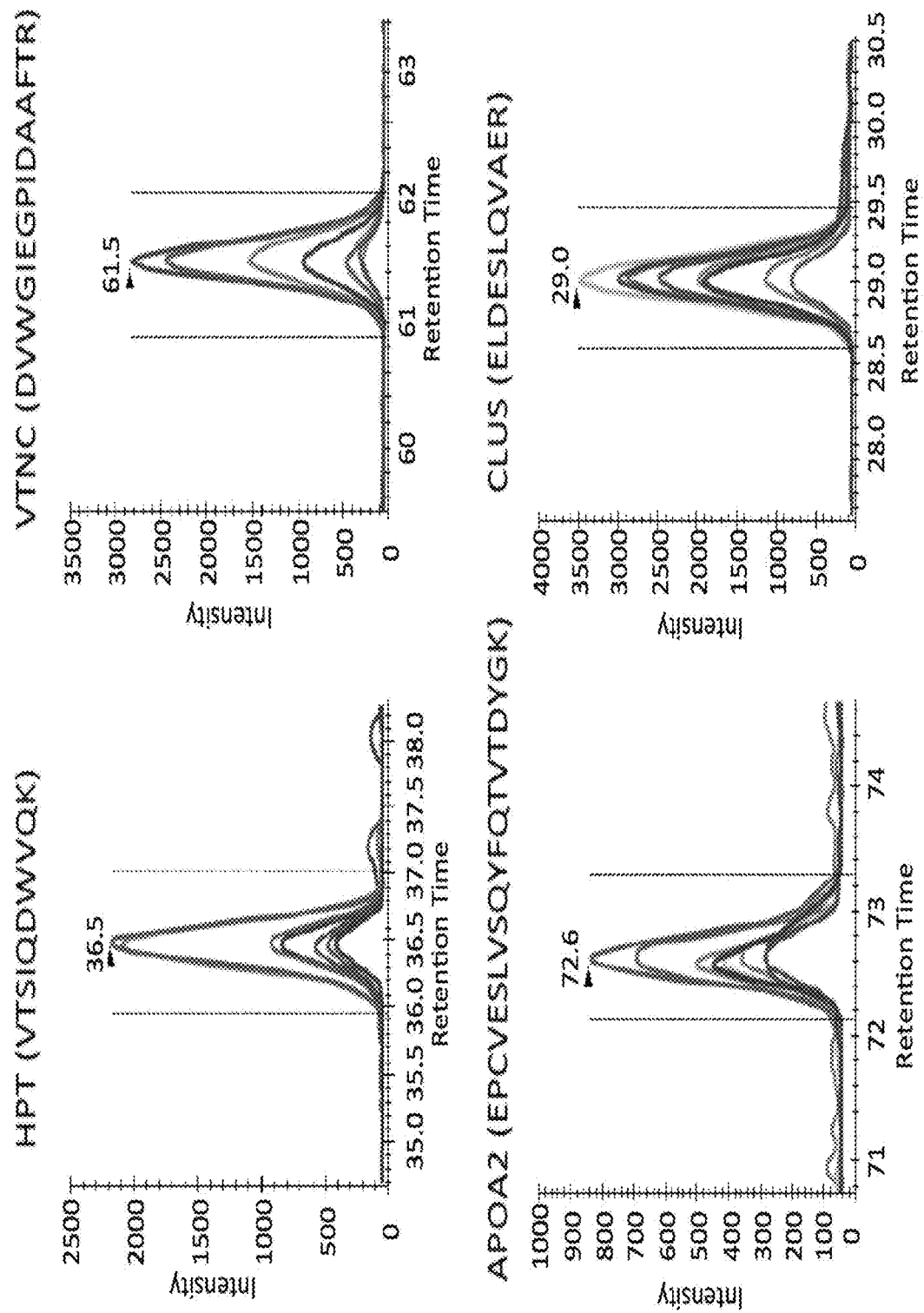
Figure 13E:
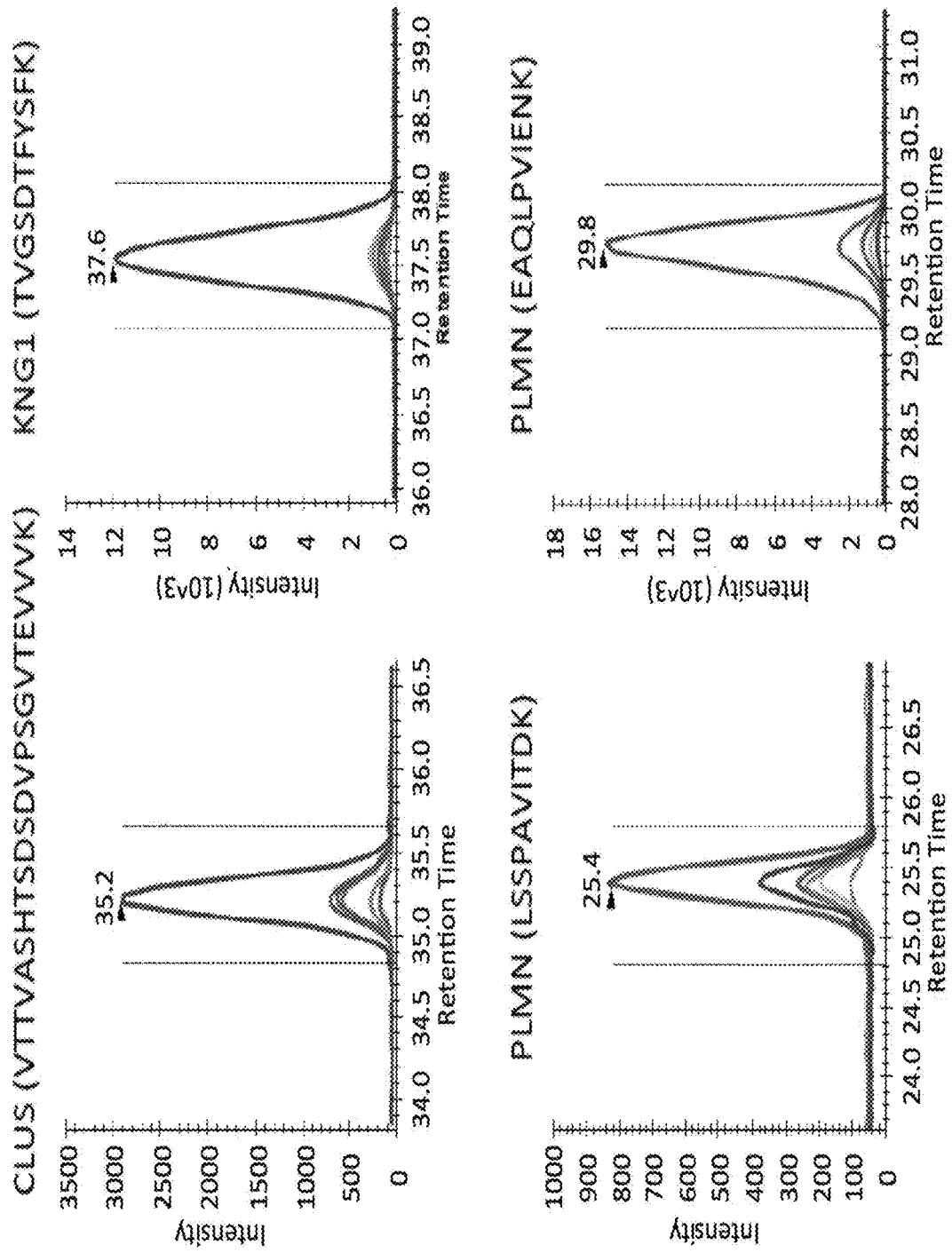
Figure 13F:
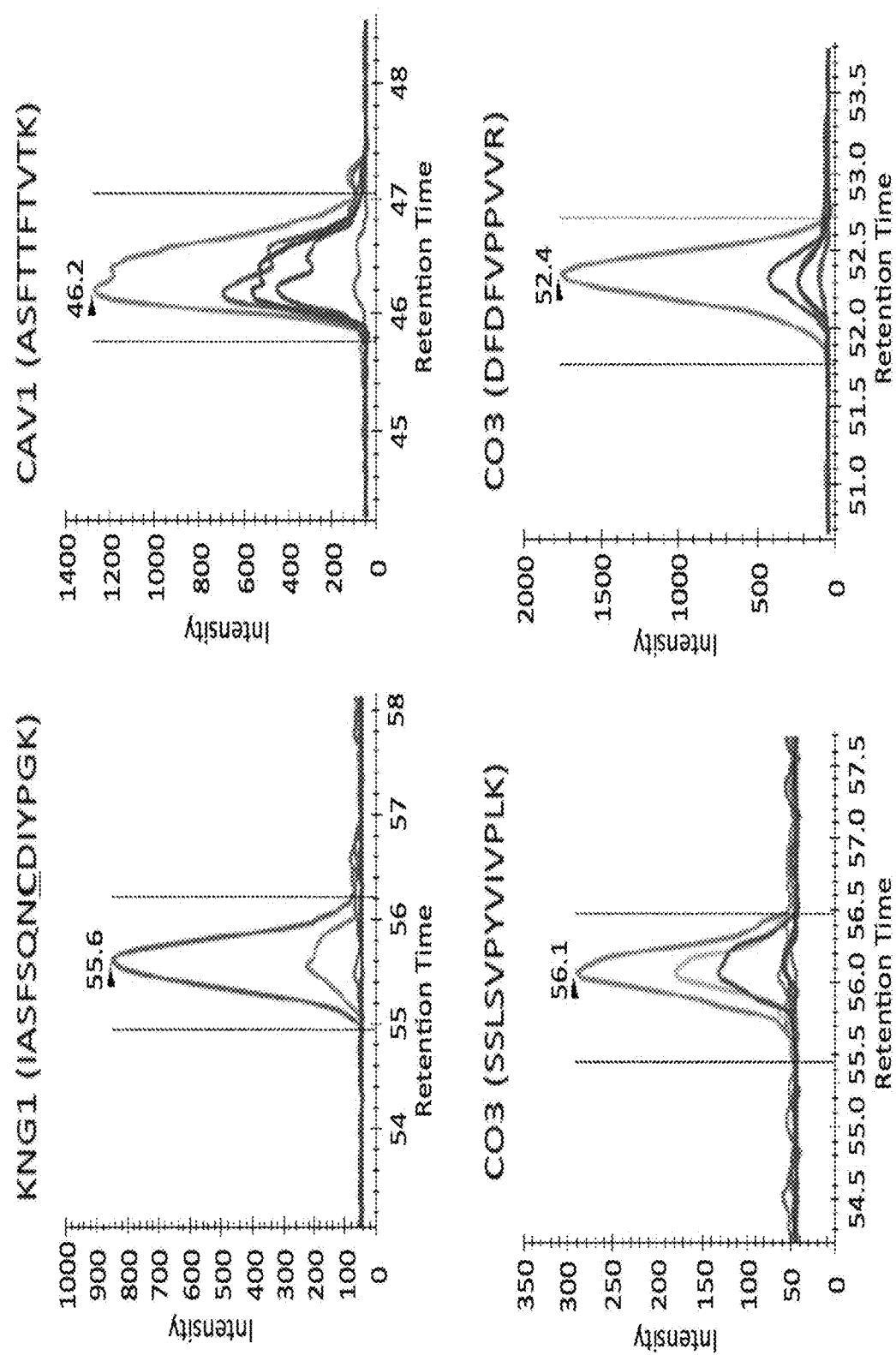
Figure 13G:
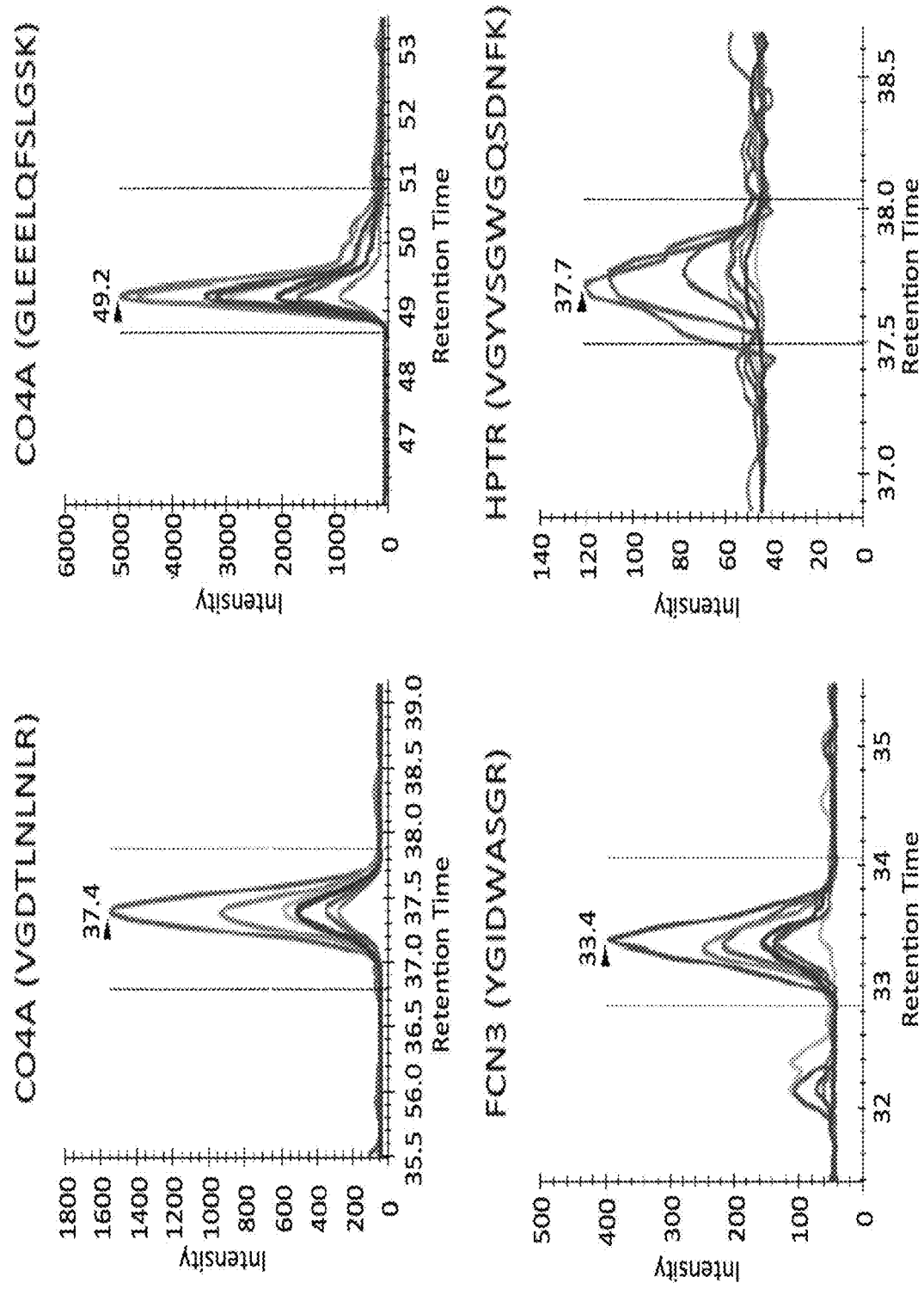
Figure 13H:
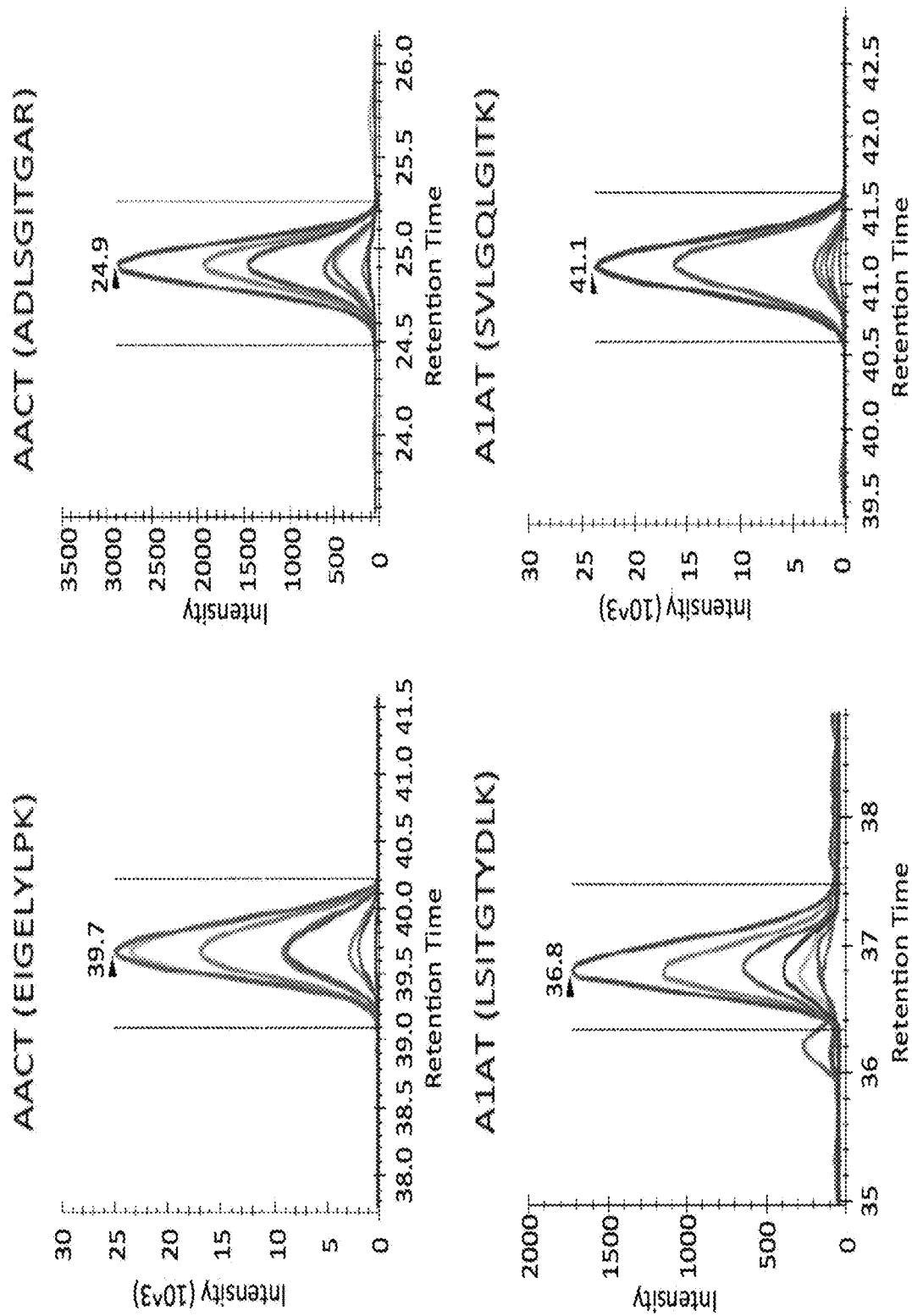
Figure 13I:
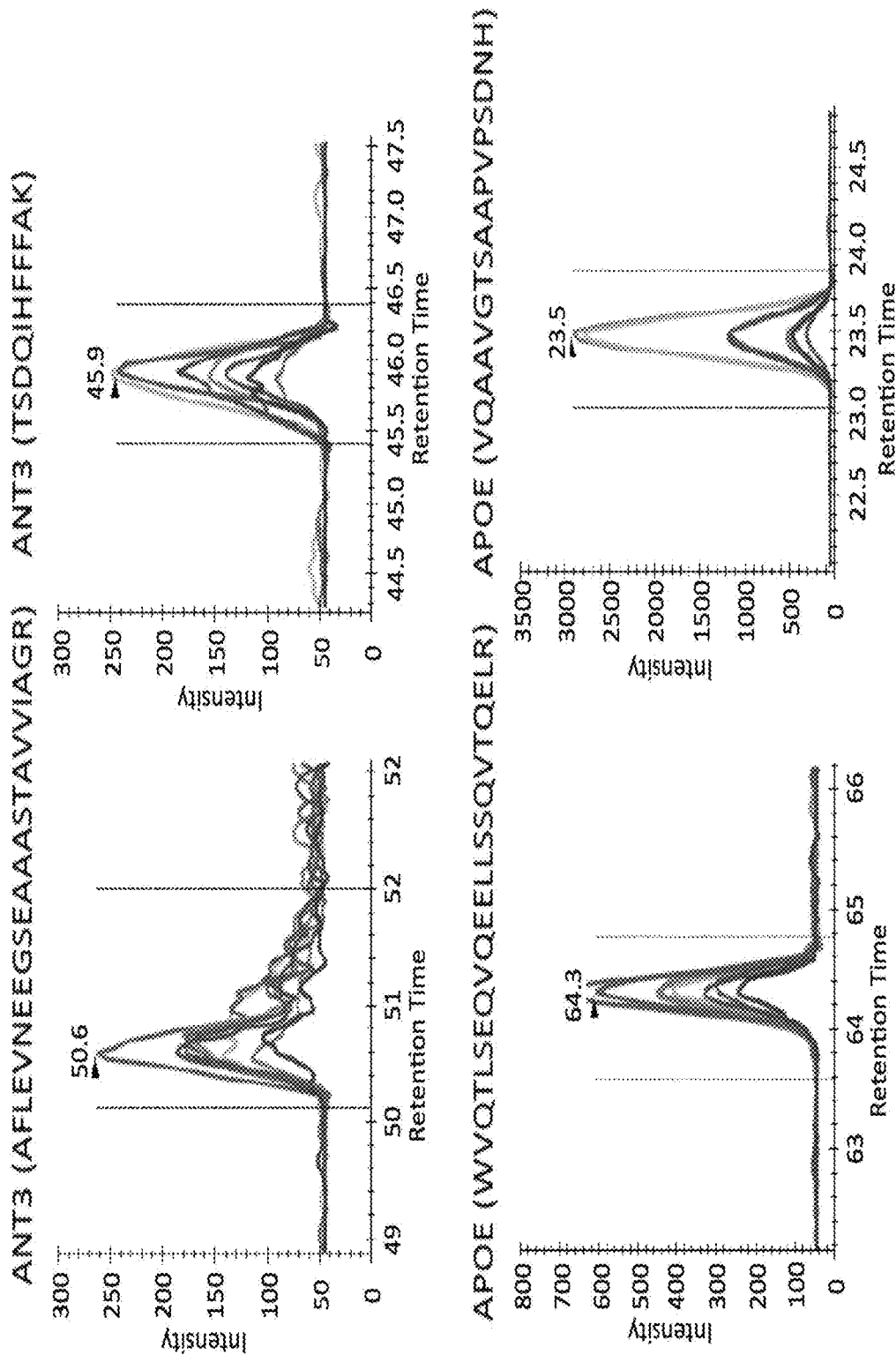
Figure 13J:
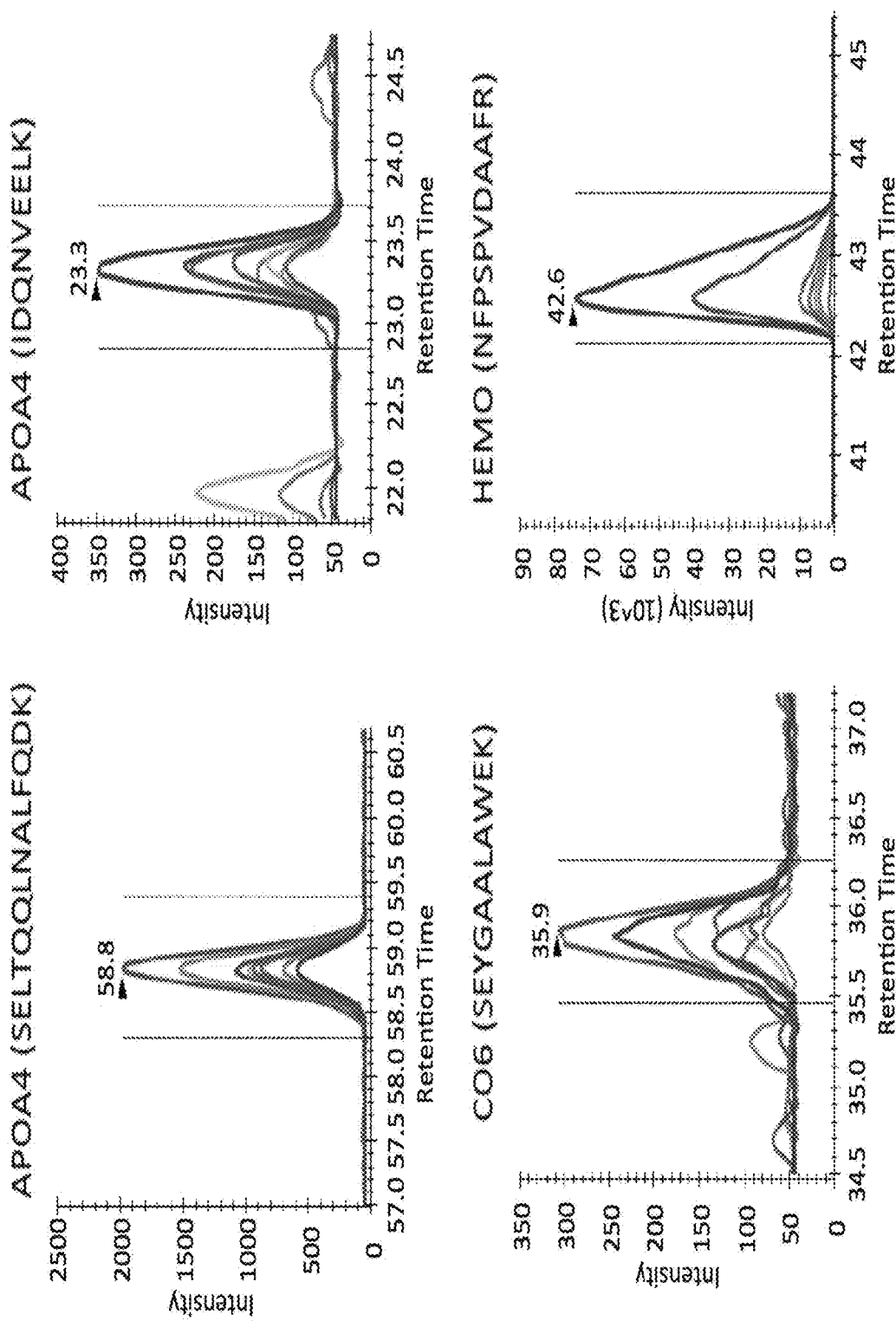
Figure 13K:
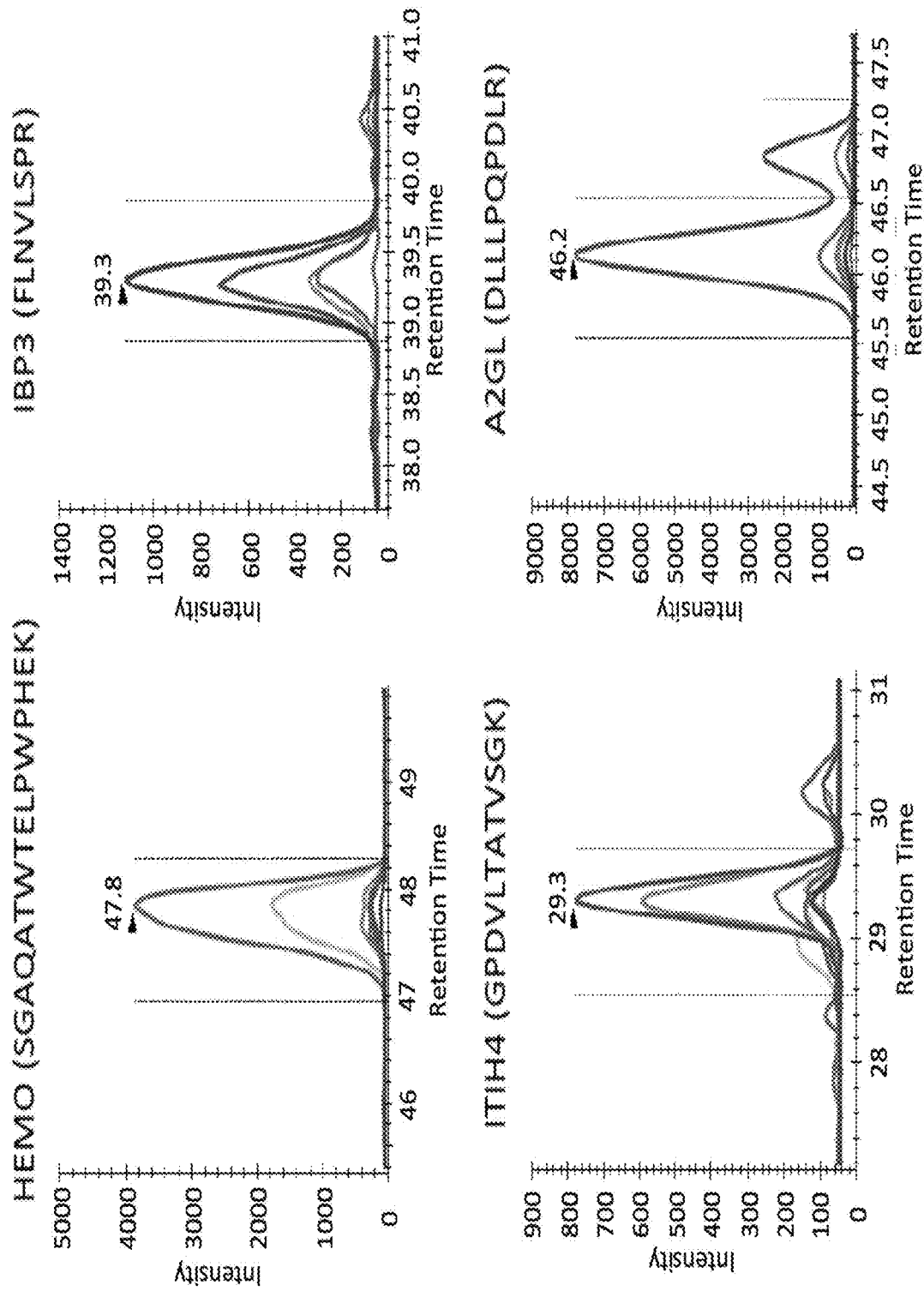
Figure 13L:
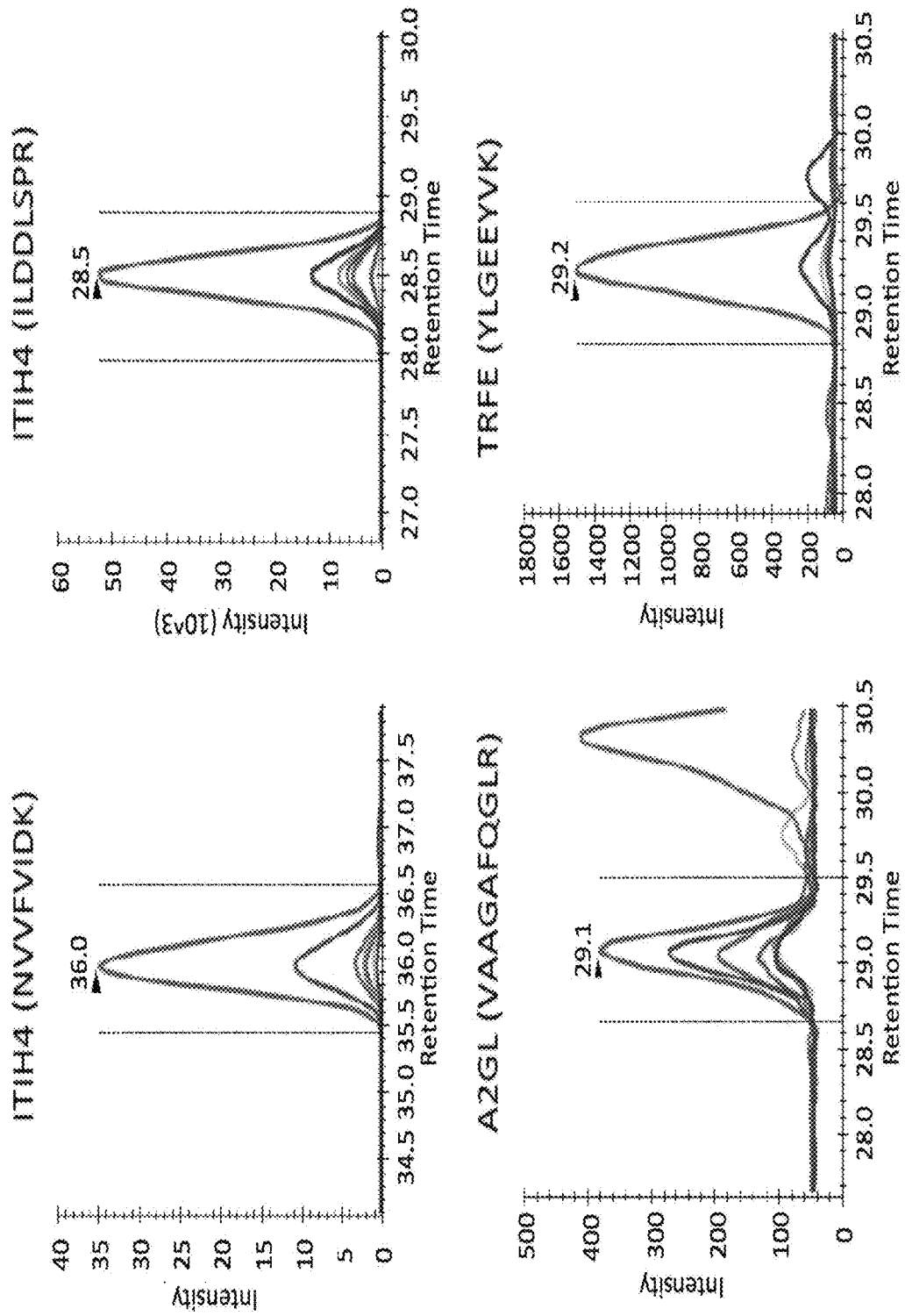
Figure 13M:
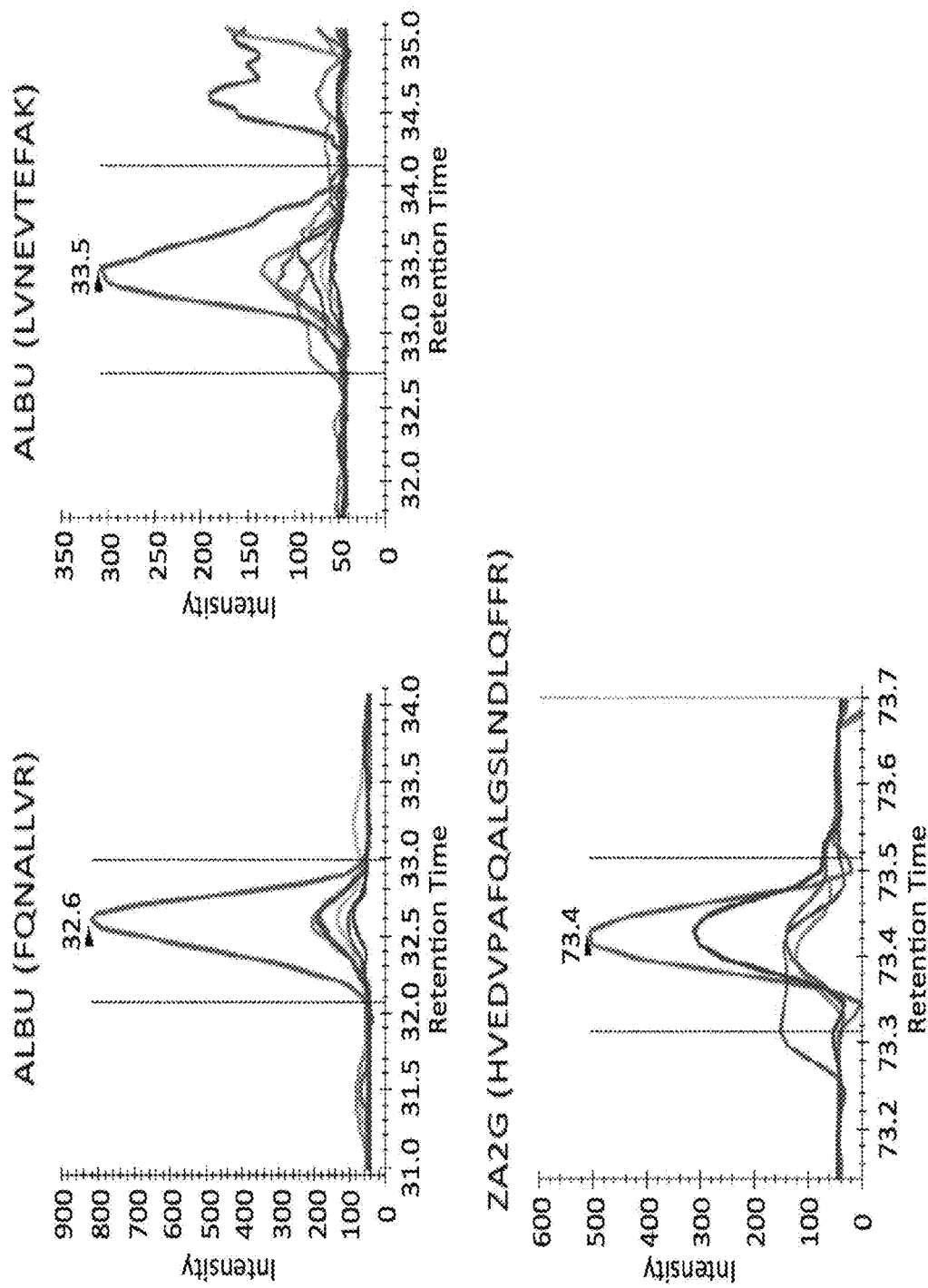
Figure 13N:
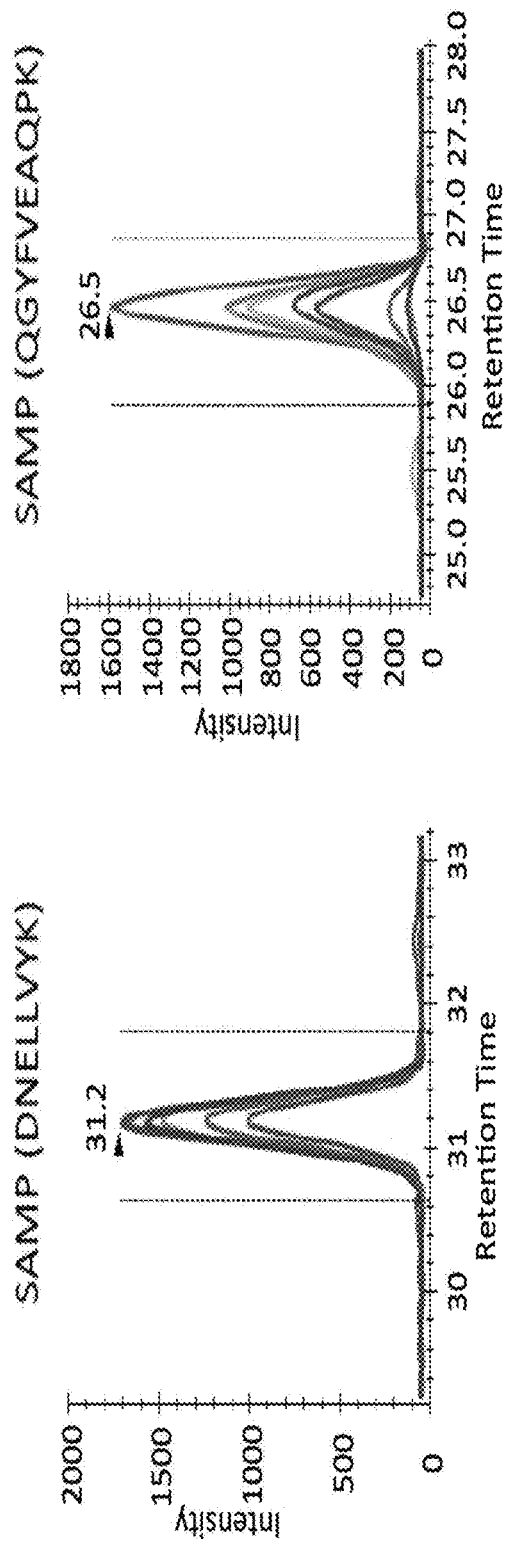

The MRM method was then reduced to up to 2 peptides per protein, three transitions per peptide and it was applied to 6 depleted and crude reference pool samples using scheduled MRM with 10 min RT window to assess the reproducibility. In the scheduled MRM run, TGF-β1 was not detected in both depleted and crude serum samples, therefore it was removed from the MRM method. The chromatogram results of the 53 peptides (from 32 proteins) measured in the scheduled MRM runs are shown in FIG. 13A-N.

Figure 7:
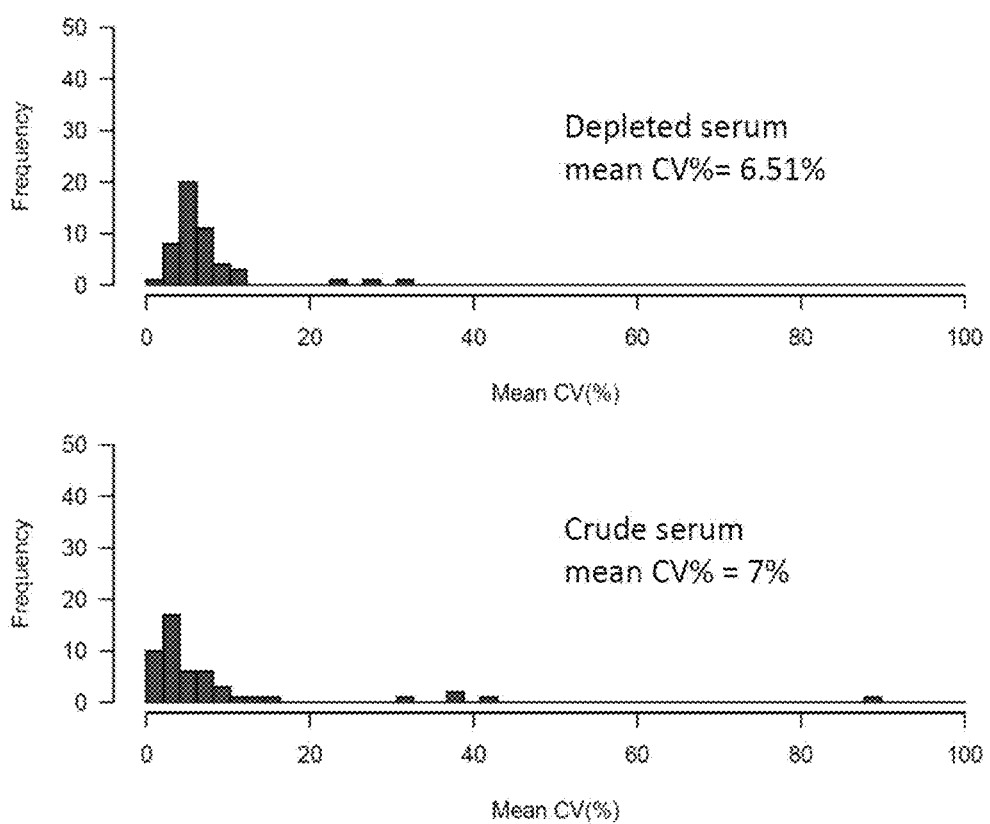
FIG. 7. Histogram of MRM transition CV % distributions calculated from the 6 scheduled MRM replicate runs of depleted (upper) and crude (down) serum samples.

CV % of each of the MRM transition from the depleted and crude replicate runs was calculated and CV % of the peptide was obtained by taking average across all the transitions for the given peptide. The MRM transitions and their CV % s are listed in Table 2. A histogram of the peptide CV % distribution is shown in FIG. 7. Although the CV % s of 6 peptides are over 30%, most of the peptides are below 10%. Among 6 peptides with high CV % s, 4 peptides have alternative low CV % peptides for the protein of interest. The mean CV % of the 6 replicate runs are 6.71% and 7% on the depleted and crude serum samples, respectively. These results indicated that the system is robust and sensitive enough to carry out MRM validation on crude serum samples.

TABLE 2

MRM transitions of 31 serum proteins and CV% of MRM assays in the depleted and crude serum samples

| Protein Names | Uniprot Accession No. | Peptide Sequence | Precursor Mz | Product Mz | Fragment Ion type | RT | Peak Rank | Depleted samples CV | Depleted samples mean CV(%) | Crude samples CV | Crude samples mean CV(%) |
|---|---|---|---|---|---|---|---|---|---|---|---|
| Protein AMBP | P02760 | ETLLQDFR | 511.2693 | 678.357 | Y5 | 41.48 | 2 | 1.86 | 2.78 | 3.11 | 3.19 |
| | | | 511.2693 | 565.2729 | y4 | 41.56 | 1 | 3.44 | | 2.98 | |
| | | | 511.2693 | 437.2143 | Y3 | 41.39 | 3 | 3.03 | | 3.48 | |
| Apolipoprotein A-I | P02647 | DYVSQFEGSALGK | 700.8383 | 1023.511 | y10 | 43.29 | 1 | 3.80 | 3.45 | 1.13 | 1.21 |
| | | | 700.8383 | 808.4199 | y8 | 43.26 | 2 | 3.45 | | 1.49 | |
| | | | 700.8383 | 204.1343 | y2 | 43.27 | 3 | 3.10 | | 1.01 | |
| | | LLDNWDSVTSTFSK | 806.8963 | 971.468 | Y9 | 52.27 | 1 | 3.04 | 3.61 | 1.80 | 1.80 |
| | | | 806.8963 | 856.4411 | y8 | 52.28 | 3 | 3.81 | | 1.77 | |
| | | | 806.8963 | 670.3406 | y6 | 52.28 | 2 | 4.00 | | 1.83 | |
| Apolipoprotein C-III | P02656 | DALSSVQESQVAQQAR | 858.9292 | 1144.571 | y10 | 29.73 | 2 | 5.00 | 6.66 | 6.19 | 3.09 |
| | | | 858.9292 | 887.4694 | y8 | 29.68 | 3 | 7.37 | | 1.74 | |
| | | | 858.9292 | 573.3103 | Y5 | 29.69 | 1 | 7.60 | | 1.33 | |
| | | GWVTDGFSSLK | 598.8009 | 953.4938 | Y9 | 46.52 | 2 | 4.17 | 4.59 | 2.55 | 2.37 |
| | | | 598.8009 | 854.4254 | y8 | 46.46 | 1 | 3.88 | | 2.08 | |
| | | | 598.8009 | 753.3777 | y7 | 46.55 | 3 | 5.72 | | 2.48 | |
| Pigment epithelium-derived factor | P36955 | TVQAVLTVPK | 528.3266 | 855.5298 | y8 | 33.87 | 1 | 5.88 | 5.44 | 8.21 | 9.11 |
| | | | 528.3266 | 727.4713 | y7 | 33.9 | 2 | 4.65 | | 10.96 | |
| | | | 528.3266 | 244.1656 | y2 | 33.9 | 3 | 5.80 | | 8.16 | |
| | | DTDTGALLFIGK | 625.835 | 1034.588 | y10 | 48.94 | 3 | 3.97 | 4.43 | 4.55 | 5.62 |
| | | | 625.835 | 818.5135 | y8 | 48.98 | 1 | 3.54 | | 4.84 | |
| | | | 625.835 | 204.1343 | y2 | 49.01 | 2 | 5.77 | | 7.47 | |
| Complement component C9 | P02748 | TEHYEEQIEAFK | 508.5719 | 607.345 | Y5 | 32.05 | 2 | 4.43 | 4.57 | 5.75 | 5.59 |
| | | | 508.5719 | 494.2609 | y4 | 32.1 | 1 | 7.31 | | 3.97 | |
| | | | 508.5719 | 147.1128 | y1 | 32.12 | 3 | 1.98 | | 7.06 | |
| | P02748 | LSPIYNLVPVK | 621.8765 | 1042.63 | y9 | 51.79 | 3 | 3.66 | 3.22 | 3.70 | 3.56 |
| | | | 621.8765 | 832.4927 | y7 | 51.79 | 1 | 2.48 | | 3.53 | |
| | | | 621.8765 | 343.234 | Y3 | 51.79 | 2 | 3.52 | | 3.46 | |
| Haptoglobin | P00738 | TEGDGVYTLNNEK | 720.3361 | 1209.575 | y11 | 24.46 | 2 | 10.09 | 10.95 | 32.02 | 32.33 |
| | | | 720.3361 | 881.4363 | y7 | 24.43 | 1 | 11.22 | | 31.94 | |
| | | | 720.3361 | 718.373 | y6 | 24.45 | 3 | 11.52 | | 33.03 | |
| | | VTSIQDWVQK | 602.322 | 1003.521 | y8 | 37.28 | 1 | 5.16 | 5.63 | 1.33 | 1.63 |
| | | | 602.322 | 803.4046 | y6 | 37.29 | 2 | 4.69 | | 1.51 | |
| | | | 602.322 | 675.3461 | Y5 | 37.25 | 3 | 7.03 | | 2.07 | |

TABLE 2-continued

MRM transitions of 31 serum proteins and CV% of
MRM assays in the depleted and crude serum samples

| Protein Names | Uniprot Accession No. | Peptide Sequence | Precursor Mz | Product Mz | Fragment Ion type | RT | Peak Rank | Depleted samples CV | Depleted samples mean CV(%) | Crude samples CV | Crude samples mean CV(%) |
|---|---|---|---|---|---|---|---|---|---|---|---|
| Vitronectin | P04004 | DVWGIEGP IDAAFTR | 823.9123 | 1076.537 | y10 | 62.48 | 2 | 7.60 | 7.02 | 3.07 | 3.39 |
| | | | 823.9123 | 947.4945 | Y9 | 62.46 | 1 | 6.77 | | 3.12 | |
| | | | 823.9123 | 890.473 | y8 | 62.48 | 3 | 6.70 | | 3.97 | |
| | | FEDGVLDP DYPR | 711.8304 | 875.4258 | y7 | 38.73 | 2 | 4.94 | 5.71 | 2.27 | 2.54 |
| | | | 711.8304 | 762.3417 | y6 | 38.68 | 3 | 4.83 | | 3.55 | |
| | | | 711.8304 | 647.3148 | Y5 | 38.67 | 1 | 7.34 | | 1.80 | |
| Alpha-2-macroglobulin | P01023 | NEDSLVFV QTDK | 697.8435 | 1151.594 | y10 | 36.15 | 2 | 11.91 | 8.17 | 2.33 | 2.05 |
| | | | 697.8435 | 737.3828 | y6 | 36.12 | 1 | 4.88 | | 2.27 | |
| | | | 697.8435 | 491.246 | y4 | 36.15 | 3 | 7.72 | | 1.55 | |
| Apolipoprotein A-II | P02652 | EPCVESLV SQYFQTVT DYGK | 1175.549 | 1436.669 | y12 | 74.05 | 1 | 8.94 | 10.23 | 6.63 | 6.73 |
| | | | 1175.549 | 583.2722 | Y5 | 74.01 | 2 | 10.55 | | 7.72 | |
| | | | 1175.549 | 204.1343 | y2 | 74.07 | 3 | 11.21 | | 5.85 | |
| Clusterin | P10909 | ELDESLQV AER | 644.8226 | 802.4417 | y7 | 29.77 | 1 | 4.79 | 4.37 | 1.90 | 2.03 |
| | | | 644.8226 | 602.3257 | Y5 | 29.75 | 3 | 3.15 | | 1.75 | |
| | | | 644.8226 | 375.1987 | Y3 | 29.79 | 2 | 5.18 | | 2.43 | |
| | | VTTVASHT SDSDVPSG VTEVVVK | 772.0639 | 1014.583 | y10 | 36.13 | 1 | 5.39 | 7.53 | 2.13 | 3.33 |
| | | | 772.0639 | 917.5302 | Y9 | 36.12 | 2 | 8.48 | | 4.00 | |
| | | | 772.0639 | 830.4982 | y8 | 36.14 | 3 | 8.72 | | 3.85 | |
| Kininogen-1 | P01042 | TVGSDTFY SFK | 626.2982 | 1051.473 | y9 | 38.42 | 1 | 5.62 | 7.29 | 1.79 | 4.42 |
| | | | 626.2982 | 994.4516 | y8 | 38.39 | 3 | 8.16 | | 5.20 | |
| | | | 626.2982 | 907.4196 | y7 | 38.38 | 2 | 8.08 | | 6.29 | |
| | | IASFSQNC DIYPGK | 800.3772 | 464.2504 | y4 | 56.56 | 2 | 1.77 | 27.56 | 9.31 | 37.98 |
| | | | 800.3772 | 301.187 | Y3 | 56.59 | 1 | 1.57 | | 6.42 | |
| | | | 800.3772 | 204.1343 | y2 | 56.65 | 3 | 79.33 | | 98.21 | |
| Plasminogen | P00747 | LSSPAVIT DK | 515.7926 | 917.4938 | y9 | 26.08 | 3 | 5.28 | 5.40 | 14.77 | 14.74 |
| | | | 515.7926 | 830.4618 | y8 | 26.01 | 1 | 5.41 | | 14.01 | |
| | | | 515.7926 | 743.4298 | y7 | 26.05 | 2 | 5.50 | | 15.45 | |
| | | EAQLPVIE NK | 570.8166 | 812.4876 | y7 | 30.56 | 2 | 5.65 | 4.13 | 3.01 | 2.51 |
| | | | 570.8166 | 699.4036 | y6 | 30.56 | 1 | 4.53 | | 2.66 | |
| | | | 570.8166 | 503.2824 | y4 | 30.62 | 3 | 2.21 | | 1.87 | |
| Complement C3 | P01024 | SSLSVPYV IVPLK | 701.4212 | 928.5866 | y8 | 57.47 | 1 | 2.72 | 5.31 | 3.67 | 3.68 |
| | | | 701.4212 | 456.318 | y4 | 57.42 | 3 | 8.32 | | 3.78 | |
| | | | 701.4212 | 357.2496 | Y3 | 57.41 | 2 | 4.88 | | 3.59 | |
| | | DFDFVPPV VR | 595.8139 | 813.4981 | y7 | 53.51 | 3 | 4.02 | 4.95 | 2.22 | 1.96 |
| | | | 595.8139 | 666.4297 | y6 | 53.5 | 2 | 5.76 | | 1.70 | |
| | | | 595.8139 | 567.3613 | Y5 | 53.5 | 1 | 5.08 | | 1.95 | |
| Complement C4-A | P0C0L4 | VGDTLNLN LR | 557.8144 | 742.457 | y6 | 38.44 | 2 | 4.65 | 3.66 | 12.75 | 12.53 |
| | | | 557.8144 | 629.3729 | Y5 | 38.35 | 1 | 4.09 | | 12.55 | |
| | | | 557.8144 | 402.2459 | Y3 | 38.44 | 3 | 2.25 | | 12.28 | |
| | | GLEEELQF SLGSK | 718.867 | 879.4934 | y8 | 50.34 | 3 | 4.74 | 5.60 | 7.39 | 6.61 |
| | | | 718.867 | 766.4094 | y7 | 50.33 | 2 | 6.24 | | 6.57 | |
| | | | 718.867 | 638.3508 | y6 | 50.27 | 1 | 5.81 | | 5.88 | |
| Alpha-1-antichymotrypsin | P01011 | EIGELYLP K | 531.2975 | 819.4611 | y7 | 40.64 | 1 | 5.45 | 5.25 | 2.63 | 2.69 |
| | | | 531.2975 | 633.397 | Y5 | 40.62 | 3 | 5.65 | | 2.73 | |
| | | | 531.2975 | 244.1656 | y2 | 40.64 | 2 | 4.66 | | 2.72 | |
| | | ADLSGITG AR | 480.7591 | 661.3628 | y7 | 25.38 | 1 | 10.67 | 10.50 | 37.17 | 37.16 |
| | | | 480.7591 | 574.3307 | y6 | 25.38 | 2 | 10.94 | | 37.21 | |
| | | | 480.7591 | 404.2252 | y4 | 25.38 | 3 | 9.90 | | 37.09 | |
| Ficolin-3 | O75636 | YGIDWASG R | 512.746 | 691.3158 | y6 | 34.46 | 1 | 4.26 | 5.94 | 5.98 | 6.69 |
| | | | 512.746 | 576.2889 | Y5 | 34.4 | 2 | 6.40 | | 6.39 | |
| | | | 512.746 | 390.2096 | y4 | 34.46 | 3 | 7.15 | | 7.69 | |
| Haptoglobin-related protein | P00739 | VGYVSGWG QSDNFK | 772.3624 | 1125.496 | y10 | 38.47 | 1 | 7.01 | 9.53 | 2.89 | 3.07 |
| | | | 772.3624 | 1038.464 | Y9 | 38.57 | 3 | 11.79 | | 3.69 | |
| | | | 772.3624 | 795.3632 | y7 | 38.63 | 2 | 9.80 | | 2.64 | |
| Alpha-1-antitrypsin | P01009 | LSITGTYD LK | 555.8057 | 910.488 | y8 | 37.85 | 2 | 5.39 | 4.15 | 7.25 | 7.06 |
| | | | 555.8057 | 797.404 | y7 | 37.81 | 1 | 3.22 | | 6.51 | |
| | | | 555.8057 | 696.3563 | y6 | 37.73 | 3 | 3.85 | | 7.42 | |
| | | SVLGQLGI TK | 508.3109 | 829.5142 | y8 | 42.11 | 1 | 1.70 | 2.13 | 10.88 | 10.74 |
| | | | 508.3109 | 716.4301 | y7 | 42.06 | 2 | 1.92 | | 10.57 | |
| | | | 508.3109 | 418.266 | y4 | 42.12 | 3 | 2.76 | | 10.77 | |

TABLE 2-continued

MRM transitions of 31 serum proteins and CV% of
MRM assays in the depleted and crude serum samples

| Protein Names | Uniprot Accession No. | Peptide Sequence | Precursor Mz | Product Mz | Fragment Ion type | RT | Peak Rank | Depleted samples CV | Depleted samples mean CV(%) | Crude samples CV | Crude samples mean CV(%) |
|---|---|---|---|---|---|---|---|---|---|---|---|
| Anti-thrombin-III | P01008 | TSDQIHFFFAK | 447.5593 | 796.4141 | y6 | 47.01 | 1 | 4.54 | 4.08 | 6.48 | 6.92 |
| | | | 447.5593 | 659.3552 | Y5 | 47.02 | 3 | 3.80 | | 7.72 | |
| | | | 447.5593 | 147.1128 | y1 | 47.05 | 2 | 3.91 | | 6.57 | |
| Apolipo-protein A-IV | P06727 | SELTQQLNALFQDK | 817.9229 | 948.5149 | y8 | 59.81 | 3 | 2.01 | 1.71 | 6.45 | 5.95 |
| | | | 817.9229 | 835.4308 | y7 | 59.84 | 2 | 1.24 | | 5.86 | |
| | | | 817.9229 | 537.2667 | y4 | 59.81 | 1 | 1.87 | | 5.53 | |
| | | IDQNVEELK | 544.2851 | 974.4789 | y8 | 23.8 | 1 | 24.25 | 23.65 | 89.75 | 89.78[a] |
| | | | 544.2851 | 859.452 | y7 | 23.79 | 2 | 24.25 | | 90.04 | |
| | | | 544.2851 | 731.3934 | y6 | 23.79 | 3 | 22.47 | | 89.56 | |
| Apolipo-protein E | P02649 | WVQTLSEQVQEELLSSQVTQELR | 910.803 | 1047.543 | y9 | 65.53 | 1 | 9.77 | 9.06 | 8.81 | 8.59 |
| | | | 910.803 | 745.4203 | y6 | 65.53 | 3 | 10.03 | | 8.02 | |
| | | | 910.803 | 646.3519 | Y5 | 65.5 | 2 | 7.37 | | 8.95 | |
| | | VQAAVGTSAAPVPSDNH | 810.9025 | 836.3897 | y8 | 23.98 | 3 | 8.34 | 7.42 | 2.72 | 3.19 |
| | | | 810.9025 | 765.3526 | y7 | 24.01 | 2 | 6.46 | | 3.61 | |
| | | | 810.9025 | 569.2314 | Y5 | 23.98 | 1 | 7.45 | | 3.23 | |
| Caveolin-1 | Q03135 | ASFTTFTVTK | 551.7926 | 944.5088 | y8 | 47.5 | 1 | 7.22 | 8.55 | 70.85 | 54.18 |
| | | | 551.7926 | 797.4403 | y7 | 47.46 | 3 | 9.91 | | 71.42 | |
| | | | 551.7926 | 595.345 | Y5 | 47.4 | 2 | 8.53 | | 20.28 | |
| Complement component C6 | P13671 | SEYGAALAWEK | 612.7984 | 1008.515 | y9 | 36.91 | 1 | 5.76 | 7.35 | 3.04 | 4.54 |
| | | | 612.7984 | 845.4516 | y8 | 36.9 | 2 | 7.56 | | 3.99 | |
| | | | 612.7984 | 717.393 | y6 | 36.92 | 3 | 8.72 | | 6.59 | |
| Hemopexin | P02790 | NFPSPVDAAFR | 610.8066 | 959.4945 | y9 | 43.76 | 1 | 4.97 | 5.00 | 0.53 | 0.68 |
| | | | 610.8066 | 862.4417 | y8 | 43.78 | 3 | 4.87 | | 0.71 | |
| | | | 610.8066 | 775.4097 | y7 | 43.75 | 2 | 5.16 | | 0.78 | |
| | | SGAQATWTELPWPHEK | 613.3004 | 906.4832 | y7 | 48.79 | 3 | 7.40 | 7.58 | 1.99 | 1.43 |
| | | | 613.3004 | 793.3991 | y6 | 48.81 | 1 | 7.83 | | 1.08 | |
| | | | 613.3004 | 510.2671 | y4 | 48.76 | 2 | 7.49 | | 1.23 | |
| Insulin-like growth factor-binding protein 3 | P17936 | FLNVLSPR | 473.2795 | 685.3991 | y6 | 40.48 | 1 | 6.39 | 8.86 | 8.40 | 8.40 |
| | | | 473.2795 | 472.2878 | y4 | 40.53 | 2 | 8.21 | | 7.61 | |
| | | | 473.2795 | 359.2037 | Y3 | 40.45 | 3 | 11.98 | | 9.18 | |
| Inter-alpha-trypsin inhibitor heavy chain H4 | Q14624 | NVVFVIDK | 467.2738 | 720.4291 | y6 | 37.16 | 1 | 4.38 | 4.51 | 4.35 | 3.61 |
| | | | 467.2738 | 621.3606 | Y5 | 37.17 | 2 | 5.22 | | 3.20 | |
| | | | 467.2738 | 375.2238 | Y3 | 37.12 | 3 | 3.94 | | 3.28 | |
| | | ILDDLSPR | 464.7585 | 815.4258 | y7 | 29.27 | 2 | 3.48 | 3.84 | 2.01 | 1.74 |
| | | | 464.7585 | 702.3417 | y6 | 29.27 | 1 | 4.51 | | 1.09 | |
| | | | 464.7585 | 472.2878 | y4 | 29.23 | 3 | 3.53 | | 2.13 | |
| Leucine-rich alpha-2-glycoprotein | P02750 | DLLLPQPDLR | 590.3402 | 838.4781 | y7 | 47.38 | 2 | 5.32 | 6.01 | 10.85 | 8.02 |
| | | | 590.3402 | 725.3941 | y6 | 47.36 | 1 | 4.91 | | 6.22 | |
| | | | 590.3402 | 288.203 | y2 | 47.38 | 3 | 7.80 | | 6.98 | |
| | P02750 | VAAGAFQGLR | 495.28 | 819.4472 | y8 | 29.94 | 1 | 8.30 | 6.28 | 3.16 | 3.55 |
| | | | 495.28 | 748.41 | y7 | 29.79 | 2 | 2.87 | | 3.50 | |
| | | | 495.28 | 620.3515 | Y5 | 29.89 | 3 | 7.67 | | 4.00 | |
| Vitamin D-binding protein | P02774 | SCESNSPFPVHPGTAECCTK | 755.6505 | 1023.423 | Y9 | 25.58 | 2 | 54.83 | 31.16 | 81.37 | 42.46 |
| | | | 755.6505 | 248.1605 | y2 | 25.52 | 1 | 7.50 | | 3.56 | |
| Serotransferrin | P02787 | YLGEEYVK | 500.7529 | 837.4353 | y7 | 30 | 2 | 8.05 | 7.07 | 1.72 | 1.38 |
| | | | 500.7529 | 724.3512 | y6 | 29.96 | 1 | 6.69 | | 1.62 | |
| | | | 500.7529 | 147.1128 | y1 | 29.97 | 3 | 6.47 | | 0.79 | |
| Serum albumin | P02768 | LVNEVTEFAK | 575.3111 | 937.4625 | y8 | 34.58 | 1 | 3.73 | 5.08 | 1.89 | 2.08 |
| | | | 575.3111 | 823.4196 | y7 | 34.56 | 3 | 3.95 | | 2.13 | |
| | | | 575.3111 | 694.377 | y6 | 34.54 | 2 | 7.56 | | 2.22 | |
| | | FQNALLVR | 480.7849 | 685.4355 | y6 | 33.84 | 1 | 4.74 | 6.82 | 1.44 | 1.55 |
| | | | 480.7849 | 571.3926 | Y5 | 33.85 | 2 | 5.55 | | 1.53 | |
| | | | 480.7849 | 500.3555 | y4 | 33.73 | 3 | 10.18 | | 1.69 | |

TABLE 2-continued

MRM transitions of 31 serum proteins and CV% of
MRM assays in the depleted and crude serum samples

| Protein Names | Uniprot Accession No. | Peptide Sequence | Precursor Mz | Product Mz | Fragment Ion type | RT | Peak Rank | Depleted samples CV | Depleted samples mean CV(%) | Crude samples CV | Crude samples mean CV(%) |
|---|---|---|---|---|---|---|---|---|---|---|---|
| Serum amyloid P-component | P02743 | DNELLVYK | 497.2662 | 764.4553 | y6 | 32.18 | 2 | 5.22 | 4.55 | 4.51 | 3.84 |
| | | | 497.2662 | 522.3286 | y4 | 32.2 | 1 | 4.17 | | 5.03 | |
| | | | 497.2662 | 310.1761 | y2 | 32.2 | 3 | 4.26 | | 1.98 | |
| | | QGYFVEAQPK | 583.7957 | 671.3723 | y6 | 26.96 | 2 | 6.71 | 6.27 | 5.22 | 5.61 |
| | | | 583.7957 | 572.3039 | Y5 | 26.93 | 1 | 7.01 | | 7.76 | |
| | | | 583.7957 | 244.1656 | y2 | 26.94 | 3 | 5.09 | | 3.85 | |
| Zinc alpha-2-glycoprotein | P25311 | HVEDVPAFQALGSLNDLQFFR | 801.7412 | 1196.606 | y10 | 73.43 | 1 | Not detected | | 8.06 | 8.63 |
| | | | 801.7412 | 939.4683 | y7 | 73.41 | 3 | | | 7.67 | |
| | | | 801.7412 | 175.119 | y1 | 73.43 | 2 | | | 10.16 | |

Figure 8A:
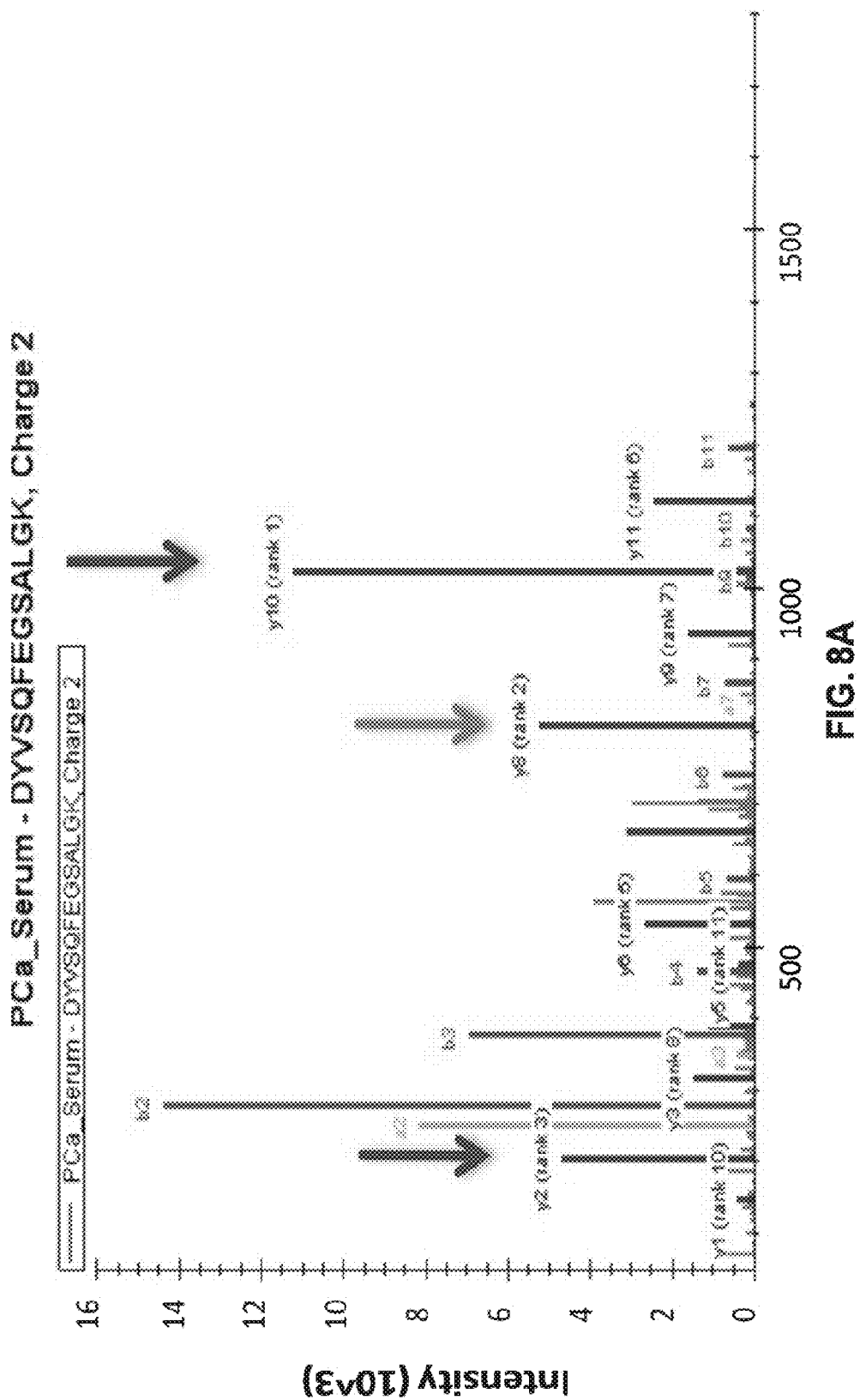
FIG. 8. An example demonstrating the reproducibility of the short gradient MRM runs on 63 serum samples. (a) MS/MS spectral for peptide DYVSQFEGSALGK, (b) Chromatogram result of the selected transitions of the peptide in the 38 mins gradient MRM run, (c) Transition Peak comparison between BH31 and 10 replicates, (d) Histogram of CV % of all the transitions in the 10 replicate runs.
Figure 8D:
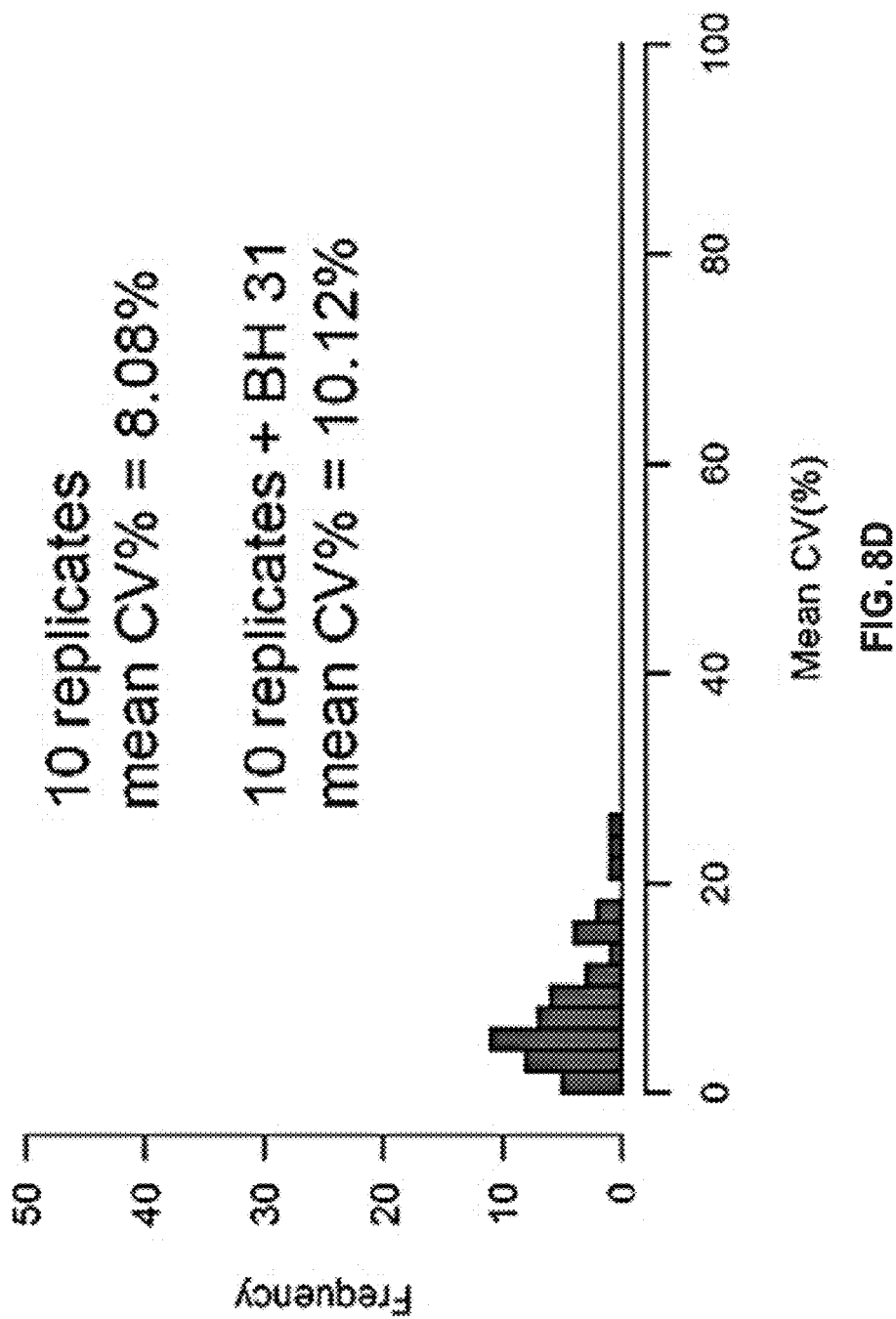
Figure 9A:
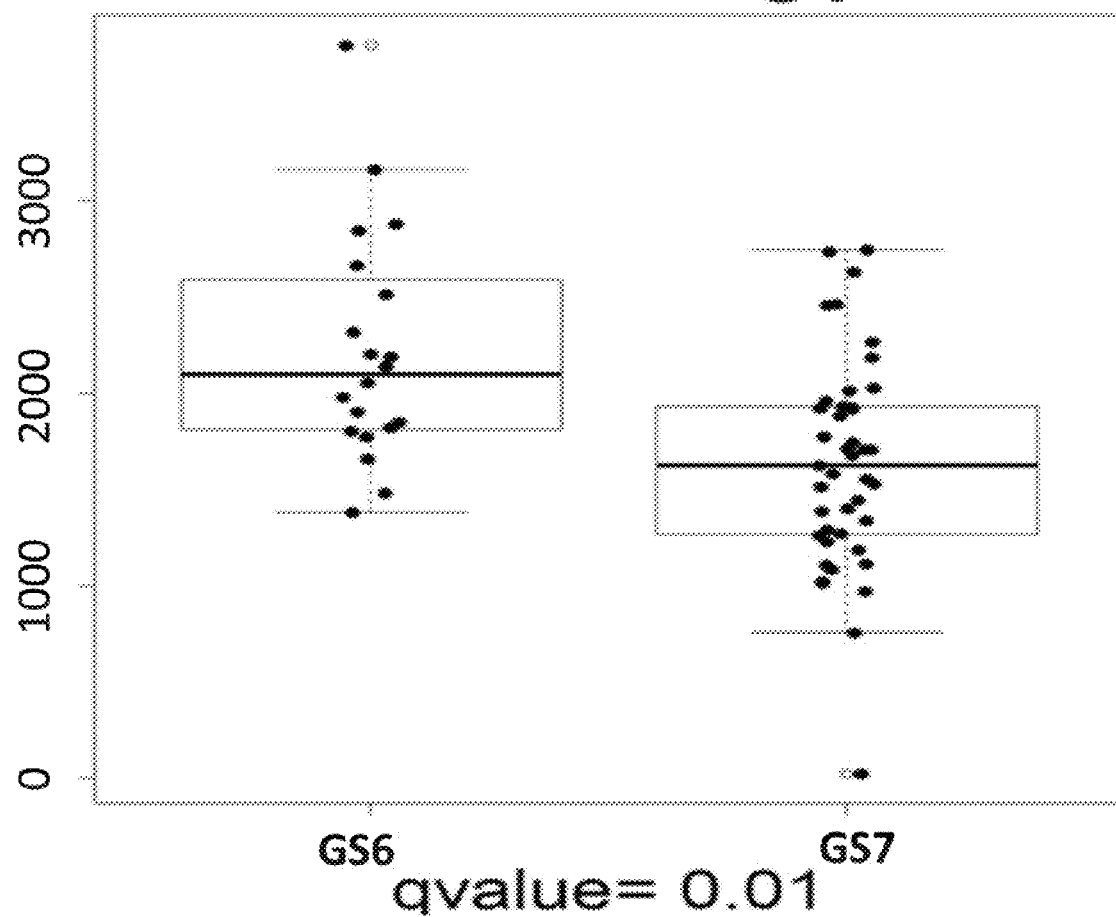
FIG. 9A-D. Two examples of peptides that were found to be differentially expressed in MRM results. A & B: box plot of the top one transition for peptide SCESNSPFPVHPG-TAECCTK from Vitamin D-binding protein (A) and peptide HVEDVPAFQALGSLNDLQFFR from zinc alpha 2-glycoprotein (B); C & D: area under the peak of all the transitions in each serum sample for peptide SCESNSPFPVHPG-TAECCTK from Vitamin D-binding protein (C) and peptide HVEDVPAFQALGSLNDLQFFR from zinc alpha 2-glycoprotein (D).
Figure 9B:
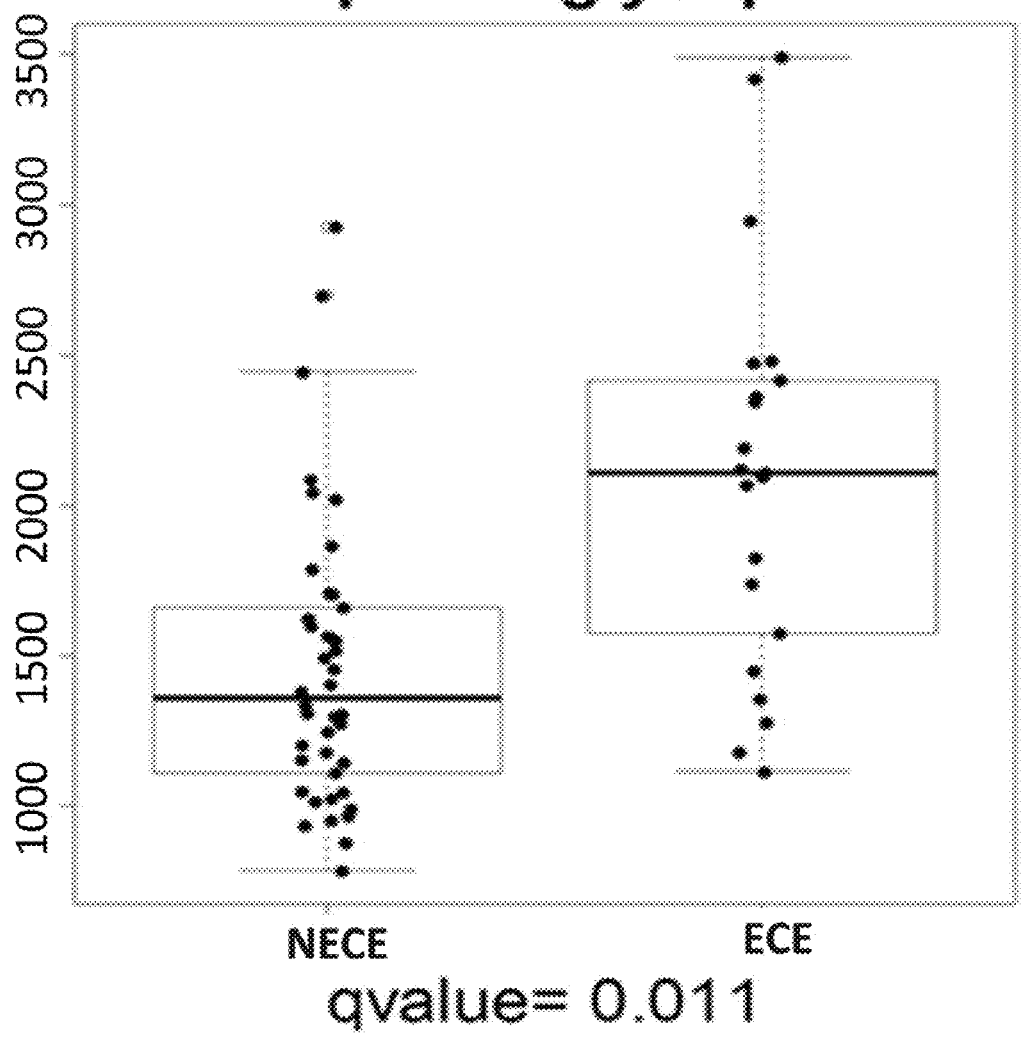
Figure 9C:
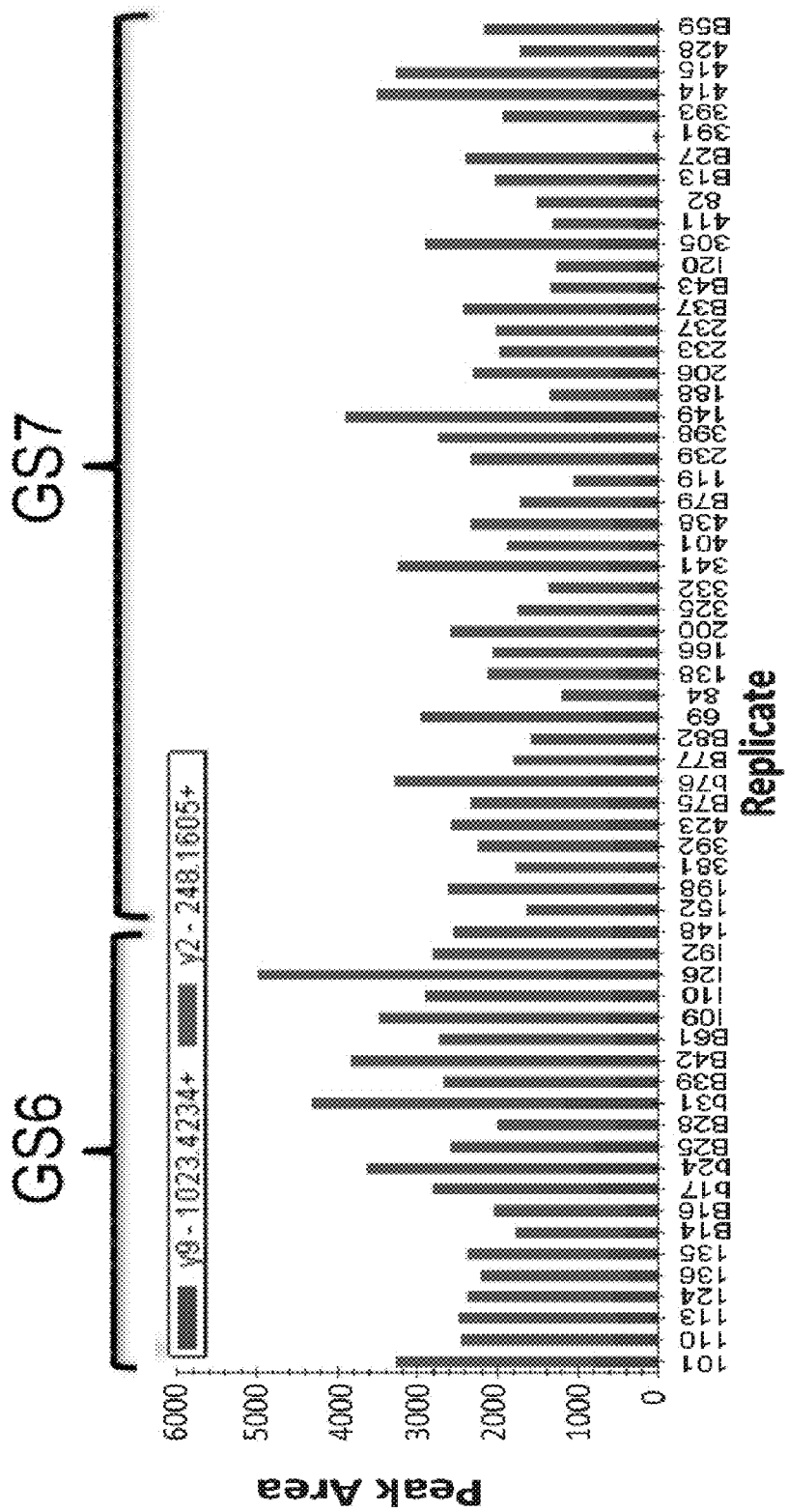
Figure 9D:
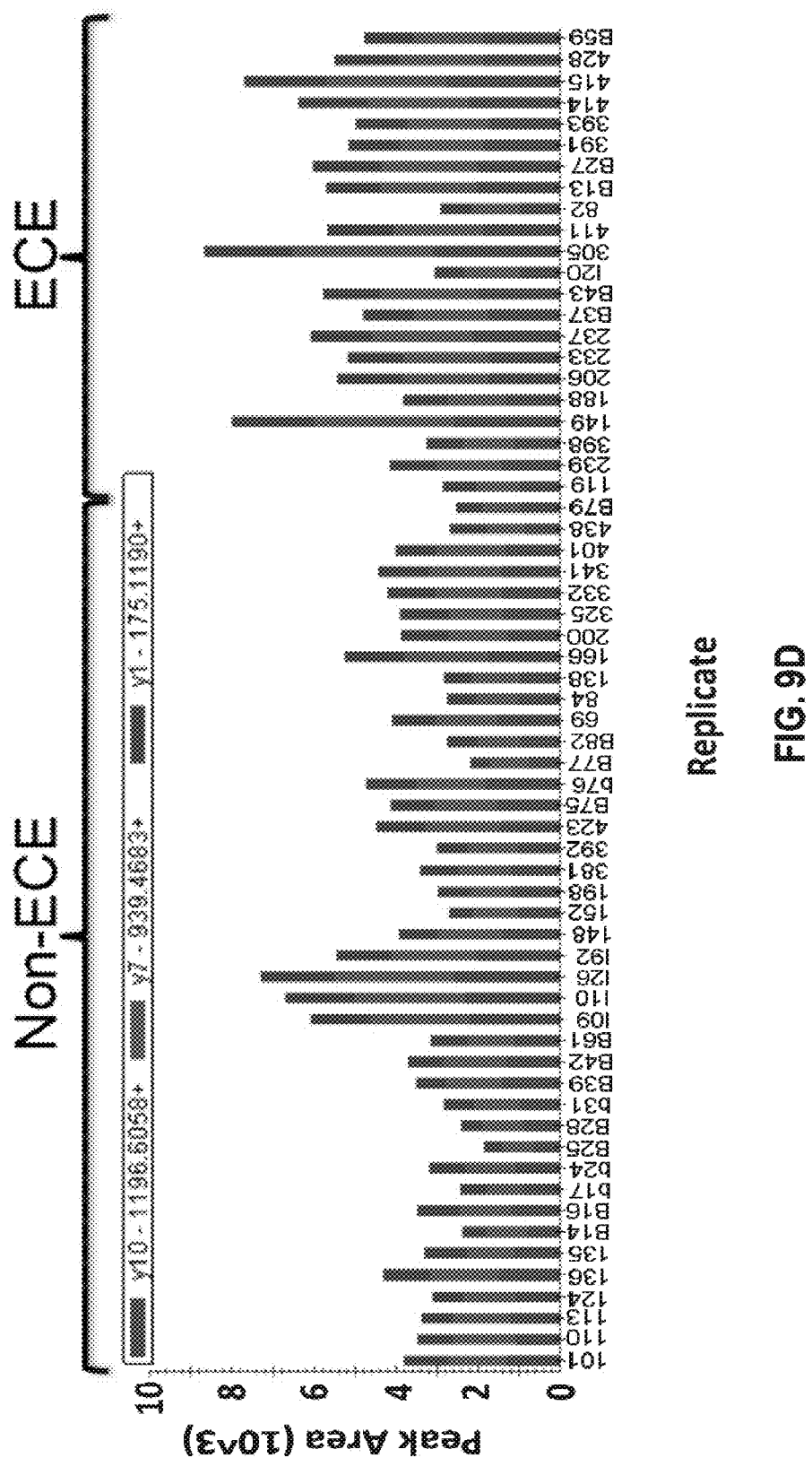

An independent cohort of serum samples (n=63) from PCa patients were selected for validation using the established MRM method. In order to increase the throughput of the MRM runs, the elution gradient was reduced from 118 min to 38 min. The shorter elution gradient was tested on both depleted and crude serum samples and the results are comparable with the long gradient (data not shown). The 63 serum samples were run using the MRM method with shorter elution gradient and blanks were run in-between each sample. 10 replicates of serum sample BH31 that was run at the beginning of the experiment were test after all the sample runs to assess the experimental reproducibility. The MRM data was analyzed in Skyline. All the peptides in each sample were manually inspected to ensure correct peaks were selected. An example of the MRM data is shown in FIG. 8. Three y ions with the highest intensities were selected as transitions for the peptide DYVSQFEGSALGK (+2) from Apolipoprotein A-I protein (FIG. 8 (a)). The chromatogram results of these 3 transitions in 38 min gradient can be seen in FIG. 8 (b). The area under the transition peak was quantified in sample BH31 and the 10 replicate samples, which were plotted as a stack column plot (FIG. 8 (c)). The area under the 3 transition peaks is very consistent from the beginning to the end of the experiment and no significant drop of sensitivity was observed for all the transitions. The CV % of each peptide was calculated and a histogram of the CV % distribution is shown in FIG. 8 (d). The mean CV % for all the peptides MRM results in the 10 replicates is 8.07%, which is similar to the previous runs. After including the BH31 sample, the mean CV % increase slightly to 10.12%.

The differentially expressed peptides in the MRM data were identified using Student's t-test. P-value and fold change was calculated for each peptide. Peptides with p-value less than 0.05 are listed in Table 3 and 4. Q-value was also provided as an indication of FDR. Two examples are shown in FIG. 9. Peptide SCESNSPFPVHPGTAECCTK from Vitamin D-binding protein (VTDB) were found to be significantly down-regulated in Gleason score 7 samples than Gleason score 6 (q-value=0.01). Lower level of Vitamin D and VTDB protein has been associated with higher risk of PCa (29, 30). The measured level of peptide HVEDVPAFQALGSLNDLQFFR from ZAG was significantly higher in the serum sample from patients with ECE in comparison to non-ECE patient. We have previously shown that ZAG is up-regulated in both the serum and tissue of patients with higher Gleason score (31). Similarly, PEDF was found in our previous study to be down regulated in Gleason score 7 patients comparing with Gleason score 5. Lower expression of the peptide TVQAVLTVPK from PEDF was more associated with ECE patient serum.

Figure 10:
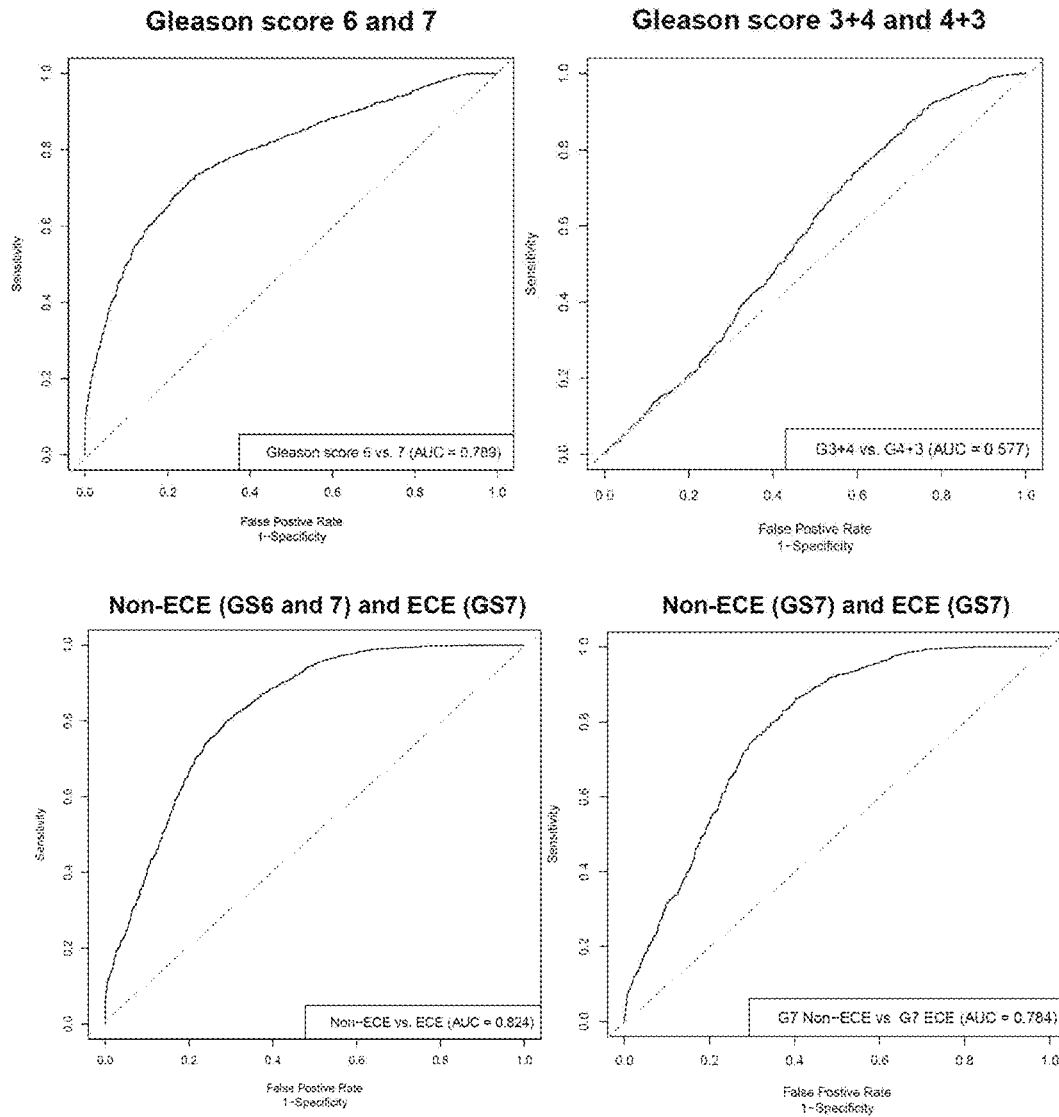
FIG. 10. ROC curves of prediction of Gleason score and organ confined status of the disease using PLS-DA with 200 times bootstrapping FIG. 11. ROC curve of 4 peptides panel in differentiating between non-ECE and ECE serum samples FIG. 12. 1D SDS PAGE gel showing the serum proteins after depletion. Protein loadings were adjusted according to the staining intensity of each lane FIG. 13A-N. Chromatogram results of the 53 peptides from 32 proteins measured in scheduled MRM runs. The chromatogram results are based on the initial unscheduled MRM runs with 8 transitions per peptides. Parts A-N correspond to the following peptides: A: SEQ ID NOs. 43, 9, 15 and 41; B: SEQ ID NOs. 10, 14, 42 and 26; C: SEQ ID NOs. 27, 29, 51 and 7; D: SEQ ID NOs. 30, 50, 11 and 19; E: SEQ ID NOs. 20, 37, 1 and 2; F: SEQ ID NOs. 38, 18, 21 and 22; G: SEQ ID NOs. 23, 24, 28 and 31; H: SEQ ID NOs. 5, 6, 3 and 4; I: SEQ ID NOs. 105, 8, 16 and 17; J: SEQ ID NOs. 12, 13, 25 and 32; K: SEQ ID NOs. 33, 34, 106 and 39; L: SEQ ID NOs. 35, 36, 40 and 44 (as shown in parts A-L in the order top left, top right, bottom left, bottom right with the Figure label orientated at the bottom of the page); M: SEQ ID NOs. 46, 45 and 52 (as shown in the order top left, top right, bottom left with the Figure label orientated at the bottom of the page); N: SEQ ID NOs. 47 and 48 (as shown in the order left then right with the Figure label orientated at the bottom of the page).

The relative abundance of the top one transition from all 50 peptides in the 63 clinical samples were fitted into a PLS-DA model and the predict performance was assessed through 200 times bootstrapping. The predictions in the out-of-bag samples were compared with the true group information and ROC curves were generated (FIG. 10). In the classification between Gleason score 6 and 7, the AUC value from the ROC curve is 0.789 (FIG. 10 (a)). However, the MRM data does not give sufficient prediction accuracy in classifying Gleason score 3+4 and 4+3 (AUC=0.577) (FIG. 10 (b)). The AUC value for differentiating between non-ECE and ECE is 0.824 (FIG. 10 (c)), which is highly favorable in providing more accurate staging information for treatment. If we focus only on Gleason score 7 patients, the differentiation between Gleason score 7 patients without ECE and Gleason score 7 patients with ECE gives a slightly lower AUC value of 0.784 (FIG. 10 (d)). The drop of accuracy may be explained by the smaller biological differences are expected within Gleason score 7 patents comparing to patients with different stages and Gleason score.

Figure 11:
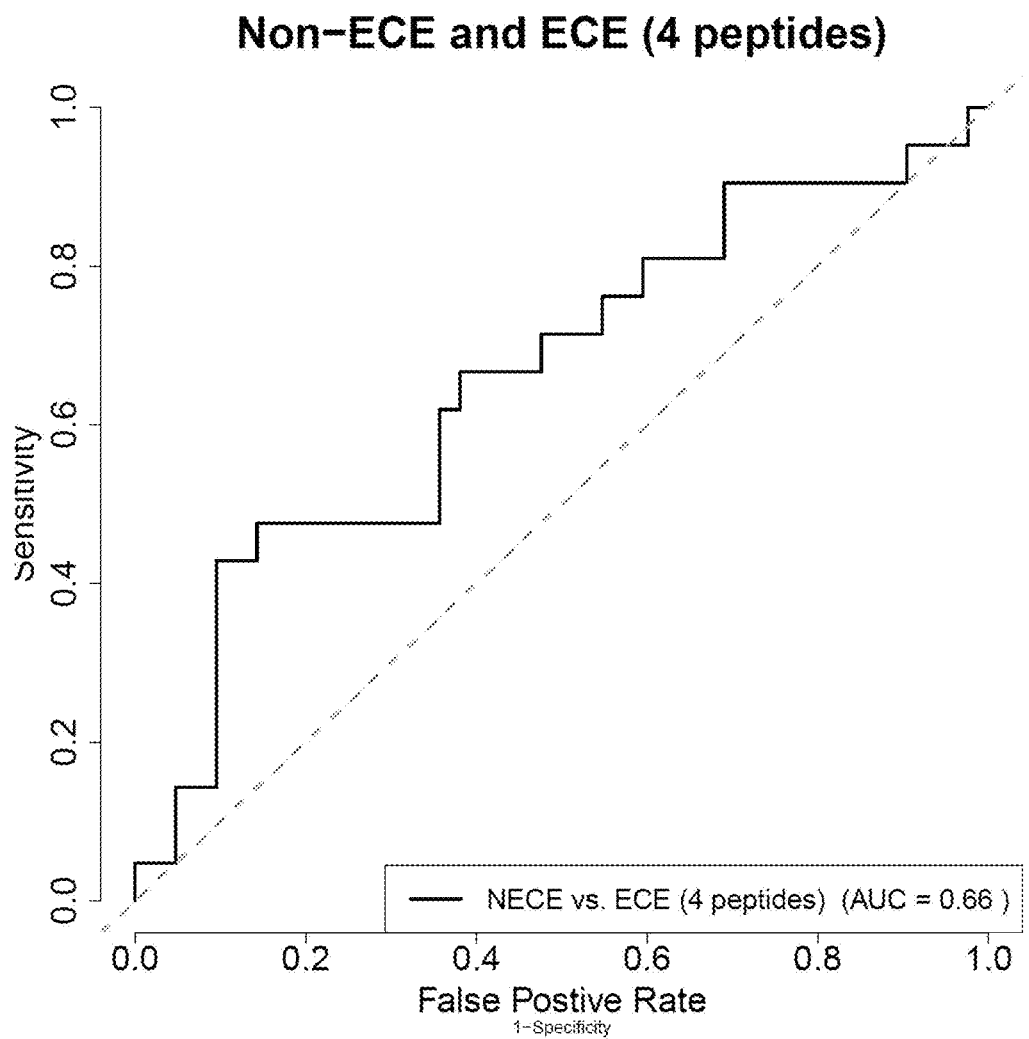

The serum biomarker panel for organ confined versus non-organ confined identified in the previously published 2D-DIGE study is comprised of 4 proteins: Protein AMBP, Haptoglobin, PEDF and Kininogen-1. MRM has been developed for peptides from these 4 proteins and they have been measured in the 63 clinical samples. In fact, the MRM data may not necessarily reflect the expression level changes at the protein level. But it is interesting to know if the prediction performance still holds when peptide level expression profile is used. Therefore the prediction performance of the peptides from the 4 proteins was evaluated using Random Forests method with 10 fold cross validation as adopted in the 2D-DIGE study. 3000 trees were grown and 8 features were randomly selected at each node. The ROC curve of the 4 peptide panel can be found in FIG. 11 and the AUC value calculated is 0.66. That indicates the 4 peptide panel can provide moderate level of prediction accuracy but it is less than the 0.742 in the 2D-DIGE study. However, when considering the independent serum sample cohort and differences between the types of the two datasets (such as protein versus peptide, 2D-DIGE gel spots versus MRM), the difference of the AUC values does not exceed our expectation.

TABLE 3

MRM results of differentially expressed peptides between Gleason score 6 and 7 serum samples

| Protein | Peptide | p-value | q-value | Fold change |
|---|---|---|---|---|
| Kininogen-1 | IASFSQNCDIYPGK | 0 | 0.008 | 0.67 |
| Vitamin D-binding protein | SCESNSPFPVHPGTAECCTK | 0.001 | 0.01 | 0.73 |
| Antithrombin-III | TSDQIHFFFAK | 0.001 | 0.014 | 0.78 |
| Complement C4-A | GLEEELQFSLGSK | 0.002 | 0.015 | 0.71 |
| Protein AMBP | ETLLQDFR | 0.014 | 0.076 | 0.8 |
| Kininogen-1 | TVGSDTFYSFK | 0.022 | 0.084 | 0.76 |
| Inter-alpha-trypsin inhibitor heavy chain H4 | ILDDLSPR | 0.022 | 0.084 | 0.82 |
| Vitronectin | FEDGVLDPDYPR | 0.024 | 0.084 | 0.78 |
| Haptoglobin | TEGDGVYTLNNEK | 0.038 | 0.117 | 1.49 |
| Vitronectin | DVWGIEGPIDAAFTR | 0.052 | 0.126 | 0.76 |

TABLE 4

MRM results of differentially expressed peptides between non-ECE and ECE serum samples

| Protein | Peptide | p-value | q-value | Fold change |
|---|---|---|---|---|
| Zinc alpha-2-glycoprotein | HVEDVPAFQALGSLNDLQFFR | 0.000 | 0.011 | 1.44 |
| Kininogen-1 | IASFSQNCDIYPGK | 0.001 | 0.011 | 0.69 |
| Hemopexin | SGAQATVVTELPWPHEK | 0.004 | 0.044 | 0.84 |
| Serum albumin | FQNALLVR | 0.005 | 0.044 | 0.78 |
| Serotransferrin | YLGEEYVK | 0.007 | 0.051 | 0.80 |
| Complement C3 | SSLSVPYVIVPLK | 0.010 | 0.060 | 0.80 |
| Inter-alpha-trypsin inhibitor heavy chain H4 | ILDDLSPR | 0.015 | 0.070 | 0.79 |
| Antithrombin-III | TSDQIHFFFAK | 0.016 | 0.070 | 0.83 |
| Kininogen-1 | TVGSDTFYSFK | 0.018 | 0.070 | 0.79 |
| Serum albumin | LVNEVTEFAK | 0.021 | 0.072 | 0.84 |
| Apolipoprotein A-I | LLDNWDSVTSTFSK | 0.024 | 0.075 | 1.18 |
| Complement C4-A | GLEEELQFSLGSK | 0.033 | 0.088 | 0.82 |
| Pigment epithelium-derived factor | TVQAVLTVPK | 0.035 | 0.088 | 0.79 |
| Haptoglobin-related protein | VGYVSGWGQSDNFK | 0.040 | 0.093 | 0.76 |
| Inter-alpha-trypsin inhibitor heavy chain H4 | NVVFVIDK | 0.045 | 0.100 | 0.83 |
| Plasminogen | LSSPAVITDK | 0.049 | 0.101 | 0.81 |

In order to test if the AUC values obtained from the ROC curves are due to randomness, a permutation method was used to generate a null distribution of AUC value when the predictions are not associated with the patient grouping. The class labels were permutated 200 times and the predictions were made based on the permuted labels using PLS-DA method with 200 times bootstrapping. For predictions of non-ECE and ECE using the 4 peptides, Random Forests method was used instead. The AUC values shown in FIGS. 10 and 11 were compared with the null distribution and p-values were generated: Gleason score 6 and 7 (p-value=0), Gleason score 3+4 and 4+3 (p-value=0.19), non-ECE and ECE (p-value=0), non-ECE (GS 7) and ECE (GS7) (p-value=0), and non-ECE and ECE using 4 peptides (p-value=0.015). All the small p-values (except for Gleason score 3+4 and 4+3) indicate that the AUC values from the ROC curves were not due to random chance.

Discussion

The discovery and development of cancer biomarkers is a multiple-step process involving initial biomarker discovery, subsequent biomarker verification and validation. The characteristics of the task require different types of proteomics techniques to be applied in each phase. In a clinical proteomics study, label-free LC-MS/MS is more suitable for analysing large numbers of clinical specimens. The high sensitivity, large dynamic range and the ability to measure large numbers of protein targets have provided MRM with significant advantages in the verification and initial validation of biomarkers identified from high throughput proteomics studies. The approach of coupling label-free LC-MS/MS and MRM has been applied in studies for cancer biomarker discovery and verification. Using this approach, Whiteaker et al. identified osteopontin and fibulin-2 as a plasma biomarker for breast cancer in a mouse model (32). The study by Cima et al. identified glycoprotein biomarker signatures for predicting tissue PTEN status and diagnosis and grading of PCa (4). In this current study, we explored this approach in the discovery and verification of serum biomarkers for PCa grading and staging. Biomarker signatures of 32 proteins measured by MRM were shown to provide highly favorable prediction result for PCa diagnosis and prognosis.

In the label-free LC-MS/MS data analysis, only unique mapping peptides were considered in the differentially expression analysis. Although certain amount of information is loss from excluding ambiguous peptides, it can provide more confidence for the protein quantitation and the unique mapping peptides can serve as primary source for PTPs selection in the MRM development. Peptides were identified to be differentially expressed between different Gleason score and stages of the disease. However, the numbers of differentially expressed peptides detected are relative small. It is mostly likely due to the small sample size and the large variations observed in the LC-MS/MS data. There has been limited numbers of label-free LC-MS/MS experiment carried out on clinical serum samples. This is our first attempt to generate potential peptide targets as PCa biomarkers using label-free LC-MS/MS method. For future label-free LC-MS/MS experiments, some forms of internal standards like heavy labeled peptide mixtures can be spiked into each sample to account for between-run variations.

So far MRM assays have been developed for 32 proteins from the initial list. For the rest of the proteins on the list, highly confident MRM assays have not been developed. This is due to a number of reasons. First, we are limited by the availability of MS/MS data: not all of the proteins on the list have MS/MS data. Secondly, there may be sensitivity issues in detecting some of the low abundant proteins in crude serum samples, which may only be measured using fractionation method or by proteins/peptides enrichment methods such as SISCAPA. Thirdly, the use of dot product, RT regression has significantly reduced the false positives in the MRM peak selection but it also excluded some genuine MRM peaks and resulted in some false negatives. The most direct approach for MRM development is to use synthetic peptides combined with in-house MS/MS data collected from samples to which MRM assay will be applied. Isotopic labelled or non-labelled synthetic peptides can be used to collect MS/MS spectra for the 5 proteins which do not have MS/MS data and helps to identify the correct peak in the MRM results by coeluting with serum samples. A recently published MRM validation method—mProphet can also be applied to further validate the identified MRM transitions and provide FDR estimation (33).

Most of the proteins identified in this study likely represent body responses to tumour progression rather than directly originating from the tumour itself. In our initial verification results, the identified protein biomarkers were shown to be differentially expressed between different grades and stages of PCa. In particular, high predictive performance was observed by combining the 32 protein biomarkers into a signature, which indicates that those serum proteins can be used to improve cancer diagnosis and prognosis as successfully demonstrated by the OVA1 test for ovarian cancer (34).

In summary, MRM assays have been developed for the 32 potential serum biomarkers identified from the label-free LC-MS/MS experiment and published literatures. The developed MRM assay has been shown to be highly reproducible for both affinity depleted and crude serum samples (mean CV %<7%). The initial verification of the 32 proteins on 63 independent PCa serum samples has demonstrated the robustness of MRM as a quantitative method for measuring peptides/proteins in large number of crude serum samples. The 32 protein signature measured by MRM has shown highly favorable predictive performance for grading and staging of PCa. With careful validation on large patient cohort, this signature has the potential to improve PCa diagnosis and prognosis, which will help clinician and patients to select better treatment options.

SUPPLEMENTARY TABLE 1

Patient clinical information details for label-free LC-MS/MS experiment

| Hospital ID | Group | Age (years) | PSA (ng/mL) | PR Gleason Score | E.C.E. | S.V.I. | L.N.I. |
|---|---|---|---|---|---|---|---|
| MMH 92 | Gl5 | 66 | 8.5 | 3 + 2 | N | N | N |
| MMH 129 | Gl5 | 65 | 8.7 | 3 + 2 | N | N | N |
| MMH 163 | Gl5 | 56 | 9.8 | 2 + 3 | N | N | N |
| MMH 178 | Gl5 | 62 | 5.2 | 2 + 3 | N | N | N |
| MMH 195 | Gl5 | 64 | 7.7 | 2 + 3 | N | N | N |
| MMH 198 | Gl5 | 68 | 10.4 | 2 + 3 | N | N | N |

SUPPLEMENTARY TABLE 1-continued

Patient clinical information details for label-free LC-MS/MS experiment

| Hospital ID | Group | Age (years) | PSA (ng/mL) | PR Gleason Score | E.C.E. | S.V.I. | L.N.I. |
|---|---|---|---|---|---|---|---|
| MMH 246 | Gl5 | 58 | 7.7 | 3 + 2 | N | N | N |
| MMH 251 | Gl5 | 58 | 14 | 2 + 3 | N | N | N |
| MMH 279 | Gl5 | 53 | 21 | 3 + 2 | N | N | N |
| MMH 341 | Gl5 | 60 | 1.2 | 3 + 2 | N | N | N |
| MMH 100 | Gl7 | 70 | 5.9 | 3 + 4 | N | N | N |
| MMH 116 | Gl7 | 63 | 7 | 3 + 4 | N | N | N |
| MMH 148 | Gl7 | 57 | 4.6 | 3 + 4 | N | N | N |
| MMH 158 | Gl7 | 68 | 8.2 | 3 + 4 | N | N | N |
| MMH 169 | Gl7 | 66 | 15 | 3 + 4 | N | N | N |
| MMH 320 | Gl7 | 56 | 6.7 | 4 + 3 | N | N | N |
| MMH 324 | Gl7 | 56 | 7.5 | 4 + 3 | N | N | N |
| MMH 326 | Gl7 | 58 | 5.3 | 3 + 4 | N | N | N |
| MMH 353 | Gl7 | 68 | 9.3 | 3 + 4 | N | N | N |
| MMH 354 | Gl7 | 65 | 9.5 | 3 + 4 | N | N | N |
| MMH 104 | Gl7ECE | 55 | 6.5 | 4 + 3 | P | N | P |
| MMH 107 | Gl7ECE | 63 | 6.8 | 3 + 4 | P | N | N |
| MMH 126 | Gl7ECE | 65 | 6 | 3 + 4 | P | N | N |
| MMH 205 | Gl7ECE | 61 | 9.5 | 4 + 3 | P | N | N |
| MMH 208 | Gl7ECE | 64 | 5.9 | 3 + 4 | P | N | N |
| MMH 250 | Gl7ECE | 63 | 3.4 | 4 + 3 | P | N | N |
| MMH 263 | Gl7ECE | 57 | 7.5 | 4 + 3 | P | N | N |
| MMH 268 | Gl7ECE | 72 | 10 | 3 + 4 | P | N | N |
| MMH 287 | Gl7ECE | 61 | 13 | 3 + 4 | P | N | N |
| MMH 304 | Gl7ECE | 46 | 10 | 4 + 3 | P | N | N |

SUPPLEMENTARY TABLE 2

Patient clinical information details for MRM experiment

| Hospital ID | Group | Age (years) | PSA (ng/mL) | PR Gleason Score | E.C.E. | S.V.I. | L.N.I. |
|---|---|---|---|---|---|---|---|
| MMH 101 | Gl6 | 68 | 5.9 | 3 + 3 | N | N | N |
| MMH 110 | Gl6 | 67 | 5.97 | 3 + 3 | N | N | N |
| MMH 113 | Gl6 | 56 | 6.8 | 3 + 3 | N | N | N |
| MMH 124 | Gl6 | 55 | 8.3 | 3 + 3 | N | N | N |
| MMH 135 | Gl6 | 57 | 5 | 3 + 3 | N | N | N |
| MMH 136 | Gl6 | 66 | 11.6 | 3 + 3 | N | N | N |
| BH 14 | Gl6 | 60 | 1.3 | 3 + 3 | N | N | N |
| BH 16 | Gl6 | 64 | 5.7 | 3 + 3 | N | N | N |
| BH 17 | Gl6 | 64 | 6.8 | 3 + 3 | N | N | N |
| BH 24 | Gl6 | 66 | 8 | 3 + 3 | N | N | N |
| BH 25 | Gl6 | 58 | 12.5 | 3 + 3 | N | N | N |
| BH 28 | Gl6 | 53 | 5.8 | 3 + 3 | N | N | N |
| BH 31 | Gl6 | 56 | 12.7 | 3 + 3 | N | N | N |
| BH 33 | Gl6 | 55 | 7.2 | 3 + 3 | N | N | N |
| BH 39 | Gl6 | 58 | 8.3 | 3 + 3 | N | N | N |
| BH 42 | Gl6 | 62 | 9.8 | 3 + 3 | N | N | N |
| BH 61 | Gl6 | 55 | 10.6 | 3 + 3 | N | N | N |
| IMM 9 | Gl6 | 60 | 10 | 3 + 3 | N | N | N |
| IMM 10 | Gl6 | 64 | 8.3 | 3 + 3 | N | N | N |
| IMM 26 | Gl6 | 46 | 5 | 3 + 3 | N | N | N |
| IMM 92 | Gl6 | 58 | 5.92 | 3 + 3 | N | N | N |
| MMH 148 | Gl7 | 53 | 5.3 | 3 + 4 | N | N | N |
| MMH 152 | Gl7 | 58 | 6.7 | 3 + 4 | N | N | N |
| MMH 198 | Gl7 | 61 | 7.8 | 3 + 4 | N | N | N |
| MMH 381 | Gl7 | 57 | 5 | 3 + 4 | N | N | N |
| MMH 392 | Gl7 | 68 | 19.1 | 3 + 4 | N | N | N |
| MMH 393 | Gl7 | 47 | 2.7 | 3 + 4 | N | N | N |
| MMH 423 | Gl7 | 52 | 5.6 | 3 + 4 | N | N | N |
| BH 75 | Gl7 | 50 | 3.5 | 3 + 4 | N | N | N |
| BH 76 | Gl7 | 71 | 7.79 | 3 + 4 | N | N | N |
| BH 77 | Gl7 | 54 | 12.5 | 3 + 4 | N | N | N |
| BH 82 | Gl7 | 66 | 4.9 | 3 + 4 | N | N | N |
| MMH 69 | Gl7 | 66 | 6.5 | 4 + 3 | N | N | N |
| MMH 84 | Gl7 | 62 | 2.1 | 4 + 3 | N | N | N |
| MMH 138 | Gl7 | 64 | 7.5 | 4 + 3 | N | N | N |
| MMH 166 | Gl7 | 67 | 8.6 | 4 + 3 | N | N | N |
| MMH 200 | Gl7 | 61 | 14.6 | 4 + 3 | N | N | N |
| MMH 325 | Gl7 | 65 | 5.17 | 4 + 3 | N | N | N |
| MMH 332 | Gl7 | 65 | 6.6 | 4 + 3 | N | N | N |
| MMH 341 | Gl7 | 63 | 12.5 | 4 + 3 | N | N | N |

SUPPLEMENTARY TABLE 2-continued

Patient clinical information details for MRM experiment

| Hospital ID | Group | Age (years) | PSA (ng/mL) | PR Gleason Score | E.C.E. | S.V.I. | L.N.I. |
|---|---|---|---|---|---|---|---|
| MMH 401 | Gl7 | 67 | 18.1 | 4 + 3 | N | N | N |
| MMH 438 | Gl7 | 51 | 5.5 | 4 + 3 | N | N | N |
| BH 79 | Gl7 | 65 | 6.5 | 4 + 3 | N | N | N |
| MMH 82 | Gl7ECE | 67 | 5.5 | 3 + 4 | P | N | N |
| MMH 391 | Gl7ECE | 71 | 14.1 | 3 + 4 | P | N | N |
| MMH 398 | Gl7ECE | 66 | 2.1 | 3 + 4 | P | N | N |
| MMH 411 | Gl7ECE | 54 | 15 | 3 + 4 | P | N | N |
| MMH 428 | Gl7ECE | 66 | 5.7 | 3 + 4 | P | N | N |
| BH 13 | Gl7ECE | 64 | 5.9 | 3 + 4 | P | N | N |
| BH 27 | Gl7ECE | 65 | 7 | 3 + 4 | P | N | N |
| BH 37 | Gl7ECE | 64 | 4.1 | 3 + 4 | P | N | N |
| BH 59 | Gl7ECE | 66 | 14.2 | 3 + 4 | P | N | N |
| MMH 119 | Gl7ECE | 69 | 6.2 | 4 + 3 | P | N | N |
| MMH 149 | Gl7ECE | 47 | 8.9 | 4 + 3 | P | N | N |
| MMH 188 | Gl7ECE | 70 | 19.6 | 4 + 3 | P | N | N |
| MMH 206 | Gl7ECE | 65 | 10.2 | 4 + 3 | P | N | N |
| MMH 233 | Gl7ECE | 64 | 4.7 | 4 + 3 | P | N | N |
| MMH 237 | Gl7ECE | 62 | 10.6 | 4 + 3 | P | N | N |
| MMH 239 | Gl7ECE | 63 | 9.6 | 4 + 3 | P | N | N |
| MMH 305 | Gl7ECE | 66 | 5.1 | 4 + 3 | P | N | N |
| MMH 414 | Gl7ECE | 51 | 8.7 | 4 + 3 | P | N | N |
| MMH 415 | Gl7ECE | 67 | 17.8 | 4 + 3 | P | N | N |
| IMM 20 | Gl7ECE | 66 | 4 | 4 + 3 | P | N | N |

SUPPLEMENTARY TABLE 3

Differentially expressed peptides between Gleason score 5 and 7 identified from the volcano plot.

| Protein | Peptide | Charge | p-value | q-value | Fold change |
|---|---|---|---|---|---|
| Alpha-1-antitrypsin | DTEEEDFHVDQVTTVK | 2 | 0 | 0.07 | 2.41 |
| Alpha-1-antitrypsin | GTEAAGAMFLEAIPMSIPPEVK | 3 | 0.01 | 0.13 | 2.35 |
| Alpha-1-antitrypsin | LVDKFLEDVK | 3 | 0 | 0.09 | 2.3 |
| Alpha-1-antitrypsin | VFSNGADLSGVTEEAPLK | 2 | 0.01 | 0.13 | 2.32 |
| Alpha-1B-glycoprotein | LETPDFQLFK | 2 | 0.05 | 0.22 | 2.32 |
| Alpha-1-antichymotrypsin | EQLSLLDR | 2 | 0.03 | 0.21 | 2.75 |
| Alpha-1-antichymotrypsin | EQLSLLDRFTEDAK | 3 | 0 | 0.07 | 3.64 |
| Alpha-1-antichymotrypsin | LYGSEAFATDFQDSAAAK | 2 | 0.01 | 0.11 | 2.77 |
| Serum albumin | SHCIAEVENDEMPADLPSLAADFVESK | 3 | 0 | 0.05 | 0.29 |
| Serum albumin | VFDEFKPLVEEPQNLIK | 3 | 0 | 0.07 | 0.16 |
| Serum albumin | VFDEFKPLVEEPQNLIK | 3 | 0.01 | 0.12 | 0.31 |
| Serum albumin | VFDEFKPLVEEPQNLIK | 3 | 0.02 | 0.17 | 0.38 |
| Apolipoprotein A-IV | LGPHAGDVEGHLSFLEK | 4 | 0.01 | 0.12 | 4.37 |
| Apolipoprotein B-100 | FSVPAGIVIPSFQALTAR | 3 | 0.04 | 0.21 | 4.16 |
| Apolipoprotein B-100 | IADFELPTIIVPEQTIEIPSIK | 3 | 0.03 | 0.21 | 2.11 |
| Apolipoprotein B-100 | IADFELPTIIVPEQTIEIPSIK | 2 | 0.02 | 0.15 | 0.49 |
| Apolipoprotein B-100 | ITENDIQIALDDAK | 2 | 0 | 0.07 | 2.31 |
| Apolipoprotein B-100 | MTSNFPVDLSDYPK | 2 | 0.01 | 0.13 | 2.16 |
| Apolipoprotein B-100 | SVSLPSLDPASAK | 2 | 0.01 | 0.13 | 2.04 |
| Apolipoprotein B-100 | TILGTMPAFEVSLQALQK | 3 | 0.04 | 0.21 | 2.74 |

SUPPLEMENTARY TABLE 3-continued

Differentially expressed peptides between Gleason score 5 and 7 identified from the volcano plot.

| Protein | Peptide | Charge | p-value | q-value | Fold change |
|---|---|---|---|---|---|
| Apolipoprotein B-100 | VIGNMGQTMEQLTPELK | 2 | 0.03 | 0.2 | 2.33 |
| Apolipoprotein B-100 | VPSYTLILPSLELPVLHVPR | 3 | 0.04 | 0.21 | 13.94 |
| Apolipoprotein B-100 | VPSYTLILPSLELPVLHVPR | 4 | 0.05 | 0.22 | 5.03 |
| Apolipoprotein E | GEVQAMLGQSTEELR | 2 | 0 | 0.08 | 2.49 |
| Apolipoprotein E | GEVQAMLGQSTEELR | 3 | 0.01 | 0.12 | 3.46 |
| Complement factor H | GEWVALNPLR | 2 | 0.04 | 0.21 | 2.21 |
| Complement factor H | NTEILTGSWSDQTYPEGTQAIYK | 2 | 0.03 | 0.21 | 2.44 |
| Complement C3 | EGVQKEDIPPADLSDQVPDTESETR | 3 | 0 | 0.04 | 2.62 |
| Complement C4-B | LLLFSPSVVHLGVPLSVGVQLQDVPR | 4 | 0.04 | 0.21 | 4.19 |
| Complement C4-B | VGDTLNLNLR | 2 | 0 | 0.07 | 2.09 |
| Complement C5 | IPLDLVPK | 2 | 0.02 | 0.17 | 3.47 |
| Complement component C9 | GTVIDVTDFVNWASSINDAPVLISQK | 4 | 0.02 | 0.17 | 3.09 |
| Fibronectin | DLQFVEVTDVK | 2 | 0.02 | 0.16 | 2 |
| Hemoglobin subunit beta | FFESFGDLSTPDAVMGNPK | 2 | 0 | 0.08 | 0.21 |
| Hemoglobin subunit beta | VNVDEVGGEALGR | 2 | 0.01 | 0.13 | 0.35 |
| Hemopexin | SGAQATWTELPWPHEK | 2 | 0 | 0.07 | 2.06 |
| Hemopexin | SGAQATWTELPWPHEK | 2 | 0.04 | 0.21 | 2.4 |
| Histidine-rich glycoprotein | GGEGTGYFVDFSVR | 2 | 0.04 | 0.21 | 2.08 |
| Inter-alpha-trypsin inhibitor heavy chain H1 | TMEQFTIHLTVNPQSK | 3 | 0.04 | 0.21 | 2.09 |
| Inter-alpha-trypsin inhibitor heavy chain H2 | AEDHFSVIDFNQNIR | 3 | 0.01 | 0.12 | 2.51 |
| Inter-alpha-trypsin inhibitor heavy chain H2 | MLADAPPQDPSCCSGALYYGSK | 2 | 0 | 0.07 | 2.41 |
| Inter-alpha-trypsin inhibitor heavy chain H2 | TILDDLR | 2 | 0.03 | 0.2 | 2.49 |
| Inter-alpha-trypsin inhibitor heavy chain H4 | ANTVQEATFQMELPK | 2 | 0.05 | 0.22 | 2.15 |
| Inter-alpha-trypsin inhibitor heavy chain H4 | QGPVNLLSDPEQGVEVTGQYER | 2 | 0.03 | 0.2 | 2.15 |
| Lumican | LPSGLPVSLLTLYLDNNK | 3 | 0.03 | 0.2 | 2.18 |
| Plasminogen | VILGAHQEVNLEPHVQEIEVSR | 4 | 0.02 | 0.15 | 7.33 |
| Prothrombin | GQPSVLQVVNLPIVERPVCK | 3 | 0 | 0.09 | 2.31 |
| Prothrombin | ITDNMFCAGYKPDEGKR | 4 | 0 | 0.07 | 2.17 |
| Prothrombin | SEGSSVNLSPPLEQCVPDR | 2 | 0.03 | 0.21 | 2.22 |
| Prothrombin | TFGSGEADCGLRPLFEK | 3 | 0 | 0.07 | 2.04 |
| Vitamin D-binding protein | KFPSGTFEQVSQLVK | 3 | 0 | 0.07 | 2.96 |

SUPPLEMENTARY TABLE 4

Differentially expressed peptides between NECE and ECE identified from the volcano plot.

| Protein | Peptide | Charge | p-value | q-value | Fold change |
|---|---|---|---|---|---|
| Alpha-1B-glycoprotein | LETPDFQLFK | 2 | 0.02 | 0.67 | 2.03 |
| Serum albumin | VPQVSTPTLVEVSR | 3 | 0.02 | 0.67 | 0.38 |
| Serum albumin | FKDLGEENFK | 3 | 0.01 | 0.58 | 0.38 |
| Serum albumin | VFDEFKPLVEEPQNLIK | 3 | 0.04 | 0.67 | 0.36 |
| Serum albumin | VFDEFKPLVEEPQNLIK | 3 | 0.04 | 0.67 | 0.31 |
| Serum albumin | KVPQVSTPTLVEVSR | 2 | 0.02 | 0.67 | 0.11 |
| Serum albumin | FQNALLVR | 2 | 0.03 | 0.67 | 0.24 |
| Serum albumin | KQTALVELVK | 3 | 0.03 | 0.67 | 0.32 |
| Serum albumin | LVNEVTEFAK | 2 | 0.00 | 0.20 | 0.47 |
| Serum albumin | QTALVELVK | 2 | 0.00 | 0.50 | 0.35 |
| Serum albumin | SHCIAEVENDEMPADLPSLAADFVESK | 3 | 0.04 | 0.67 | 0.33 |
| Serum albumin | KVPQVSTPTLVEVSR | 3 | 0.01 | 0.66 | 0.47 |
| Apolipoprotein A-II | AGTELVNFLSYFVELGTQPATQ | 3 | 0.00 | 0.00 | 2.60 |
| Apolipoprotein B-100 | IADFELPTIIVPEQTIEIPSIK | 2 | 0.02 | 0.67 | 0.40 |
| Apolipoprotein B-100 | VIGNMGQTMEQLTPELK | 3 | 0.01 | 0.60 | 2.18 |
| Apolipoprotein B-100 | VIGNMGQTMEQLTPELK | 2 | 0.02 | 0.67 | 2.13 |
| Complement C4-B | VGLSGMAIADVTLLSGFHALR | 3 | 0.01 | 0.67 | 0.34 |
| Complement C4-B | DFALLSLQVPLKDAK | 3 | 0.04 | 0.67 | 0.26 |
| Complement C5 | TDAPDLPEENQAR | 2 | 0.03 | 0.67 | 0.50 |
| Hemoglobin subunit alpha | VGAHAGEYGAEALER | 2 | 0.05 | 0.67 | 0.42 |
| Hemoglobin subunit alpha | VGAHAGEYGAEALER | 3 | 0.04 | 0.67 | 0.46 |
| Hemoglobin subunit beta | VNVDEVGGEALGR | 2 | 0.02 | 0.67 | 0.38 |
| Heparin cofactor 2 | GGETAQSADPQWEQLNNK | 2 | 0.04 | 0.67 | 0.49 |
| Ig kappa chain C region | VDNALQSGNSQESVTEQDSK | 3 | 0.02 | 0.67 | 0.28 |

SUPPLEMENTARY TABLE 5

A list of 64 proteins were selected for MRM development based on results from the 2D-DIGE, label-free LC-MS/MS studies and published literatures. The serum protein concentrations are based on Hortin et al.

| Uniprot accession | Protein Name | 2D-DIGE | Label-free | Literature | Reference Concentration (umol/L) |
|---|---|---|---|---|---|
| P01009 | Alpha-1-antitrypsin | Yes | Yes | Yes | 18-40 |
| P01011 | Alpha-1-antichymotrypsin | Yes | Yes | | 4-9 |
| P01023 | Alpha-2-macroglobulin | Yes | | Yes | 7-17 |
| P12429 | Annexin A3 | | | Yes | NA. |
| Q6IWH7 | Anoctamin-7 | | | Yes | NA. |
| P01008 | Antithrombin-III | Yes | | | 3-5 |
| P02647 | Apolipoprotein A-I | Yes | Yes | Yes | 30-70 |
| P02652 | Apolipoprotein A-II | Yes | Yes | Yes | 30-60 |
| P06727 | Apolipoprotein A-IV | Yes | Yes | Yes | 3-6 |
| P02656 | Apolipoprotein C-III | Yes | | Yes | 6-20 |
| P05090 | Apolipoprotein D | | | Yes | NA. |
| P02649 | Apolipoprotein E | Yes | Yes | Yes | 0.6-2 |
| Q96KN2 | Beta-Ala-His dipeptidase | | | Yes | NA. |
| Q03135 | Caveolin-1 | | | Yes | NA. |
| O43866 | CD5 antigen-like | Yes | | | NA. |
| P10645 | Chromogranin-A | | | Yes | NA. |
| P10909 | Clusterin | Yes | | Yes | 1-2 |
| P00748 | Coagulation factor XII | Yes | | | NA. |

SUPPLEMENTARY TABLE 5-continued

A list of 64 proteins were selected for MRM development based on results from the 2D-DIGE, label-free LC-MS/MS studies and published literatures. The serum protein concentrations are based on Hortin et al.

| Uniprot accession | Protein Name | 2D-DIGE | Label-free | Literature | Reference Concentration (umol/L) |
|---|---|---|---|---|---|
| P05160 | Coagulation factor XIII B chain | Yes | | | NA. |
| P02746 | Complement C1q subcomponent subunit B | Yes | | Yes | NA. |
| P00736 | Complement C1r subcomponent | Yes | | Yes | NA. |
| P01024 | Complement C3 | Yes | Yes | | 5-10 |
| P0C0L4 | Complement C4-A/B | Yes | Yes | | 0.5-2 |
| P13671 | Complement component C6 | Yes | | | 0.5-0.9 |
| P02748 | Complement component C9 | | Yes | | 0.4-1 |
| P08603 | Complement factor H | Yes | Yes | Yes | NA. |
| Q03591 | Complement factor H-related protein 1 | Yes | | | NA. |
| P36980 | Complement factor H-related protein 2 | Yes | | | NA. |
| P17813 | Endoglin | | | Yes | NA. |
| O75636 | Ficolin-3 | Yes | | Yes | 0.2-0.7 |
| Q08380 | Galectin-3-binding protein | | | Yes | NA. |
| P22352 | Glutathione peroxidase 3 | Yes | | | NA. |
| P00738 | Haptoglobin | Yes | | Yes | 6-40 |
| P00739 | Haptoglobin-related protein | Yes | | | 0.6-1.2 |
| P02790 | Hemopexin | Yes | Yes | | 9-20 |
| P15516 | Histatin 3 | Yes | | | NA. |
| P01834 | Ig kappa chain C region | Yes | | Yes | NA. |
| P01871 | Ig mu chain C region | Yes | | Yes | NA. |
| P08069 | Insulin-like growth factor 1 receptor | | | Yes | NA. |
| P01343 | Insulin-like growth factor IA | | | Yes | NA. |
| P17936 | Insulin-like growth factor-binding protein 3 | | | Yes | 0.07-0.17 |
| Q16270 | Insulin-like growth factor-binding protein 7 | | | Yes | NA. |
| Q14624 | Inter-alpha-trypsin inhibitor heavy chain H4 | Yes | Yes | | 1-2 |
| P05231 | Interleukin-6 | | | Yes | NA. |
| Q9UBX7 | Kallikrein-11 | | | Yes | NA. |
| P01042 | Kininogen-1 | Yes | | | 3 |
| P02750 | Leucine rich α-2-glycoprotein | Yes | | | 0.4 |
| P08571 | Monocyte differentiation antigen CD14 | | | Yes | NA. |
| P36955 | Pigment epithelium-derived factor | Yes | | Yes | 0.1 |
| P00747 | Plasminogen | | Yes | | 2-4 |
| Q9GZY1 | Prostate and breast cancer overexpressed gene 1 protein | | | Yes | NA. |
| P07288 | Prostate-specific antigen | | | Yes | NA. |
| P15309 | Prostatic acid phosphatase | | | Yes | NA. |
| P28072 | Proteasome subunit beta type-6 | Yes | | | NA. |
| P02760 | Protein AMBP | Yes | | | NA. |
| P02787 | Serotransferrin | Yes | | | 25-45 |
| P02768 | Serum albumin | Yes | Yes | | 500-800 |
| P02743 | Serum amyloid P-component | Yes | | Yes | 1-2 |
| P01137 | Transforming growth factor beta-1 | | | Yes | NA. |
| P15692 | Vascular endothelial growth factor A | | | Yes | NA. |
| O43915 | Vascular endothelial growth factor D | | | Yes | NA. |
| P02774 | Vitamin D-binding protein | Yes | Yes | Yes | NA. |
| P04004 | Vitronectin | Yes | | | 1-3 |
| P25311 | Zinc alpha-2-glycoprotein | Yes | | Yes | 0.8-1.6 |

REFERENCES

1. Jemal, A., Siegel, R., Ward, E., Hao, Y., Xu, J., and Thun, M. J. (2009) Cancer Statistics, 2009. *CA Cancer J Clin* 59, 225-249.
2. Ferlay, J., Parkin, D. M., and Steliarova-Foucher, E. (2008) Estimates of cancer incidence and mortality in Europe in 2008. *European Journal of Cancer* 46, 765-781.
3. Hughes, C., Murphy, A., Martin, C., Sheils, O., and O'Leary, J. (2005) Molecular pathology of prostate cancer. *Journal of Clinical Pathology* 58: 673-684.
4. Cima, I., Schiess, R., Wild, P., Kaelin, M., Schüffler, P., Lange, V., Picotti, P., Ossola, R., Templeton, A., Schubert, O., Fuchs, T., Leippold, T., Wyler, S., Zehetner, J., Jochum, W., Buhmann, J., Cerny, T., Moch, H., Gillessen, S., Aebersold, R., and Krek, W. (2011) Cancer genetics-guided discovery of serum biomarker signatures for diagnosis and prognosis of prostate cancer. *Proceedings of the National Academy of Sciences* 108, 3342-3347.
5. Lau, T. Y. K., Power, K. A., Dijon, S., de Gardelle, I., McDonnell, S., Duffy, M. J., Pennington, S. R., and Gallagher, W. M. (2009) Prioritization of Candidate Protein Biomarkers from an In Vitro Model System of Breast Tumor Progression Toward Clinical Verification. *Journal of Proteome Research* 9, 1450-1459.
6. Pang, J., Liu, W.-P., Liu, X.-P., Li, L.-Y., Fang, Y.-Q., Sun, Q.-P., Liu, S.-J., Li, M.-T., Su, Z.-L., and Gao, X. (2009) Profiling Protein Markers Associated with Lymph Node Metastasis in Prostate Cancer by DIGE-based Proteomics Analysis. *Journal of Proteome Research* 9, 216-226.
7. Lin, B., White, J. T., Lu, W., Xie, T., Utleg, A. G., Yan, X., Yi, E. C., Shannon, P., Khrebtukova, I., Lange, P. H., Goodlett, D. R., Zhou, D., Vasicek, T. J., and Hood, L. (2005) Evidence for the Presence of Disease-Perturbed Networks in Prostate Cancer Cells by Genomic and Proteomic Analyses: A Systems Approach to Disease. *Cancer Research* 65, 3081-3091.
8. Anderson, N. L., and Anderson, N. G. (2002) The Human Plasma Proteome. *Molecular & Cellular Proteomics* 1, 845-867.
9. Byrne, J. C., Downes, M. R., O'Donoghue, N., O'Keane, C., O'Neill, A., Fan, Y., Fitzpatrick, J. M., Dunn, M. J., and Watson, R. W. G. (2008) 2D-DIGE as a Strategy To Identify Serum Markers for the Progression of Prostate Cancer. *Journal of Proteome Research* 8, 942-957.
10. Adam, B.-L., Qu, Y., Davis, J. W., Ward, M. D., Clements, M. A., Cazares, L. H., Semmes, O. J., Schellhammer, P. F., Yasui, Y., Feng, Z., and Wright, G. L. (2002) Serum Protein Fingerprinting Coupled with a Pattern-matching Algorithm Distinguishes Prostate Cancer from Benign Prostate Hyperplasia and Healthy Men. *Cancer Research* 62, 3609-3614.
11. Petricoin, E. F., III, Ornstein, D. K., Paweletz, C. P., Ardekani, A., Hackett, P. S., Hitt, B. A., Velassco, A., Trucco, C., Wiegand, L., Wood, K., Simone, C. B., Levine, P. J., Linehan, W. M., Emmert-Buck, M. R., Steinberg, S. M., Kohn, E. C., and Liotta, L. A. (2002) Serum Proteomic Patterns for Detection of Prostate Cancer. *J. Natl. Cancer Inst.* 94, 1576-1578.
12. Lionel L, B., Premkala, P., Leon, S. U. N., Amina, A. L. I., Zhigiang, Z. O. U., Bao-Ling, A., McLEOD, D. G., Judd W, M., and Shiv, S. (2003) Diagnostic Potential of Serum Proteomic Patterns in Prostate Cancer. *The Journal of urology* 170, 442-446.
13. David K, O., Walter, R., Vincent A, F., Thomas P, C., Sally J, R., Ben A, H., Wesley W, W., Timothy D, V., Lance A, L., and Emanuel F, P. (2004) Serum proteomic profiling can discriminate prostate cancer from benign prostates in men with total prostate specific antigen levels between 2.5 and 15.0 ng/ml. *The Journal of urology* 172, 1302-1305.
14. Skytt, A., Thysell, E., Stattin, P., Stenman, U.-H., Antti, H., and Wikstrom, P. (2007) SELDI-TOF MS versus prostate specific antigen analysis of prospective plasma samples in a nested case-control study of prostate cancer. *International Journal of Cancer* 121, 615-620.
15. Nanni, P., Levander, F., Roda, G., Caponi, A., James, P., and Roda, A. (2009) A label-free nano-liquid chromatography-mass spectrometry approach for quantitative serum peptidomics in Crohn's disease patients. *Journal of Chromatography B* 877, 3127-3136.
16. Negishi, A., Ono, M., Handa, Y., Kato, H., Yamashita, K., Honda, K., Shitashige, M., Satow, R., Sakuma, T., Kuwabara, H., Omura, K., Hirohashi, S., and Yamada, T. (2009) Large-scale quantitative clinical proteomics by label-free liquid chromatography and mass spectrometry. *Cancer Science* 100, 514-519.
17. Ono, M., Shitashige, M., Honda, K., Isobe, T., Kuwabara, H., Matsuzuki, H., Hirohashi, S., and Yamada, T. (2006) Label-free Quantitative Proteomics Using Large Peptide Data Sets Generated by Nanoflow Liquid Chromatography and Mass Spectrometry. *Molecular & Cellular Proteomics* 5, 1338-1347.
18. Pan, J., Chen, H.-Q., Sun, Y.-H., Zhang, J.-H., and Luo, X.-Y. (2008) Comparative Proteomic Analysis of Non-small-cell Lung Cancer and Normal Controls Using Serum Label-Free Quantitative Shotgun Technology. *Lung* 186, 255-261.
19. Piersma, S. R., Fiedler, U., Span, S., Lingnau, A., Pham, T. V., Hoffmann, S., Kubbutat, M. H. G., and Jiménez, C. R. (2010) Workflow Comparison for Label-Free, Quantitative Secretome Proteomics for Cancer Biomarker Discovery: Method Evaluation, Differential Analysis, and Verification in Serum. *Journal of Proteome Research* 9, 1913-1922.
20. Billingsley, M. L., Pennypacker, K. R., Hoover, C. G., Brigati, D. J., and Kincaid, R. L. (1985) A rapid and sensitive method for detection and quantification of calcineurin and calmodulin-binding proteins using biotinylated calmodulin. *Proceedings of the National Academy of Sciences of the United States of America* 82, 7585-7589.
21. Candiano, G., Bruschi, M., Musante, L., Santucci, L., Ghiggeri, G. M., Carnemolla, B., Orecchia, P., Zardi, L., and Righetti, P. G. (2004) Blue silver: A very sensitive colloidal Coomassie G-250 staining for proteome analysis. *ELECTROPHORESIS* 25, 1327-1333.
22. Kessner, D., Chambers, M., Burke, R., Agus, D., and Mallick, P. (2008) ProteoWizard: open source software for rapid proteomics tools development. *Bioinformatics* 24, 2534-2536.
23. Deutsch, E. W., Mendoza, L., Shteynberg, D., Farrah, T., Lam, H., Tasman, N., Sun, Z., Nilsson, E., Pratt, B., Prazen, B., Eng, J. K., Martin, D. B., Nesvizhskii, A. I., and Aebersold, R. (2010) A guided tour of the Trans-Proteomic Pipeline. *PROTEOMICS* 10, 1150-1159.
24. Keller, A., Nesvizhskii, A. I., Kolker, E., and Aebersold, R. (2002) Empirical Statistical Model To Estimate the Accuracy of Peptide Identifications Made by MS/MS and Database Search. *Analytical Chemistry* 74, 5383-5392.
25. MacLean, B., Tomazela, D. M., Shulman, N., Chambers, M., Finney, G. L., Frewen, B., Kern, R., Tabb, D. L., Liebler, D. C., and MacCoss, M. J. (2010) Skyline: an open source document editor for creating and analyzing targeted proteomics experiments. *Bioinformatics* 26, 966-968.
26. Peng, J., Elias, J. E., Thoreen, C. C., Licklider, L. J., and Gygi, S. P. (2002) Evaluation of Multidimensional Chromatography Coupled with Tandem Mass Spectrometry (LC/LC-MS/MS) for Large-Scale Protein Analysis: The Yeast Proteome. *Journal of Proteome Research* 2, 43-50.
27. Hortin, G. L., Sviridov, D., and Anderson, N. L. (2008) High-Abundance Polypeptides of the Human Plasma Proteome Comprising the Top 4 Logs of Polypeptide Abundance. *Clin Chem* 54, 1608-1616.
28. Sherwood, C. A., Eastham, A., Lee, L. W., Risler, J., Vitek, O., and Martin, D. B. (2009) Correlation between y-Type Ions Observed in Ion Trap and Triple Quadrupole Mass Spectrometers. *Journal of Proteome Research* 8, 4243-4251.
29. Hanchette, C. L., and Schwartz, G. G. (1992) Geographic patterns of prostate cancer mortality. Evidence for a protective effect of ultraviolet radiation. *Cancer* 70, 2861-2869.
30. Schwartz, G. G., and Hulka, B. S. (1990) Is vitamin D deficiency a risk factor for prostate cancer? (hypothesis). *Anticancer Research* 10, 1307-1311.
31. Byrne, J. C., Downes, M. R., O'Donoghue, N., O'Keane, C., O'Neill, A., Fan, Y., Fitzpatrick, J. M., Dunn, M. J., and Watson, R. W. G. (2009) 2D-DIGE as a Strategy To Identify Serum Markers for the Progression of Prostate Cancer. *Journal of Proteome Research* 8, 942-957.
32. Whiteaker, J. R., Zhang, H., Zhao, L., Wang, P., Kelly-Spratt, K. S., Ivey, R. G., Piening, B. D., Feng, L.-C., Kasarda, E., Gurley, K. E., Eng, J. K., Chodosh, L. A., Kemp, C. J., McIntosh, M. W., and Paulovich, A. G. (2007) Integrated Pipeline for Mass Spectrometry-Based Discovery and Confirmation of Biomarkers Demonstrated in a Mouse Model of Breast Cancer. *Journal of Proteome Research* 6, 3962-3975.
33. Reiter, L., Rinner, O., Picotti, P., Huttenhain, R., Beck, M., Brusniak, M.-Y., Hengartner, M. O., and Aebersold, R. (2011) mProphet: automated data processing and statistical validation for large-scale SRM experiments. *Nat Meth* 8, 430-435.
34. Fung, E. T. (2010) A Recipe for Proteomics Diagnostic Test Development: The OVA1 Test, from Biomarker Discovery to FDA Clearance. *Clin Chem* 56, 327-329.

Additional Blinded Validation of the Panel 116 serum samples were received from the PCRC biobank with samples from "significant" (OC), "aggressive" (NOC) and "indolent" (OC) disease patients that included patients with organ confined (OC) and non-organ confined disease NOC). An in-house laboratory number was given to the samples and the preparation of all 116 samples for mass spectrometry analysis was undertaken. Briefly, samples were aliquoted, protein concentration measured by Nanodrop and then serum equivalent to 100 ug protein was digested with trypsin according to a standard operating procedure (SOP_SP_4; see below).

Digested samples were run in a randomised order in batches of 24 samples. A reference pool sample was run at the start (twice), middle (twice) and end (once) of each batch to measure instrument signal response within a batch and also from batch to batch.

Samples were run once with the original MRM method for the proteins from List A not including Caveolin-1 (Method A/Yue Fan Method) for all 5 batches. The mass spectrometry analysis took place from the 18 Nov. 2013 and ran uninterrupted until the 13 Dec. 2013. Analysis of raw MS data was undertaken using Skyline software (64 bit, Version 2.1.0.4936).

So, the dataset analysed came from the measurement of 53 peptides over 116 patients. Of the 116, 34 were subsequently unblinded and had "indolent" disease, 34 had "significant" disease and the remaining 48 had "aggressive" disease. Throughout the experiment a number of "refpool" samples were run which measured the same 53 peptides as those measured in the biological samples. These 'refpool' samples are not biological samples and were included as a means of measuring the reproducibility of the experiment and calculating the technical variability of the experiment due to machine, sample preparation and batch to batch variation. The samples were randomised before being subjected to the mass spectrometer and the experiment was carried out over 5 batches. Within each batch, 5 refpool samples were run (2 at the beginning, 2 in the middle and 1 at the end) in order to measure the technical variability both within and between batches. Sample and run order information can be seen in Appendix 1.

The data presented for analysis were the transition areas as measured by Skyline for the top three transitions over each of the peptides. In order to analyse the data two approaches were undertaken. The first was to analyse the data based on the highest ranked transition for each peptide, the second was to take the sum of the top three transition areas for each peptide.

Highest Ranked Transition

In order to ensure that the same peptide transition was being measured across samples the transition with the highest rank (according to Skyline's "Library Rank") was chosen for each peptide. This ensured that the transitions being measured were consistent for each of the samples compared. The reason for this is because it is feasible that the transition with the highest area abundance might not correspond to the same transition across samples.

Missing Information

Figure 14:
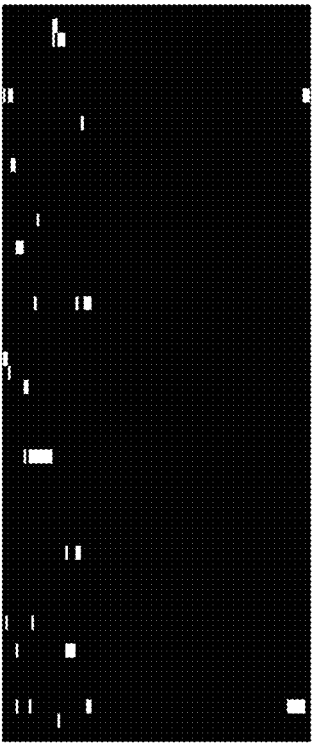
FIG. 14. Missing Data plot for each of the variables measured over the 118 samples. SEQ ID NOs. for each of the peptides listed from top to bottom are: 44, 28, 16, 20, 30, 17, 31, 23, 40, 41, 37, 8, 26, 29, 4, 21, 33, 25, 12, 49, 48, 35, 32, 7, 45, 1, 27, 3, 10, 36, 13, 38, 52, 15, 24, 46, 34, 51, 43, 11, 19, 5, 2, 9, 50, 42, 47, 39, 22, 14, 18, 105 and 6 respectively.

After taking the highest ranked transition for each peptide, it was noted that there were some missing values across 17 of the peptides. FIG. 14 shows a graph of the missingness patterns evidenced in the data, here black indicates an observed value in the dataset and white a missing value. As can be seen the vast majority of the data are observed.

In order to account for the missingness in the data and not bias the results it was decided to impute missing values were imputed to using predictive mean matching. Here each missing variable is modelled (using multiple linear models) and for each predicted value the value that is imputed is the nearest observed value in the dataset to the predicted value. This ensures that the imputed values are plausible and observable. Here imputation was only performed once, in future analyses it would be interesting to perform multiple imputation and see the variability of the overall results due to the uncertainty of the imputed values through the use of generalised linear models. This equates to performing multiple Bayesian linear models with each missing variable in turn as the response and the remaining variables as the predictors.

Figure 15:
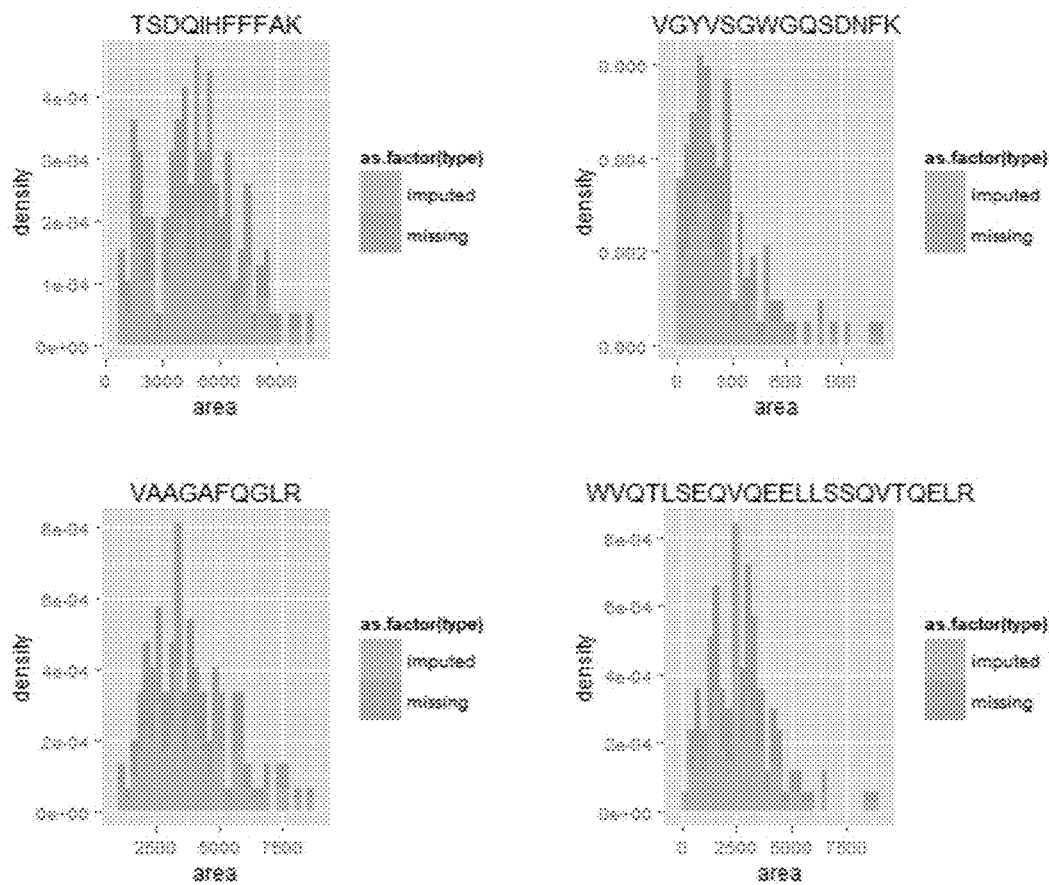
FIG. 15. Histogram of observed data with missing values (blue) compared to imputed data. The peptides shown (in the order top left, top right, bottom left, bottom right) correspond to SEQ ID NOs. 8, 31, 40 and 16 respectively.

To ensure that the imputed values are reasonable the distribution of each variable's observed values was compared to the distribution of the observed plus the imputed values. FIG. 15 shows a histogram of the data with missing values compared to the data with imputed value for four peptides with missing data. As can be seen the distribution of the imputed data in all cases follows the same pattern as the data with missing values, this confirms that the imputed values are reasonable given the data that have been observed and don't appear to be skewing the distribution of the variables (See FIG. 22A-D for images across all 19 missing variables).

Prediction Accuracy

Figure 16:
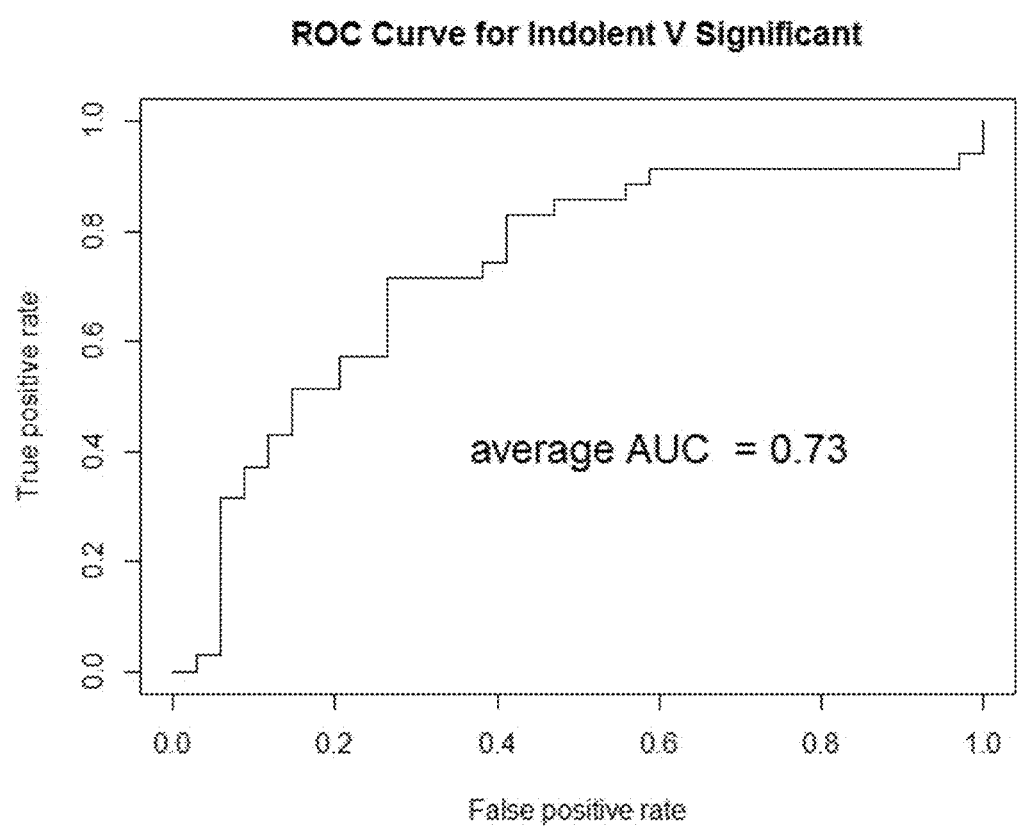
FIG. 16. Average AUC over 100 iterations of random forest for Indolent Versus Significant patients FIG. 17. Average ranked variable importance of the top 30 peptides for indolent versus significant disease. SEQ ID NOs. for each of the peptides listed from top to bottom are: 5, 6, 9, 8, 40, 31, 39, 26, 43, 19, 22, 47, 12, 32, 33, 10, 4, 38, 3, 44, 49, 42, 45, 7, 28, 15, 16, 51, 14 and 30 respectively.

Once the data missing data were appropriately handled a random forest was run using package randomForest in R 3.0.1. The random forest algorithm builds each decision tree based on a different subset of the data by taking multiple bootstrap samples (sample with replacement) of observations and variables. For each decision tree in the random forest algorithm, the observations that were not used to build the tree are used to validate it. This means that the random forest algorithm is unique in that it gives automatic access to a cross validated misclassification rate and cross validated AUC values can easily be computed. These AUC values can then be used to assess how accurately the given biomarker panel would be expected to perform on a separate cohort of patients. The random forest is also especially suited to the purpose of biomarker selection as it also gives a variable importance score for each peptide used in the model. This can be used to see how important each peptide was in giving the overall AUC score. Here three models were of interest for the panel of 53 peptides to predict between:

1. "Indolent" and "Significant" patients
2. "Indolent" and "Aggressive" patients
3. "Significant" and "Aggressive" patients Indolent Versus Significant The first model fit was to predict between patients that had indolent versus significant disease. To ensure that the results were consistent across multiple runs of the random forest, the algorithm was run 100 times. The average AUC over the 100 iterations of the random forest was 0.73 (see FIG. 16).

Figure 17:
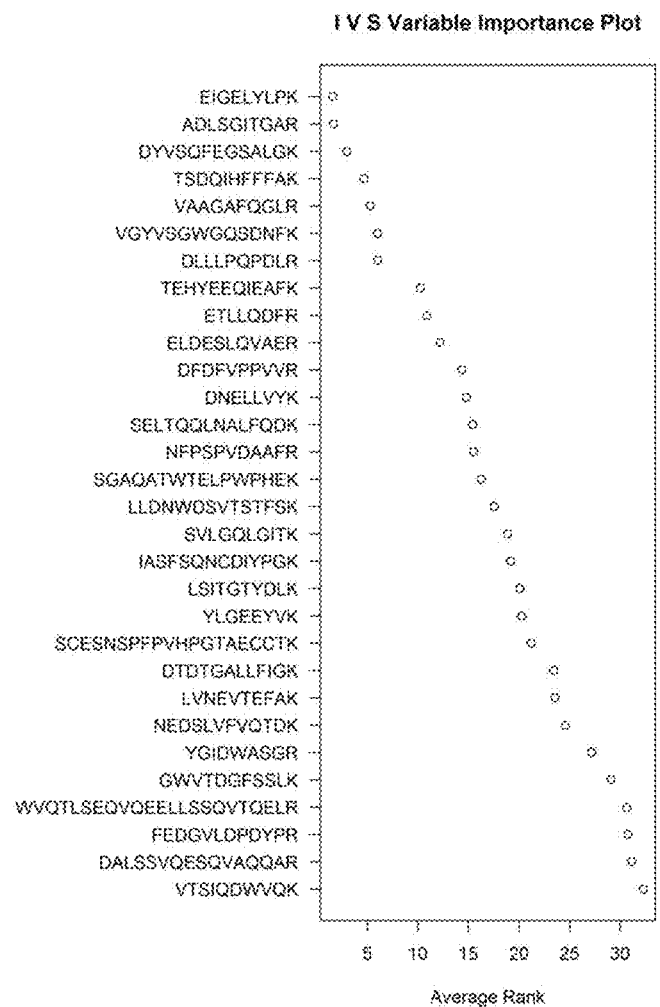

FIG. 17 shows the importance of the top 30 variables according to the random forest models where the importance should be read from top to bottom i.e. variables that appear at the top of the plot are more important than those that appear at the bottom.

Indolent Versus Aggressive

Figure 18:
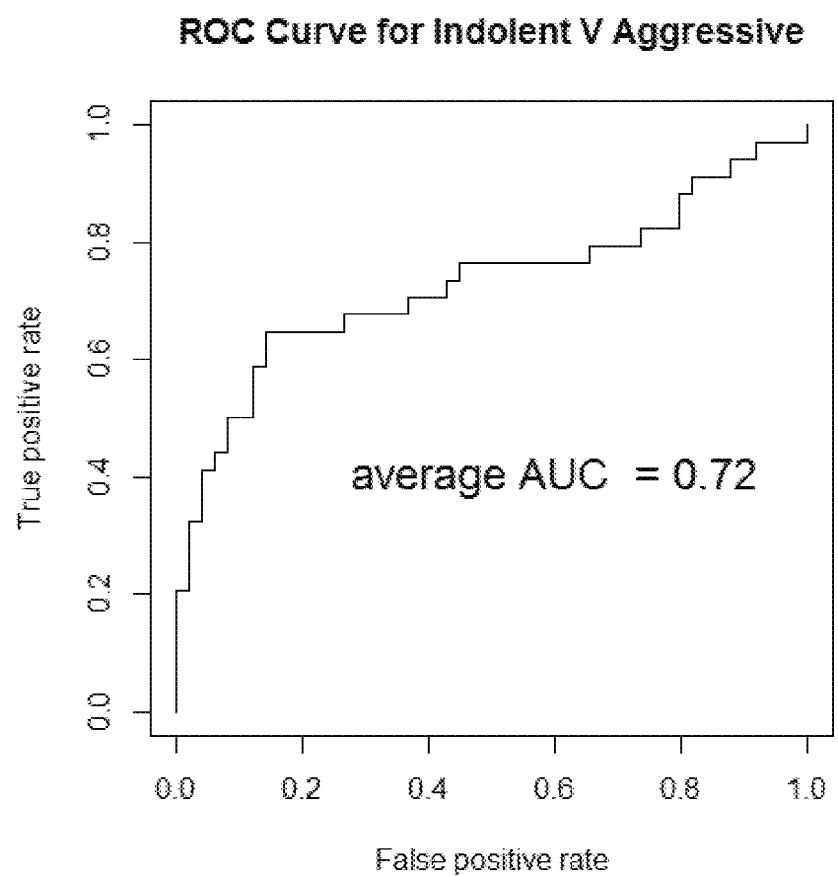
FIG. 18. Average AUC over 100 iterations of random forest for Indolent Versus Aggressive patients FIG. 19. Average ranked variable importance of the top 30 peptides for indolent versus aggressive disease. SEQ ID NOs. for each of the peptides listed from top to bottom are: 6, 8, 43, 10, 47, 11, 33, 7, 22, 29, 28, 19, 16, 30, 5, 13, 42, 48, 14, 21, 51, 27, 52, 23, 4, 50, 105, 49, 31 and 15 respectively.

The same analysis was repeated for indolent versus aggressive disease and it was found that over an average of 100 iterations the random forest model performed roughly the same as for indolent versus significant disease with an average AUC of 0.72 (See FIG. 18). This model has much higher sensitivity than it does specificity. The sensitivity of this model was 0.89 meaning that of the patients that actually had aggressive disease on average they were correctly identified 89% of the time are being aggressive.

Figure 19:
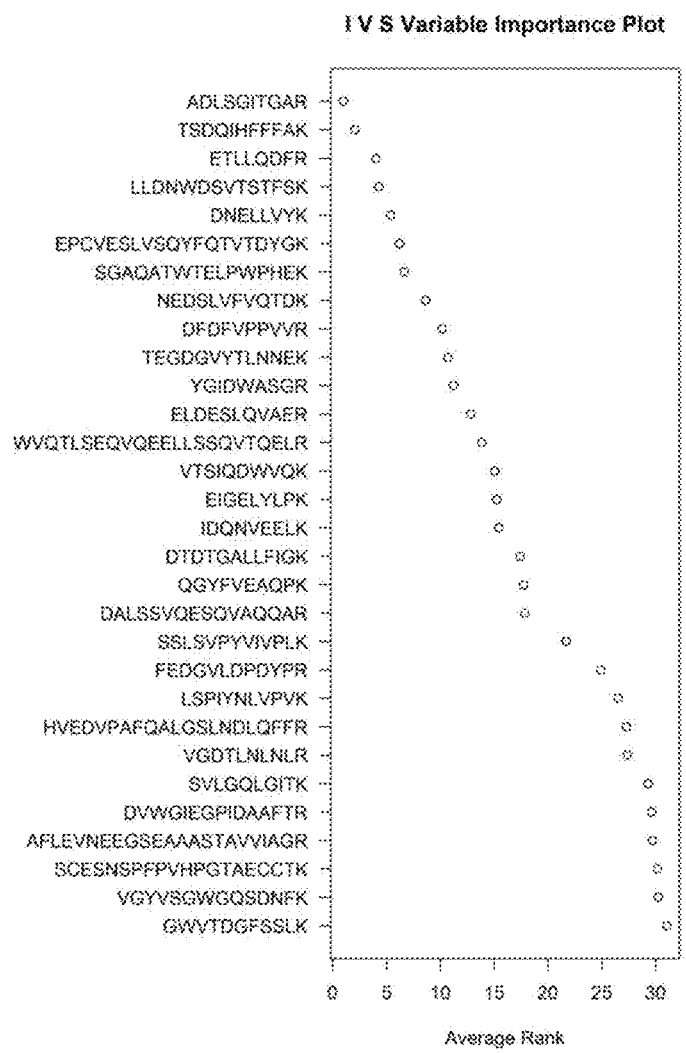

Again in order to identify which peptides were most important in obtaining the AUC the average variable importance measure for each peptide was taken over the 100 iterations of the random forest model (see in FIG. 19).

Significant Versus Aggressive

Figure 20:
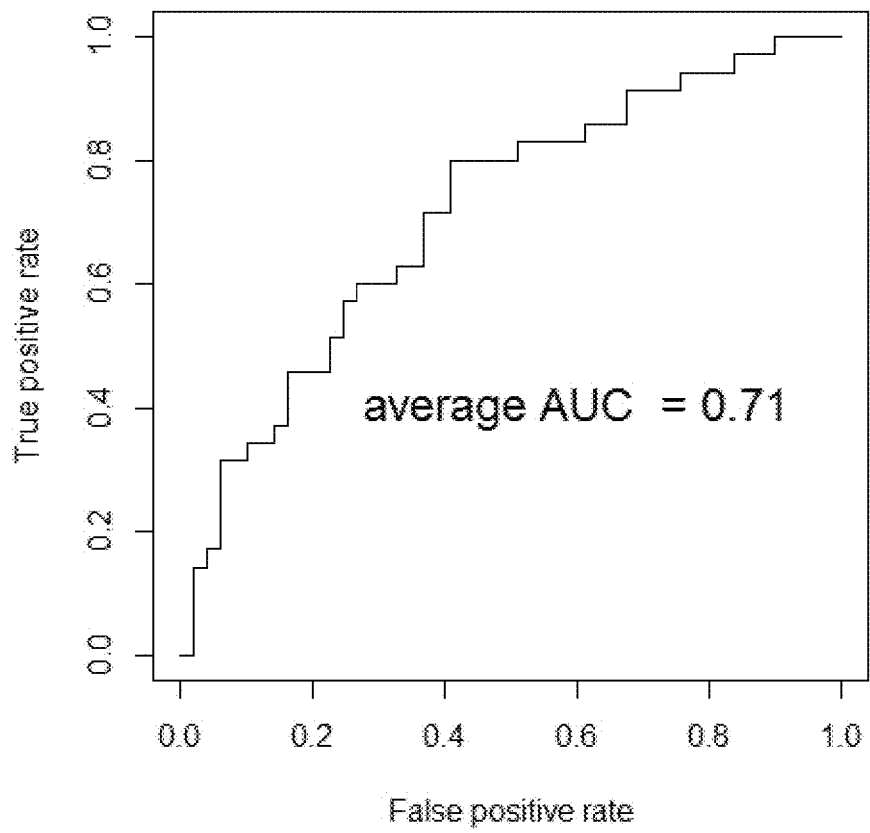
FIG. 20. Average AUC over 100 iterations of random forest for Significant Versus Aggressive patients FIG. 21. Average ranked variable importance of the top 30 peptides for significant versus aggressive disease. SEQ ID NOs. for each of the peptides listed from top to bottom are: 10, 9, 26, 39, 11, 16, 40, 4, 13, 17, 44, 18, 21, 3, 5, 36, 48, 15, 8, 49, 35, 19, 12, 27, 42, 28, 29, 31, 1 and 50 respectively.

When this analysis was performed on the "significant" versus "aggressive" patients it was found to give an average AUC of 0.71. The ROC curve for significant versus aggressive disease can be seen in FIG. 20.

Figure 21:
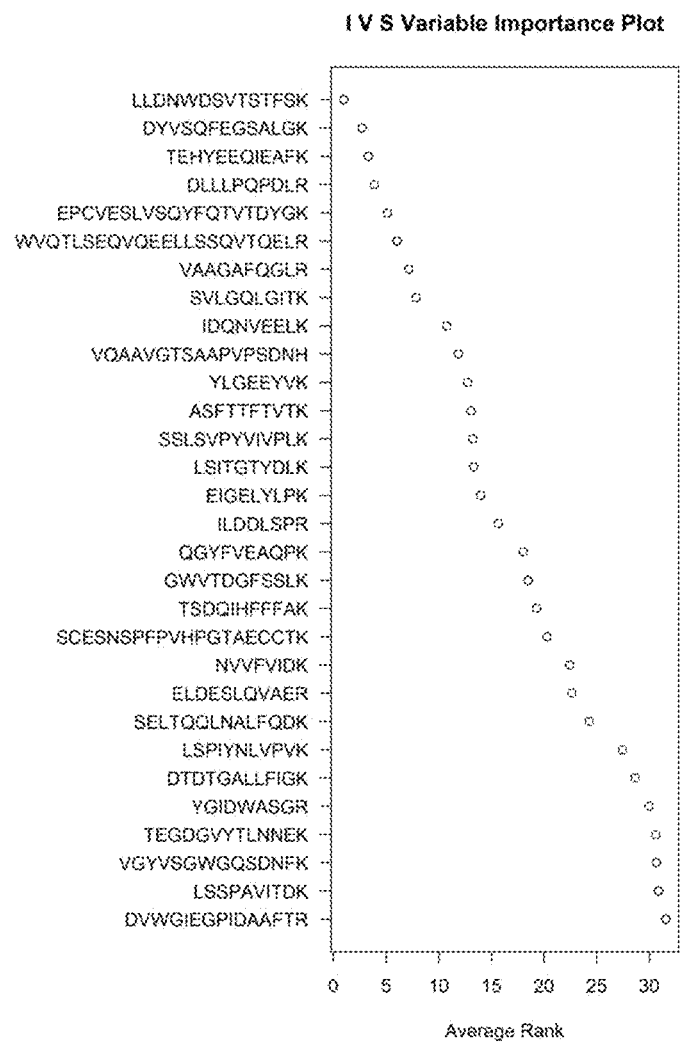
Figure 22A:
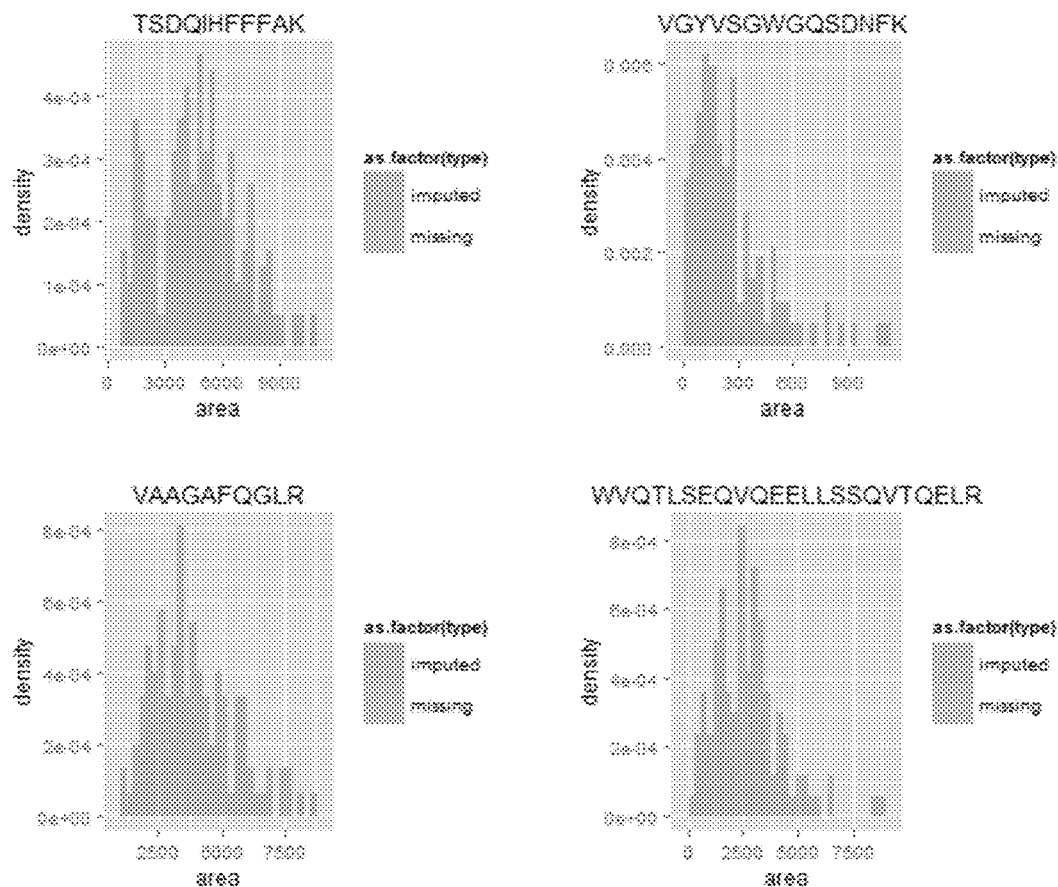
FIG. 22A-D. Histograms comparing the distribution of the imputed data versus the data with missing values for peptides. Parts A-D correspond to the following peptides: A: SEQ ID NOs. 8, 31, 40 and 16; B: SEQ ID NOs. 1, 25, 35 and 21; C: SEQ ID NOs. 11, 3, 52 and 27 (as shown in parts A-C) in the order top left, top right, bottom left, bottom right; D: SEQ ID NOs. 105, 47, 18, 50 and 28 (in the order top left, top right, middle left, middle right, bottom left).
Figure 22B:
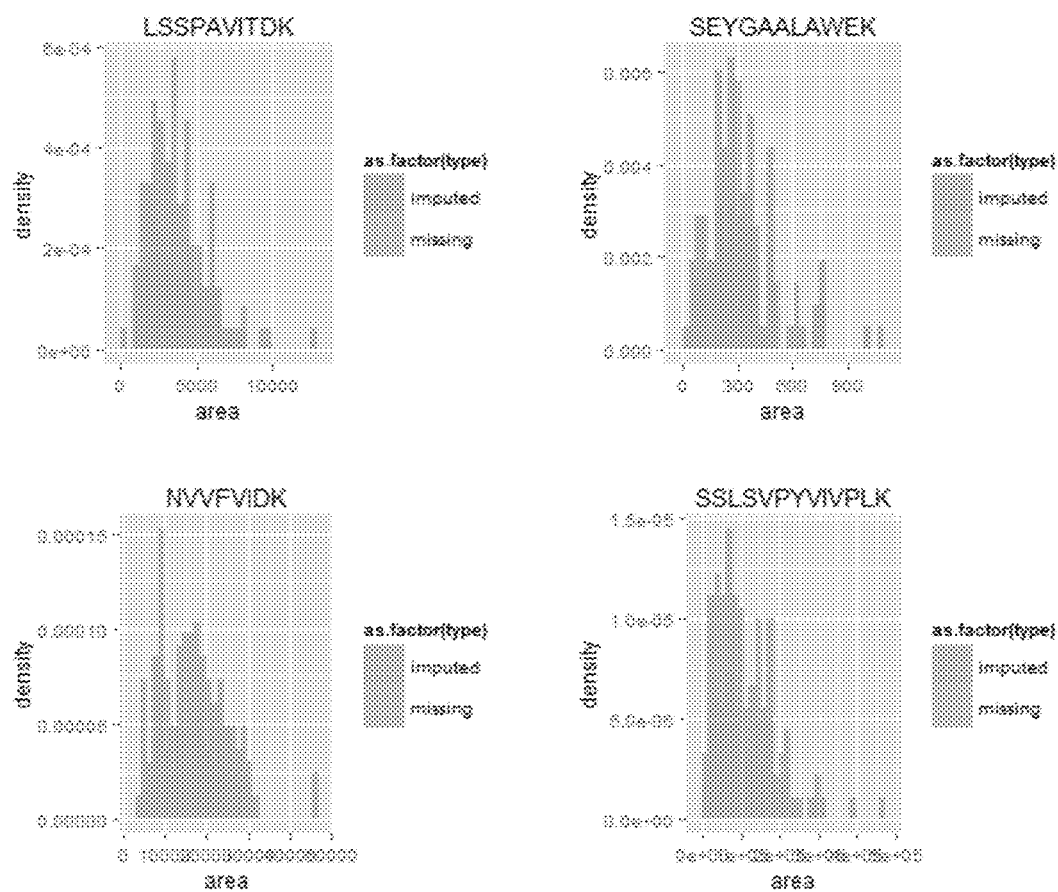
Figure 22C:
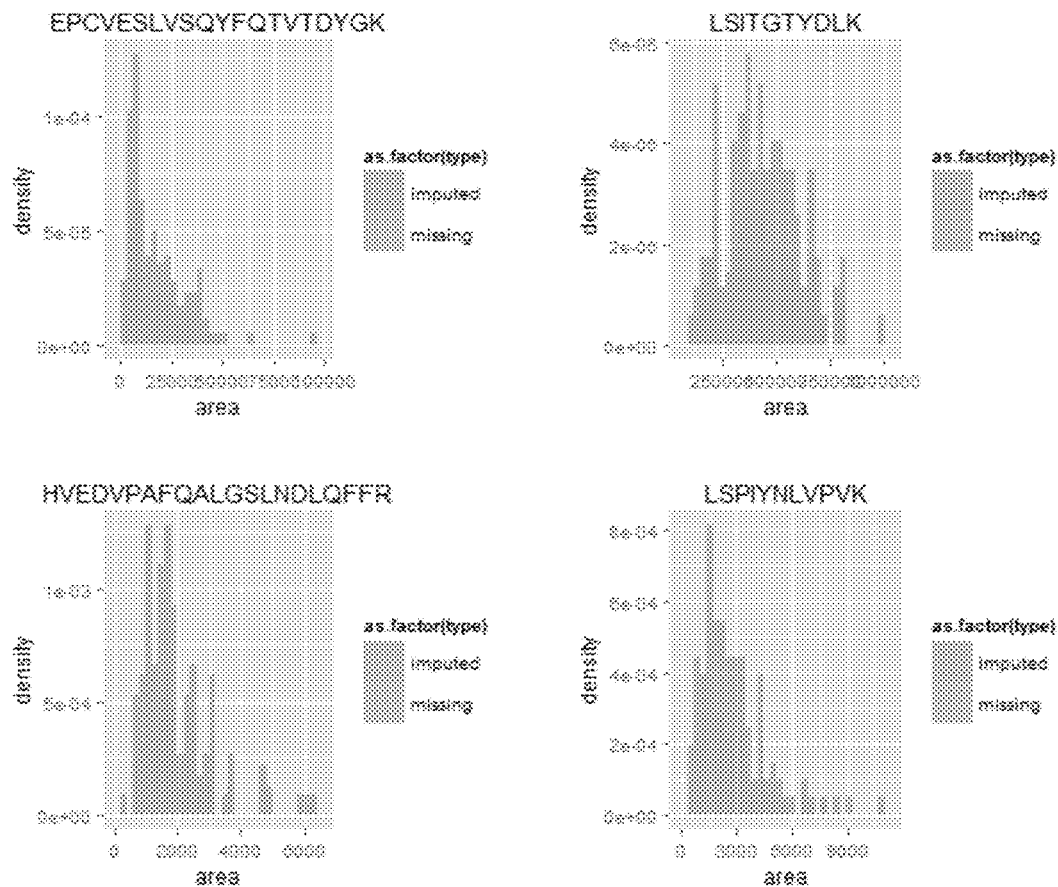
Figure 22D:
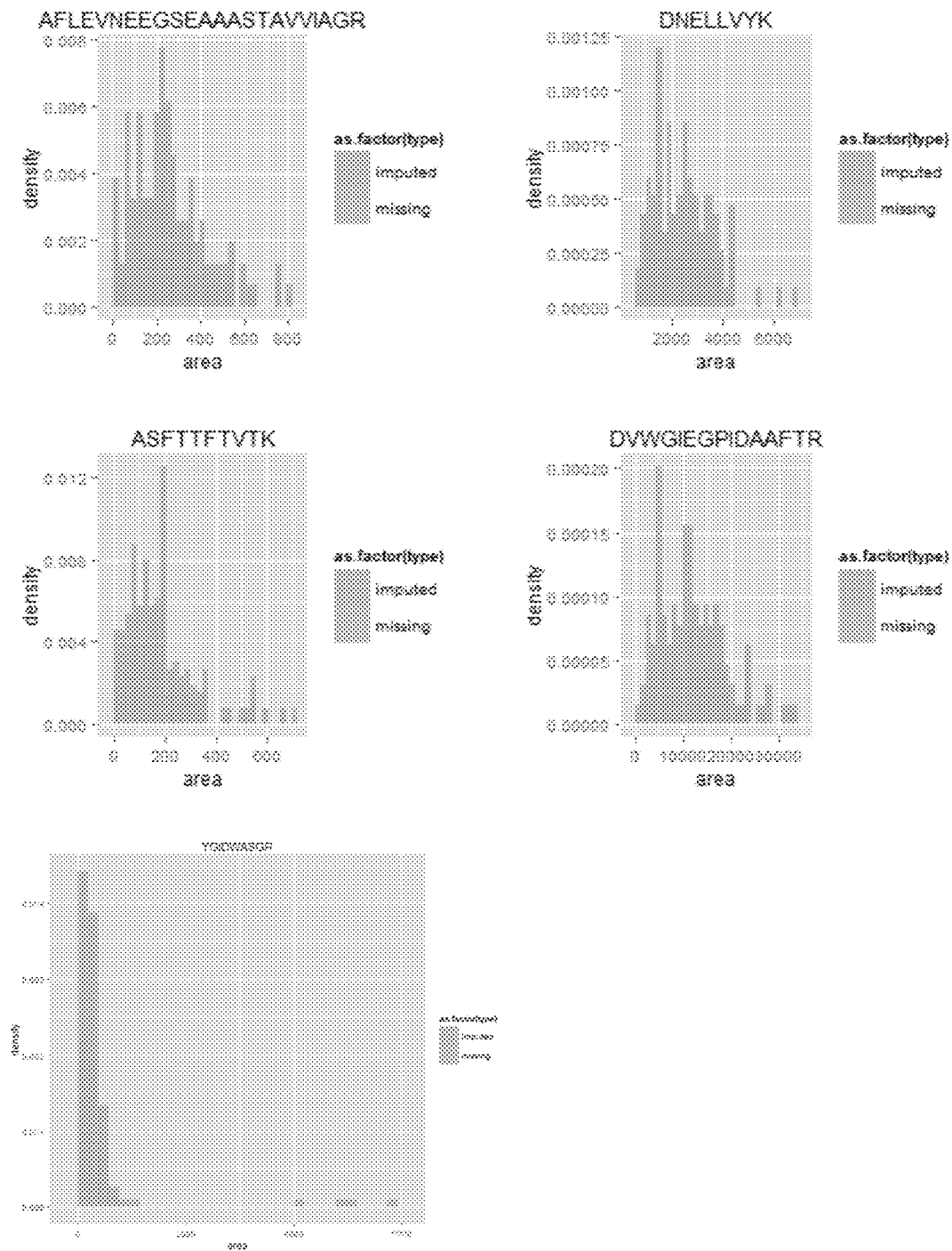

The most important variables identified by the random forest model can be seen in FIG. 21.

SUMMARY/CONCLUSIONS

It appears that this biomarker panel performs reasonably well at predicting indolent and significant (OC) from aggressive (NOC) patients with an AUC of in the region of 0.72-0.73.

Future work includes scaling the variables and using the information in the refpool samples to calibrate the data and correct for technical variability inherent in the experiment. Also of interest would be to perform the above analysis on multiply imputed datasets in order to establish how much the variability due to the uncertainty surrounding the missing values affects the overall results.

APPENDIX 1

| FileName | Type | Sample Number | Batch |
|---|---|---|---|
| 131118_Batch1_Sample_REFPOOL1.d | | 1 | 1 |
| 131118_Batch1_Sample_REFPOOL2.d | | 2 | 1 |
| 131118_Batch1_Sample_1.d | I | 3 | 1 |
| 131118_Batch1_Sample_35.d | S | 4 | 1 |
| 131118_Batch1_Sample_70.d | A | 5 | 1 |
| 131118_Batch1_Sample_2.d | I | 6 | 1 |
| 131118_Batch1_Sample_36.d | S | 7 | 1 |
| 131118_Batch1_Sample_71b.d | A | 8 | 1 |
| 131118_Batch1_Sample_3.d | I | 9 | 1 |
| 131118_Batch1_Sample_37.d | S | 10 | 1 |
| 131118_Batch1_Sample_72.d | A | 11 | 1 |
| 131118_Batch1_Sample_4.d | I | 12 | 1 |
| 131118_Batch1_Sample_38.d | S | 13 | 1 |
| 131118_Batch1_Sample_REFPOOL3.d | | 14 | 1 |
| 131118_Batch1_Sample_73.d | A | 15 | 1 |
| 131118_Batch1_Sample_5.d | I | 16 | 1 |
| 131118_Batch1_Sample_39.d | S | 17 | 1 |
| 131118_Batch1_Sample_74.d | A | 18 | 1 |
| 131118_Batch1_Sample_6.d | I | 19 | 1 |
| 131118_Batch1_Sample_40.d | S | 20 | 1 |
| 131118_Batch1_Sample_75.d | A | 22 | 1 |
| 131118_Batch1_Sample_7.d | I | 23 | 1 |
| 131118_Batch1_Sample_41.d | S | 24 | 1 |
| 131118_Batch1_Sample_76.d | A | 25 | 1 |
| 131118_Batch1_Sample_8.d | I | 26 | 1 |
| 131118_Batch1_Sample_42.d | S | 27 | 1 |
| 131118_Batch1_Sample_77.d | A | 28 | 1 |
| 131120_Batch2_Sample_REFPOOL1.d | | 1 | 2 |
| 131120_Batch2_Sample_REFPOOL2.d | | 2 | 2 |
| 131120_Batch2_Sample_9.d | I | 3 | 2 |
| 131120_Batch2_Sample_43.d | S | 4 | 2 |
| 131120_Batch2_Sample_78.d | A | 5 | 2 |
| 131120_Batch2_Sample_10.d | I | 6 | 2 |
| 131120_Batch2_Sample_44.d | S | 7 | 2 |
| 131120_Batch2_Sample_79.d | A | 8 | 2 |
| 131120_Batch2_Sample_11.d | I | 9 | 2 |
| 131120_Batch2_Sample_80.d | A | 11 | 2 |
| 131120_Batch2_Sample_12.d | I | 12 | 2 |
| 131120_Batch2_Sample_45.d | S | 12 | 2 |
| 131120_Batch2_Sample_46.d | S | 13 | 2 |
| 131120_Batch2_Sample_REFPOOL3.d | | 14 | 2 |
| 131120_Batch2_Sample_81.d | A | 15 | 2 |
| 131120_Batch2_Sample_13.d | I | 16 | 2 |
| 131120_Batch2_Sample_47.d | S | 17 | 2 |
| 131120_Batch2_Sample_82.d | A | 18 | 2 |
| 131120_Batch2_Sample_14.d | I | 19 | 2 |
| 131120_Batch2_Sample_48.d | S | 20 | 2 |
| 131120_Batch2_Sample_REFPOOL4.d | | 21 | 2 |
| 131120_Batch2_Sample_83.d | A | 22 | 2 |
| 131120_Batch2_Sample_15.d | I | 23 | 2 |
| 131120_Batch2_Sample_49.d | S | 24 | 2 |
| 131120_Batch2_Sample_84.d | A | 25 | 2 |
| 131120_Batch2_Sample_85.d | A | 26 | 2 |
| 131120_Batch2_Sample_86.d | A | 27 | 2 |
| 131120_Batch2_Sample_16.d | I | 28 | 2 |
| 131120_Batch2_Sample_REFPOOL5.d | | 29 | 2 |
| 131120_Batch2_Sample_80X_control.d | A | 30 | 2 |
| 131122_Batch3_Sample_REFPOOL1.d | | 1 | 3 |
| 131122_Batch3_Sample_REFPOOL2.d | | 2 | 3 |
| 131122_Batch3_Sample_50.d | S | 3 | 3 |
| 131122_Batch3_Sample_87.d | A | 4 | 3 |

APPENDIX 1-continued

| | | | |
|---|---|---|---|
| 131122__Batch3__Sample__88.d | A | 5 | 3 |
| 131122__Batch3__Sample__89.d | A | 6 | 3 |
| 131122__Batch3__Sample__17.d | I | 7 | 3 |
| 131122__Batch3__Sample__51.d | S | 8 | 3 |
| 131122__Batch3__Sample__90.d | A | 9 | 3 |
| 131122__Batch3__Sample__91.d | A | 10 | 3 |
| 131122__Batch3__Sample__92.d | A | 11 | 3 |
| 131122__Batch3__Sample__18.d | I | 12 | 3 |
| 131122__Batch3__Sample__52.d | S | 13 | 3 |
| 131122__Batch3__Sample__REFPOOL3.d | | 14 | 3 |
| 131122__Batch3__Sample__93.d | A | 15 | 3 |
| 131122__Batch3__Sample__94.d | A | 16 | 3 |
| 131122__Batch3__Sample__95.d | A | 17 | 3 |
| 131122__Batch3__Sample__19.d | I | 18 | 3 |
| 131122__Batch3__Sample__53.d | S | 19 | 3 |
| 131122__Batch3__Sample__96.d | A | 20 | 3 |
| 131122__Batch3__Sample__REFPOOL4.d | | 21 | 3 |
| 131122__Batch3__Sample__20.d | I | 22 | 3 |
| 131122__Batch3__Sample__54.d | S | 23 | 3 |
| 131122__Batch3__Sample__97.d | A | 24 | 3 |
| 131122__Batch3__Sample__21.d | I | 25 | 3 |
| 131125__Batch4__Sample__REFPOOL1.d | | 1 | 4 |
| 131125__Batch4__Sample__REFPOOL2.d | | 2 | 4 |
| 131125__Batch4__Sample__100.d | A | 3 | 4 |
| 131125__Batch4__Sample__22.d | I | 4 | 4 |
| 131125__Batch4__Sample__56.d | S | 5 | 4 |
| 131125__Batch4__Sample__101.d | A | 6 | 4 |
| 131125__Batch4__Sample__102.d | A | 7 | 4 |
| 131125__Batch4__Sample__23.d | I | 8 | 4 |
| 131125__Batch4__Sample__57.d | S | 9 | 4 |
| 131125__Batch4__Sample__103.d | A | 10 | 4 |
| 131125__Batch4__Sample__104.d | A | 11 | 4 |
| 131125__Batch4__Sample__24.d | I | 12 | 4 |
| 131125__Batch4__Sample__25.d | I | 13 | 4 |
| 131125__Batch4__Sample__REFPOOL3.d | | 14 | 4 |
| 131125__Batch4__Sample__26.d | I | 15 | 4 |
| 131125__Batch4__Sample__58.d | S | 16 | 4 |
| 131125__Batch4__Sample__59.d | S | 17 | 4 |
| 131125__Batch4__Sample__60.d | S | 18 | 4 |
| 131125__Batch4__Sample__105.d | A | 19 | 4 |
| 131125__Batch4__Sample__106.d | A | 20 | 4 |
| 131125__Batch4__Sample__REFPOOL4.d | | 21 | 4 |
| 131125__Batch4__Sample__27.d | I | 22 | 4 |
| 131125__Batch4__Sample__28.d | I | 23 | 4 |
| 131125__Batch4__Sample__61.d | S | 24 | 4 |
| 131125__Batch4__Sample__62.d | S | 25 | 4 |
| 131125__Batch4__Sample__107.d | A | 26 | 4 |
| 131125__Batch4__Sample__108.d | A | 27 | 4 |
| 131125__Batch4__Sample__29.d | I | 28 | 4 |
| 131125__Batch4__Sample__REFPOOL5.d | | 29 | 4 |
| 131127__Batch5__Sample__REFPOOL1.d | | 1 | 5 |
| 131127__Batch5__Sample__REFPOOL2.d | | 2 | 5 |
| 131127__Batch5__Sample__30.d | I | 3 | 5 |
| 131127__Batch5__Sample__63.d | S | 4 | 5 |
| 131127__Batch5__Sample__64.d | S | 5 | 5 |
| 131127__Batch5__Sample__109.d | A | 6 | 5 |
| 131127__Batch5__Sample__110.d | A | 7 | 5 |
| 131127__Batch5__Sample__31.d | I | 8 | 5 |
| 131127__Batch5__Sample__65.d | S | 9 | 5 |
| 131127__Batch5__Sample__111.d | A | 10 | 5 |
| 131127__Batch5__Sample__112.d | A | 11 | 5 |
| 131127__Batch5__Sample__32.d | I | 12 | 5 |
| 131127__Batch5__Sample__66.d | S | 13 | 5 |
| 131127__Batch5__Sample__REFPOOL3.d | | 14 | 5 |
| 131127__Batch5__Sample__113.d | A | 15 | 5 |
| 131127__Batch5__Sample__33.d | I | 16 | 5 |
| 131127__Batch5__Sample__67.d | S | 17 | 5 |
| 131127__Batch5__Sample__68.d | S | 18 | 5 |
| 131127__Batch5__Sample__114.d | A | 19 | 5 |
| 131127__Batch5__Sample__115.d | A | 20 | 5 |
| 131127__Batch5__Sample__REFPOOL4.d | | 21 | 5 |
| 131127__Batch5__Sample__34.d | I | 22 | 5 |
| 131127__Batch5__Sample__69.d | S | 23 | 5 |
| 131127__Batch5__Sample__116.d | A | 24 | 5 |
| 131127__Batch5__Sample__rerun55.d | S | 25 | 5 |
| 131127__Batch5__Sample__rerun98.d | A | 26 | 5 |
| 131127__Batch5__Sample__99.d | A | 27 | 5 |
| 131127__Batch5__Sample__100.d | A | 28 | 5 |
| 131127__Batch5__Sample__REFPOOL5.d | | 29 | 5 |

APPENDIX 1-continued

SOP Title: In solution tryptic digestion.

SOP number: 4.0  
Date: 23 Sep. 2010  
Written by: Brian Morrissey

Procedure description.

Tryptic digestion for proteins in solution, suitable for MARS depletions.

| | |
|---|---|
| Materials | Pipettes, pipette tips. |
| | Agilent 5 KDa MW spin concentrators. Order No: 5185-5991. |
| Reagents | Ammonium bicarbonate, DTT, Ioadeacetamide, Trifloroethanol, Formic acid, Acetonitrile. |
| | Trypsin - sequencing grade modified porcine (Promega) The substrate is dissolved in 50 mM Tris-HCl, 1 mM CaCl2 (pH 7.6). Order No: V5111 |

Procedure.

All solutions should be made in HPLC grade water or solvents
Wear gloves at all times and try to avoid getting particulate/dust into the samples limiting the time tubes are uncapped.
Trypsin should be sequencing grade modified porcine (Promega) The substrate is dissolved in 50 mM Tris-HCl, 1 mM CaCl2 (pH 7.6).

Solution preparation.

(A) 1M NH4CO3 stock solution MW = 79.06
    79.06 g in 1000 ml = 1 mol.
    0.7906 g in 10 ml ddH2O = 1 mol.

(B) 50 mM $NH_4CO_3$ working solution
    1/20 dilution of stock (A).

(C) 200 mM DTT working solution MW = 154.2
    154.2 g in 1000 ml = 1 mol.
    0.03084 g in 1 ml (B) = 200 mM (D) 200 mM IAA working solution MW = 185
    185 g in 1000 ml = 1 mol.
    0.037 g in 1 ml (B) = 200 mM (E) 50 mM $NH_4Co_3$ - 5% TFE
    50 µl (A)
    50 µl TFE
    900 µl $H_2O$
    (increase volumes as appropriate)

(G) 0.1% (v/v) formic acid, 3% (v/v) acetonitrile.
    1 µl formic acid.
    30 µl acteonitrile.
    969 µl $ddH_2O$.

1. Adjust the sample to the desired protein concentration in final buffer conditions of 50 mM $NH_4HCO_3$, 10 mM DTT (disulphide reduction), and 50% trifluoroethanol [TFE - denaturating agent). Vortex and incubate @room temp for 30 min. - In 4 ml 5 KDa MW. Agilent spin filters.

2. Add IAA (iodoacetamide) to give a final concentration of 20 mM (alkyate thiols). Vortex briefly (incubate, 30 min, RT, dark). Add DTT to a final concentration of 10 mM to quench excess IAA. If IAA is not destroyed it will slowly alkylate lysine residues.

3. Add 3 ml 5% (v/v) TFE, 50 mM $NH_4HCO_3$ and spin for 1 hr at 3100 g, repeat removing excess filtrate from the collector tube.

4. Recover the sample from the spin filter. The volume should be as small as possible, take out the remaining solution in the filter and wash the filter 2-3 times (50 ul) with 5% TFE in 50 mM NH4HCO3. Note the final concentration of TFE should be less than 5% as it can destroy or decrease the activity of trypsin.

5. Re-suspend an appropriate amount of trypsin in 5% (v/v) TFE, 50 mM $NH_4HCO_3$ at a concentration of 0.2 µg trypsin/µl-20 µg trypsin in 100 µl (F) (N.B. trypsin should be re-suspended immediately prior to addition to the sample to prevent degradation of trypsin by autolysis - allow 5 minutes for complete re-suspension of trypsin).
    [check for pH ~8]

6. Add trypsin to the samples at the ration of 1:100/trypsin:sample protein (for 100 µg of sample protein add 1 µg of trypsin) Add $CaCl_2$ to a final concentration of 1 mM. and incubate @ 37° C. for 18-24 hrs at 500 rpm in a thermomixer.

7. SpeedVac the sample to dryness and re-suspend in (OFFGEL buffer for fractionation) 0.1% (v/v) formic acid, 3% (v/v) acetonitrile. Mix the sample on a thermomixer for 10 minutes to ensure complete re-suspension of tryptic peptides (10 minutes, 1000 RPM). 0.5-1.0 µgl/µl is an appropriate concentration for analysis.

8. Centrifuge the sample (10 min, 20,000 x g, 4° C.) and pipette into a HPLC injection vial for analysis.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

Various publications are cited herein, the disclosures of which are incorporated by reference in their entireties.

The invention claimed is:

1. A method comprising detecting levels of peptides in a biological sample from a subject, the peptides comprising:
   (i) a peptide of Pigment epithelium-derived factor having an amino acid sequence TVQAVLTVPK (SEQ ID NO:41); and
   (ii) a peptide of Antithrombin-III having an amino acid sequence TSDQIHFFFAK (SEQ ID NO:8),
   wherein the method further comprises:
   (i) comparing the level of the peptide of Pigment epithelium-derived factor to the level of the peptide of Pigment epithelium-derived factor in one or more control samples; and
   (ii) comparing the level of the peptide of Antithrombin-III to the level of the peptide of Antithrombin-III in one or more control samples,
   wherein the one or more control samples are from:
   (i) one or more subjects with extra-capsular extension of prostate cancer;
   (ii) one or more subjects with Gleason score 6 prostate cancer and/or Gleason score 7 prostate cancer; or
   (iii) one or more subjects with Gleason score 3+4 prostate cancer and/or Gleason score 4+3 prostate cancer.

2. The method claim 1, wherein the level of the peptide of Pigment epithelium-derived factor in the sample from the subject and the level of the peptide of Pigment epithelium-derived factor from the one or more characterized control samples are analysed using a statistical model comprising performing partial least square discriminant analysis; and the level of the peptide of Antithrombin-III in the sample from the subject and the level of the peptide of Antithrombin-III from the one or more characterized control samples are analysed using a statistical model comprising performing partial least square discriminant analysis.

3. The method of claim 1, which method is performed in vitro.

4. The method of claim 1, wherein the sample comprises, consists essentially of or consists of a biological fluid or a fluid or lysate generated from a biological material.

5. The method of claim 4, wherein the biological fluid comprises, consists essentially of or consists of a blood sample, optionally wherein the blood sample is a serum sample.

6. The method of claim 4, wherein the biological fluid comprises, consists essentially of or consists of seminal fluid.

7. The method of claim 4, wherein the biological fluid comprises, consists essentially of or consists of urine, optionally wherein the urine is obtained before or after a prostatic massage.

8. The method of claim 4, wherein the biological material comprises, consists essentially of or consists of prostate tissue.

9. The method of claim 1, wherein the level of the peptide of Pigment epithelium-derived factor and the level of the peptide of Antithrombin-III are measured by mass spectrometry, immunoassay and/or radioassay.

10. The method of claim 1, wherein the level of the peptide of Pigment epithelium-derived factor and the level of the peptide of Antithrombin-III are measured by mass spectrometry comprising, consisting essentially of or consisting of multiple reaction monitoring (MRM).

11. A method comprising detecting levels in a biological sample of Pigment epithelium-derived factor, Antithrombin-III, Zinc alpha-2 glycoprotein, and Plasminogen, or at least one peptide thereof respectively, wherein the levels are measured by performing mass spectrometry comprising multiple reaction monitoring (MRM), wherein the biological sample comprises, consists essentially of or consists of:
   (a) a blood sample, optionally wherein the blood sample is a serum sample;
   (b) seminal fluid;

(c) urine obtained after a prostatic massage; or
(d) prostate tissue.

12. A method comprising:
(a) detecting levels of Pigment epithelium-derived factor and Antithrombin-III, or at least one peptide thereof respectively, in a biological sample from a subject; and
(b) after detecting levels of Pigment epithelium-derived factor and Antithrombin-III, or at least one peptide thereof respectively, in the biological sample from the subject, treating the subject with a therapy selected from hormone therapy that reduces the level and/or activity of testosterone in the subject, radiation, and radical prostatectomy.

13. A method comprising detecting levels in a biological sample of Pigment epithelium-derived factor, Antithrombin-III, and Zinc alpha-2 glycoprotein, or at least one peptide thereof respectively, wherein the levels are measured by performing mass spectrometry comprising multiple reaction monitoring (MRM), wherein the biological sample comprises, consists essentially of, or consists of:
(a) a blood sample, optionally wherein the blood sample is a serum sample;
(b) seminal fluid;
(c) urine obtained after a prostatic massage; or
(d) prostate tissue;

wherein the method further comprises: comparing the level of Pigment epithelium-derived factor, or at least one peptide thereof, to the level of Pigment epithelium-derived factor, or at least one peptide thereof, in one or more control samples; and comparing the level of Antithrombin-III, or at least one peptide thereof, to the level of Antithrombin-III, or at least one peptide thereof, in one or more control samples; and comparing the level of Zinc alpha-2 glycoprotein, or at least one peptide thereof, to the level of Zinc alpha-2 glycoprotein, or at least one peptide thereof, in one of more control samples; wherein the one or more control samples are from:
(a) one or more subjects with extra-capsular extension of prostate cancer;
(b) one or more subjects with Gleason score 6 prostate cancer and/or Gleason score 7 prostate cancer; or
(c) one or more subjects with Gleason score 3+4 prostate cancer and/or Gleason score 4+3 prostate cancer.

* * * * *

SEQUENCE LISTING

```
<160> NUMBER OF SEQ ID NOS: 104

<210> SEQ ID NO 1
<211> LENGTH: 10
<212> TYPE: PRT
<213> ORGANISM: Homo sapiens

<400> SEQUENCE: 1

Leu Ser Ser Pro Ala Val Ile Thr Asp Lys
1               5                   10

<210> SEQ ID NO 2
<211> LENGTH: 10
<212> TYPE: PRT
<213> ORGANISM: Homo sapiens

<400> SEQUENCE: 2

Glu Ala Gln Leu Pro Val Ile Glu Asn Lys
1               5                   10

<210> SEQ ID NO 3
<211> LENGTH: 10
<212> TYPE: PRT
<213> ORGANISM: Homo sapiens

<400> SEQUENCE: 3

Leu Ser Ile Thr Gly Thr Tyr Asp Leu Lys
1               5                   10

<210> SEQ ID NO 4
<211> LENGTH: 10
<212> TYPE: PRT
<213> ORGANISM: Homo sapiens

<400> SEQUENCE: 4

Ser Val Leu Gly Gln Leu Gly Ile Thr Lys
1               5                   10

<210> SEQ ID NO 5
<211> LENGTH: 9
<212> TYPE: PRT
<213> ORGANISM: Homo sapiens

<400> SEQUENCE: 5

Glu Ile Gly Glu Leu Tyr Leu Pro Lys
1               5

<210> SEQ ID NO 6
<211> LENGTH: 10
<212> TYPE: PRT
<213> ORGANISM: Homo sapiens

<400> SEQUENCE: 6

Ala Asp Leu Ser Gly Ile Thr Gly Ala Arg
1               5                   10

<210> SEQ ID NO 7
<211> LENGTH: 12
```

```
<212> TYPE: PRT
<213> ORGANISM: Homo sapiens

<400> SEQUENCE: 7

Asn Glu Asp Ser Leu Val Phe Val Gln Thr Asp Lys
1               5                   10

<210> SEQ ID NO 8
<211> LENGTH: 11
<212> TYPE: PRT
<213> ORGANISM: Homo sapiens

<400> SEQUENCE: 8

Thr Ser Asp Gln Ile His Phe Phe Phe Ala Lys
1               5                   10

<210> SEQ ID NO 9
<211> LENGTH: 13
<212> TYPE: PRT
<213> ORGANISM: Homo sapiens

<400> SEQUENCE: 9

Asp Tyr Val Ser Gln Phe Glu Gly Ser Ala Leu Gly Lys
1               5                   10

<210> SEQ ID NO 10
<211> LENGTH: 14
<212> TYPE: PRT
<213> ORGANISM: Homo sapiens

<400> SEQUENCE: 10

Leu Leu Asp Asn Trp Asp Ser Val Thr Ser Thr Phe Ser Lys
1               5                   10

<210> SEQ ID NO 11
<211> LENGTH: 20
<212> TYPE: PRT
<213> ORGANISM: Homo sapiens

<400> SEQUENCE: 11

Glu Pro Cys Val Glu Ser Leu Val Ser Gln Tyr Phe Gln Thr Val Thr
1               5                   10                  15

Asp Tyr Gly Lys
            20

<210> SEQ ID NO 12
<211> LENGTH: 14
<212> TYPE: PRT
<213> ORGANISM: Homo sapiens

<400> SEQUENCE: 12

Ser Glu Leu Thr Gln Gln Leu Asn Ala Leu Phe Gln Asp Lys
1               5                   10

<210> SEQ ID NO 13
<211> LENGTH: 9
<212> TYPE: PRT
<213> ORGANISM: Homo sapiens

<400> SEQUENCE: 13

Ile Asp Gln Asn Val Glu Glu Leu Lys
1               5

<210> SEQ ID NO 14
```

```
<211> LENGTH: 16
<212> TYPE: PRT
<213> ORGANISM: Homo sapiens

<400> SEQUENCE: 14

Asp Ala Leu Ser Ser Val Gln Glu Ser Gln Val Ala Gln Gln Ala Arg
1               5                   10                  15

<210> SEQ ID NO 15
<211> LENGTH: 11
<212> TYPE: PRT
<213> ORGANISM: Homo sapiens

<400> SEQUENCE: 15

Gly Trp Val Thr Asp Gly Phe Ser Ser Leu Lys
1               5                   10

<210> SEQ ID NO 16
<211> LENGTH: 23
<212> TYPE: PRT
<213> ORGANISM: Homo sapiens

<400> SEQUENCE: 16

Trp Val Gln Thr Leu Ser Glu Gln Val Gln Glu Leu Leu Ser Ser
1               5                   10                  15

Gln Val Thr Gln Glu Leu Arg
            20

<210> SEQ ID NO 17
<211> LENGTH: 17
<212> TYPE: PRT
<213> ORGANISM: Homo sapiens

<400> SEQUENCE: 17

Val Gln Ala Ala Val Gly Thr Ser Ala Ala Pro Val Pro Ser Asp Asn
1               5                   10                  15

His

<210> SEQ ID NO 18
<211> LENGTH: 10
<212> TYPE: PRT
<213> ORGANISM: Homo sapiens

<400> SEQUENCE: 18

Ala Ser Phe Thr Thr Phe Thr Val Thr Lys
1               5                   10

<210> SEQ ID NO 19
<211> LENGTH: 11
<212> TYPE: PRT
<213> ORGANISM: Homo sapiens

<400> SEQUENCE: 19

Glu Leu Asp Glu Ser Leu Gln Val Ala Glu Arg
1               5                   10

<210> SEQ ID NO 20
<211> LENGTH: 23
<212> TYPE: PRT
<213> ORGANISM: Homo sapiens

<400> SEQUENCE: 20

Val Thr Thr Val Ala Ser His Thr Ser Asp Ser Asp Val Pro Ser Gly
1               5                   10                  15
```

Val Thr Glu Val Val Val Lys
            20

<210> SEQ ID NO 21
<211> LENGTH: 13
<212> TYPE: PRT
<213> ORGANISM: Homo sapiens

<400> SEQUENCE: 21

Ser Ser Leu Ser Val Pro Tyr Val Ile Val Pro Leu Lys
1               5                   10

<210> SEQ ID NO 22
<211> LENGTH: 10
<212> TYPE: PRT
<213> ORGANISM: Homo sapiens

<400> SEQUENCE: 22

Asp Phe Asp Phe Val Pro Pro Val Val Arg
1               5                   10

<210> SEQ ID NO 23
<211> LENGTH: 10
<212> TYPE: PRT
<213> ORGANISM: Homo sapiens

<400> SEQUENCE: 23

Val Gly Asp Thr Leu Asn Leu Asn Leu Arg
1               5                   10

<210> SEQ ID NO 24
<211> LENGTH: 13
<212> TYPE: PRT
<213> ORGANISM: Homo sapiens

<400> SEQUENCE: 24

Gly Leu Glu Glu Glu Leu Gln Phe Ser Leu Gly Ser Lys
1               5                   10

<210> SEQ ID NO 25
<211> LENGTH: 11
<212> TYPE: PRT
<213> ORGANISM: Homo sapiens

<400> SEQUENCE: 25

Ser Glu Tyr Gly Ala Ala Leu Ala Trp Glu Lys
1               5                   10

<210> SEQ ID NO 26
<211> LENGTH: 12
<212> TYPE: PRT
<213> ORGANISM: Homo sapiens

<400> SEQUENCE: 26

Thr Glu His Tyr Glu Glu Gln Ile Glu Ala Phe Lys
1               5                   10

<210> SEQ ID NO 27
<211> LENGTH: 11
<212> TYPE: PRT
<213> ORGANISM: Homo sapiens

<400> SEQUENCE: 27

Leu Ser Pro Ile Tyr Asn Leu Val Pro Val Lys

```
1               5                   10
```

<210> SEQ ID NO 28
<211> LENGTH: 9
<212> TYPE: PRT
<213> ORGANISM: Homo sapiens

<400> SEQUENCE: 28

```
Tyr Gly Ile Asp Trp Ala Ser Gly Arg
1               5
```

<210> SEQ ID NO 29
<211> LENGTH: 13
<212> TYPE: PRT
<213> ORGANISM: Homo sapiens

<400> SEQUENCE: 29

```
Thr Glu Gly Asp Gly Val Tyr Thr Leu Asn Asn Glu Lys
1               5                   10
```

<210> SEQ ID NO 30
<211> LENGTH: 10
<212> TYPE: PRT
<213> ORGANISM: Homo sapiens

<400> SEQUENCE: 30

```
Val Thr Ser Ile Gln Asp Trp Val Gln Lys
1               5                   10
```

<210> SEQ ID NO 31
<211> LENGTH: 14
<212> TYPE: PRT
<213> ORGANISM: Homo sapiens

<400> SEQUENCE: 31

```
Val Gly Tyr Val Ser Gly Trp Gly Gln Ser Asp Asn Phe Lys
1               5                   10
```

<210> SEQ ID NO 32
<211> LENGTH: 11
<212> TYPE: PRT
<213> ORGANISM: Homo sapiens

<400> SEQUENCE: 32

```
Asn Phe Pro Ser Pro Val Asp Ala Ala Phe Arg
1               5                   10
```

<210> SEQ ID NO 33
<211> LENGTH: 16
<212> TYPE: PRT
<213> ORGANISM: Homo sapiens

<400> SEQUENCE: 33

```
Ser Gly Ala Gln Ala Thr Trp Thr Glu Leu Pro Trp Pro His Glu Lys
1               5                   10                  15
```

<210> SEQ ID NO 34
<211> LENGTH: 8
<212> TYPE: PRT
<213> ORGANISM: Homo sapiens

<400> SEQUENCE: 34

```
Phe Leu Asn Val Leu Ser Pro Arg
1               5
```

<210> SEQ ID NO 35
<211> LENGTH: 8
<212> TYPE: PRT
<213> ORGANISM: Homo sapiens

<400> SEQUENCE: 35

Asn Val Val Phe Val Ile Asp Lys
1               5

<210> SEQ ID NO 36
<211> LENGTH: 8
<212> TYPE: PRT
<213> ORGANISM: Homo Sapiens

<400> SEQUENCE: 36

Ile Leu Asp Asp Leu Ser Pro Arg
1               5

<210> SEQ ID NO 37
<211> LENGTH: 11
<212> TYPE: PRT
<213> ORGANISM: Homo sapiens

<400> SEQUENCE: 37

Thr Val Gly Ser Asp Thr Phe Tyr Ser Phe Lys
1               5                   10

<210> SEQ ID NO 38
<211> LENGTH: 14
<212> TYPE: PRT
<213> ORGANISM: Homo sapiens

<400> SEQUENCE: 38

Ile Ala Ser Phe Ser Gln Asn Cys Asp Ile Tyr Pro Gly Lys
1               5                   10

<210> SEQ ID NO 39
<211> LENGTH: 10
<212> TYPE: PRT
<213> ORGANISM: Homo sapiens

<400> SEQUENCE: 39

Asp Leu Leu Leu Pro Gln Pro Asp Leu Arg
1               5                   10

<210> SEQ ID NO 40
<211> LENGTH: 10
<212> TYPE: PRT
<213> ORGANISM: Homo sapiens

<400> SEQUENCE: 40

Val Ala Ala Gly Ala Phe Gln Gly Leu Arg
1               5                   10

<210> SEQ ID NO 41
<211> LENGTH: 10
<212> TYPE: PRT
<213> ORGANISM: Homo sapiens

<400> SEQUENCE: 41

Thr Val Gln Ala Val Leu Thr Val Pro Lys
1               5                   10

<210> SEQ ID NO 42

```
<211> LENGTH: 12
<212> TYPE: PRT
<213> ORGANISM: Homo sapiens

<400> SEQUENCE: 42

Asp Thr Asp Thr Gly Ala Leu Leu Phe Ile Gly Lys
1               5                   10

<210> SEQ ID NO 43
<211> LENGTH: 8
<212> TYPE: PRT
<213> ORGANISM: Homo sapiens

<400> SEQUENCE: 43

Glu Thr Leu Leu Gln Asp Phe Arg
1               5

<210> SEQ ID NO 44
<211> LENGTH: 8
<212> TYPE: PRT
<213> ORGANISM: Homo sapiens

<400> SEQUENCE: 44

Tyr Leu Gly Glu Glu Tyr Val Lys
1               5

<210> SEQ ID NO 45
<211> LENGTH: 10
<212> TYPE: PRT
<213> ORGANISM: Homo sapiens

<400> SEQUENCE: 45

Leu Val Asn Glu Val Thr Glu Phe Ala Lys
1               5                   10

<210> SEQ ID NO 46
<211> LENGTH: 8
<212> TYPE: PRT
<213> ORGANISM: Homo sapiens

<400> SEQUENCE: 46

Phe Gln Asn Ala Leu Leu Val Arg
1               5

<210> SEQ ID NO 47
<211> LENGTH: 8
<212> TYPE: PRT
<213> ORGANISM: Homo sapiens

<400> SEQUENCE: 47

Asp Asn Glu Leu Leu Val Tyr Lys
1               5

<210> SEQ ID NO 48
<211> LENGTH: 10
<212> TYPE: PRT
<213> ORGANISM: Homo sapiens

<400> SEQUENCE: 48

Gln Gly Tyr Phe Val Glu Ala Gln Pro Lys
1               5                   10

<210> SEQ ID NO 49
<211> LENGTH: 20
<212> TYPE: PRT
```

```
<213> ORGANISM: Homo sapiens

<400> SEQUENCE: 49

Ser Cys Glu Ser Asn Ser Pro Phe Pro Val His Pro Gly Thr Ala Glu
1               5                   10                  15

Cys Cys Thr Lys
            20

<210> SEQ ID NO 50
<211> LENGTH: 15
<212> TYPE: PRT
<213> ORGANISM: Homo sapiens

<400> SEQUENCE: 50

Asp Val Trp Gly Ile Glu Gly Pro Ile Asp Ala Ala Phe Thr Arg
1               5                   10                  15

<210> SEQ ID NO 51
<211> LENGTH: 12
<212> TYPE: PRT
<213> ORGANISM: Homo sapiens

<400> SEQUENCE: 51

Phe Glu Asp Gly Val Leu Asp Pro Asp Tyr Pro Arg
1               5                   10

<210> SEQ ID NO 52
<211> LENGTH: 21
<212> TYPE: PRT
<213> ORGANISM: Homo sapiens

<400> SEQUENCE: 52

His Val Glu Asp Val Pro Ala Phe Gln Ala Leu Gly Ser Leu Asn Asp
1               5                   10                  15

Leu Gln Phe Phe Arg
            20

<210> SEQ ID NO 53
<211> LENGTH: 16
<212> TYPE: PRT
<213> ORGANISM: Homo sapiens

<400> SEQUENCE: 53

Gly Ala Gly Thr Asn Glu Asp Ala Leu Ile Glu Ile Leu Thr Thr Arg
1               5                   10                  15

<210> SEQ ID NO 54
<211> LENGTH: 13
<212> TYPE: PRT
<213> ORGANISM: Homo sapiens

<400> SEQUENCE: 54

Ser Asp Thr Ser Gly Asp Tyr Glu Ile Thr Leu Leu Lys
1               5                   10

<210> SEQ ID NO 55
<211> LENGTH: 16
<212> TYPE: PRT
<213> ORGANISM: Homo sapiens

<400> SEQUENCE: 55

Leu Leu Asp Leu Leu Val Pro Asp Ile Pro Glu Ser Val Glu Ile Lys
1               5                   10                  15
```

```
<210> SEQ ID NO 56
<211> LENGTH: 16
<212> TYPE: PRT
<213> ORGANISM: Homo sapiens

<400> SEQUENCE: 56

Gln Ala Leu Ala Glu Asn Glu Val Leu Phe Gly Thr Asn Gly Thr Lys
1               5                   10                  15

<210> SEQ ID NO 57
<211> LENGTH: 13
<212> TYPE: PRT
<213> ORGANISM: Homo sapiens

<400> SEQUENCE: 57

Asn Pro Asn Leu Pro Pro Glu Thr Val Asp Ser Leu Lys
1               5                   10

<210> SEQ ID NO 58
<211> LENGTH: 22
<212> TYPE: PRT
<213> ORGANISM: Homo sapiens

<400> SEQUENCE: 58

Ala Asp Gly Thr Val Asn Gln Ile Glu Gly Glu Ala Thr Pro Val Asn
1               5                   10                  15

Leu Thr Glu Pro Ala Lys
            20

<210> SEQ ID NO 59
<211> LENGTH: 15
<212> TYPE: PRT
<213> ORGANISM: Homo sapiens

<400> SEQUENCE: 59

Glu Trp Val Ala Ile Glu Ser Asp Ser Val Gln Pro Val Pro Arg
1               5                   10                  15

<210> SEQ ID NO 60
<211> LENGTH: 17
<212> TYPE: PRT
<213> ORGANISM: Homo sapiens

<400> SEQUENCE: 60

Gly Asp Gly Trp Leu Thr Asp Pro Tyr Val Leu Thr Glu Val Asp Gly
1               5                   10                  15

Lys

<210> SEQ ID NO 61
<211> LENGTH: 22
<212> TYPE: PRT
<213> ORGANISM: Homo sapiens

<400> SEQUENCE: 61

Glu Leu Gly Cys Gly Ala Ala Ser Gly Thr Pro Ser Gly Ile Leu Tyr
1               5                   10                  15

Glu Pro Pro Ala Glu Lys
            20

<210> SEQ ID NO 62
<211> LENGTH: 14
<212> TYPE: PRT
<213> ORGANISM: Homo sapiens
```

```
<400> SEQUENCE: 62

Glu Ala Thr Leu Gln Asp Cys Pro Ser Gly Pro Trp Gly Lys
1               5                   10

<210> SEQ ID NO 63
<211> LENGTH: 13
<212> TYPE: PRT
<213> ORGANISM: Homo sapiens

<400> SEQUENCE: 63

Glu Asp Ser Leu Glu Ala Gly Leu Pro Leu Gln Val Arg
1               5                   10

<210> SEQ ID NO 64
<211> LENGTH: 18
<212> TYPE: PRT
<213> ORGANISM: Homo sapiens

<400> SEQUENCE: 64

Thr Thr Leu Ser Gly Ala Pro Cys Gln Pro Trp Ala Ser Glu Ala Thr
1               5                   10                  15

Tyr Arg

<210> SEQ ID NO 65
<211> LENGTH: 20
<212> TYPE: PRT
<213> ORGANISM: Homo sapiens

<400> SEQUENCE: 65

Gln Gly Tyr Asp Leu Ser Pro Leu Thr Pro Leu Ser Glu Leu Ser Val
1               5                   10                  15

Gln Cys Asn Arg
            20

<210> SEQ ID NO 66
<211> LENGTH: 17
<212> TYPE: PRT
<213> ORGANISM: Homo sapiens

<400> SEQUENCE: 66

Gln Glu Glu Gln Thr Thr Cys Thr Thr Glu Gly Trp Ser Pro Glu Pro
1               5                   10                  15

Arg

<210> SEQ ID NO 67
<211> LENGTH: 20
<212> TYPE: PRT
<213> ORGANISM: Homo sapiens

<400> SEQUENCE: 67

Gln Gly Tyr Asp Leu Ser Pro Leu Thr Pro Leu Ser Glu Leu Ser Val
1               5                   10                  15

Gln Cys Asn Arg
            20

<210> SEQ ID NO 68
<211> LENGTH: 17
<212> TYPE: PRT
<213> ORGANISM: Homo sapiens

<400> SEQUENCE: 68
```

```
Gly Phe Leu Ala Tyr Tyr Gln Ala Val Asp Leu Asp Glu Cys Ala Ser
1               5                   10                  15

Arg

<210> SEQ ID NO 69
<211> LENGTH: 18
<212> TYPE: PRT
<213> ORGANISM: Homo sapiens

<400> SEQUENCE: 69

Leu Gly Tyr Val Thr Ala Asp Gly Glu Thr Ser Gly Ser Ile Thr Cys
1               5                   10                  15

Gly Lys

<210> SEQ ID NO 70
<211> LENGTH: 18
<212> TYPE: PRT
<213> ORGANISM: Homo sapiens

<400> SEQUENCE: 70

Glu Gln Val Gln Ser Cys Gly Pro Pro Glu Leu Leu Asn Gly Asn
1               5                   10                  15

Val Lys

<210> SEQ ID NO 71
<211> LENGTH: 20
<212> TYPE: PRT
<213> ORGANISM: Homo sapiens

<400> SEQUENCE: 71

Ser Thr Asp Thr Ser Cys Val Asn Pro Pro Thr Val Gln Asn Ala His
1               5                   10                  15

Ile Leu Ser Arg
            20

<210> SEQ ID NO 72
<211> LENGTH: 13
<212> TYPE: PRT
<213> ORGANISM: Homo sapiens

<400> SEQUENCE: 72

Ile Thr Cys Ala Glu Glu Gly Trp Ser Pro Thr Pro Lys
1               5                   10

<210> SEQ ID NO 73
<211> LENGTH: 10
<212> TYPE: PRT
<213> ORGANISM: Homo sapiens

<400> SEQUENCE: 73

Thr Gly Asp Ile Val Glu Phe Val Cys Lys
1               5                   10

<210> SEQ ID NO 74
<211> LENGTH: 13
<212> TYPE: PRT
<213> ORGANISM: Homo sapiens

<400> SEQUENCE: 74

Leu Pro Asp Thr Pro Gln Gly Leu Leu Gly Glu Ala Arg
1               5                   10
```

```
<210> SEQ ID NO 75
<211> LENGTH: 16
<212> TYPE: PRT
<213> ORGANISM: Homo sapiens

<400> SEQUENCE: 75

Gly Asn Cys Val Ser Leu Leu Ser Pro Ser Pro Glu Gly Asp Pro Arg
1               5                   10                  15

<210> SEQ ID NO 76
<211> LENGTH: 13
<212> TYPE: PRT
<213> ORGANISM: Homo sapiens

<400> SEQUENCE: 76

Ser Asp Leu Ala Val Pro Ser Glu Leu Ala Leu Leu Lys
1               5                   10

<210> SEQ ID NO 77
<211> LENGTH: 13
<212> TYPE: PRT
<213> ORGANISM: Homo sapiens

<400> SEQUENCE: 77

Ala Ala Ile Pro Ser Ala Leu Asp Thr Asn Ser Ser Lys
1               5                   10

<210> SEQ ID NO 78
<211> LENGTH: 14
<212> TYPE: PRT
<213> ORGANISM: Homo sapiens

<400> SEQUENCE: 78

Gln Glu Pro Gly Glu Asn Ser Glu Ile Leu Pro Thr Leu Lys
1               5                   10

<210> SEQ ID NO 79
<211> LENGTH: 15
<212> TYPE: PRT
<213> ORGANISM: Homo sapiens

<400> SEQUENCE: 79

Asn Ser Cys Pro Pro Thr Ser Glu Leu Leu Gly Thr Ser Asp Arg
1               5                   10                  15

<210> SEQ ID NO 80
<211> LENGTH: 20
<212> TYPE: PRT
<213> ORGANISM: Homo sapiens

<400> SEQUENCE: 80

Val Asp Asn Ala Leu Gln Ser Gly Asn Ser Gln Glu Ser Val Thr Glu
1               5                   10                  15

Gln Asp Ser Lys
            20

<210> SEQ ID NO 81
<211> LENGTH: 14
<212> TYPE: PRT
<213> ORGANISM: Homo sapiens

<400> SEQUENCE: 81

Asp Ser Thr Tyr Ser Leu Ser Ser Thr Leu Thr Leu Ser Lys
1               5                   10
```

<210> SEQ ID NO 82
<211> LENGTH: 13
<212> TYPE: PRT
<213> ORGANISM: Homo sapiens

<400> SEQUENCE: 82

Asn Val Pro Leu Pro Val Ile Ala Glu Leu Pro Pro Lys
1               5                   10

<210> SEQ ID NO 83
<211> LENGTH: 18
<212> TYPE: PRT
<213> ORGANISM: Homo sapiens

<400> SEQUENCE: 83

Val Ala Gly Leu Glu Ser Leu Gly Asp Leu Phe Pro Asn Leu Thr Val
1               5                   10                  15

Ile Arg

<210> SEQ ID NO 84
<211> LENGTH: 13
<212> TYPE: PRT
<213> ORGANISM: Homo sapiens

<400> SEQUENCE: 84

Ala Glu Asn Gly Pro Gly Pro Gly Val Leu Val Leu Arg
1               5                   10

<210> SEQ ID NO 85
<211> LENGTH: 14
<212> TYPE: PRT
<213> ORGANISM: Homo sapiens

<400> SEQUENCE: 85

Gly Thr Cys Glu Gln Gly Pro Ser Ile Val Thr Pro Pro Lys
1               5                   10

<210> SEQ ID NO 86
<211> LENGTH: 13
<212> TYPE: PRT
<213> ORGANISM: Homo sapiens

<400> SEQUENCE: 86

Gly Glu Gly Glu Pro Cys Gly Gly Gly Ala Gly Arg
1               5                   10

<210> SEQ ID NO 87
<211> LENGTH: 19
<212> TYPE: PRT
<213> ORGANISM: Homo sapiens

<400> SEQUENCE: 87

Asn Leu Asp Ala Ile Thr Thr Pro Asp Pro Thr Thr Asn Ala Ser Leu
1               5                   10                  15

Leu Thr Lys

<210> SEQ ID NO 88
<211> LENGTH: 12
<212> TYPE: PRT
<213> ORGANISM: Homo sapiens

<400> SEQUENCE: 88

Glu Ala Leu Ala Glu Asn Asn Leu Asn Leu Pro Lys

```
1               5                   10
```

<210> SEQ ID NO 89
<211> LENGTH: 19
<212> TYPE: PRT
<213> ORGANISM: Homo sapiens

<400> SEQUENCE: 89

```
Ile Leu Gln Leu Ile Leu Leu Ala Leu Ala Thr Gly Leu Val Gly Gly
1               5                   10                  15

Glu Thr Arg
```

<210> SEQ ID NO 90
<211> LENGTH: 18
<212> TYPE: PRT
<213> ORGANISM: Homo sapiens

<400> SEQUENCE: 90

```
Thr Ala Thr Glu Ser Phe Pro His Pro Gly Phe Asn Asn Ser Leu Pro
1               5                   10                  15

Asn Lys
```

<210> SEQ ID NO 91
<211> LENGTH: 19
<212> TYPE: PRT
<213> ORGANISM: Homo sapiens

<400> SEQUENCE: 91

```
Ala Phe Pro Ala Leu Thr Ser Leu Asp Leu Ser Asp Asn Pro Gly Leu
1               5                   10                  15

Gly Glu Arg
```

<210> SEQ ID NO 92
<211> LENGTH: 18
<212> TYPE: PRT
<213> ORGANISM: Homo sapiens

<400> SEQUENCE: 92

```
Ser Thr Leu Ser Val Gly Val Ser Gly Thr Leu Val Leu Leu Gln Gly
1               5                   10                  15

Ala Arg
```

<210> SEQ ID NO 93
<211> LENGTH: 17
<212> TYPE: PRT
<213> ORGANISM: Homo sapiens

<400> SEQUENCE: 93

```
Leu Pro Gly Ile Leu Ala Pro Glu Thr Val Leu Leu Pro Phe Cys Tyr
1               5                   10                  15

Lys
```

<210> SEQ ID NO 94
<211> LENGTH: 12
<212> TYPE: PRT
<213> ORGANISM: Homo sapiens

<400> SEQUENCE: 94

```
Leu Ser Glu Pro Ala Glu Leu Thr Asp Ala Val Lys
1               5                   10
```

```
<210> SEQ ID NO 95
<211> LENGTH: 12
<212> TYPE: PRT
<213> ORGANISM: Homo sapiens

<400> SEQUENCE: 95

His Ser Gln Pro Trp Gln Val Leu Val Ala Ser Arg
1               5                   10

<210> SEQ ID NO 96
<211> LENGTH: 12
<212> TYPE: PRT
<213> ORGANISM: Homo sapiens

<400> SEQUENCE: 96

Ser Pro Ile Asp Thr Phe Pro Thr Asp Pro Ile Lys
1               5                   10

<210> SEQ ID NO 97
<211> LENGTH: 15
<212> TYPE: PRT
<213> ORGANISM: Homo sapiens

<400> SEQUENCE: 97

Leu Ser Gly Leu His Gly Gln Asp Leu Phe Gly Ile Trp Ser Lys
1               5                   10                  15

<210> SEQ ID NO 98
<211> LENGTH: 11
<212> TYPE: PRT
<213> ORGANISM: Homo sapiens

<400> SEQUENCE: 98

Leu Ala Ala Ile Ala Glu Ser Gly Val Glu Arg
1               5                   10

<210> SEQ ID NO 99
<211> LENGTH: 9
<212> TYPE: PRT
<213> ORGANISM: Homo sapiens

<400> SEQUENCE: 99

Phe Ala Val Ala Thr Leu Pro Pro Ala
1               5

<210> SEQ ID NO 100
<211> LENGTH: 11
<212> TYPE: PRT
<213> ORGANISM: Homo sapiens

<400> SEQUENCE: 100

Glu Ala Val Pro Glu Pro Val Leu Leu Ser Arg
1               5                   10

<210> SEQ ID NO 101
<211> LENGTH: 19
<212> TYPE: PRT
<213> ORGANISM: Homo sapiens

<400> SEQUENCE: 101

Val Ala Gly Glu Ser Ala Glu Pro Glu Pro Glu Pro Glu Ala Asp Tyr
1               5                   10                  15

Tyr Ala Lys
```

```
<210> SEQ ID NO 102
<211> LENGTH: 9
<212> TYPE: PRT
<213> ORGANISM: Homo sapiens

<400> SEQUENCE: 102

Ser Trp Ser Val Tyr Val Gly Ala Arg
1               5

<210> SEQ ID NO 103
<211> LENGTH: 12
<212> TYPE: PRT
<213> ORGANISM: Homo sapiens

<400> SEQUENCE: 103

Glu Thr Cys Val Glu Val Ala Ser Glu Leu Gly Lys
1               5                   10

<210> SEQ ID NO 104
<211> LENGTH: 19
<212> TYPE: PRT
<213> ORGANISM: Homo sapiens

<400> SEQUENCE: 104

Gln Leu Phe Glu Ile Ser Val Pro Leu Thr Ser Val Pro Glu Leu Val
1               5                   10                  15

Pro Val Lys
```